US009005577B2

(12) United States Patent
Kolb et al.

(10) Patent No.: US 9,005,577 B2
(45) Date of Patent: Apr. 14, 2015

(54) SUBSTRATE BASED PET IMAGING AGENTS

(75) Inventors: Hartmuth C. Kolb, Playa Del Rey, CA (US); Joseph C. Walsh, Pacific Palisades, CA (US); Kai Chen, Los Angeles, CA (US); Umesh B. Gangadharmath, Los Angeles, CA (US); Gang Chen, Los Angeles, CA (US); Vani P. Mocharla, Los Angeles, CA (US); Dhanalakshmi Kasi, Los Angeles, CA (US); Peter J. H. Scott, Marina-del-Rey, CA (US); Qianwa Liang, Hacienda Heights, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 281 days.

(21) Appl. No.: 12/433,211

(22) Filed: Apr. 30, 2009

(65) Prior Publication Data

US 2010/0074843 A1    Mar. 25, 2010

Related U.S. Application Data

(60) Provisional application No. 61/049,392, filed on Apr. 30, 2008.

(51) Int. Cl.
*A61K 51/00*      (2006.01)
*A61M 36/14*    (2006.01)
*A61K 51/08*      (2006.01)

(52) U.S. Cl.
CPC .................................... *A61K 51/088* (2013.01)

(58) Field of Classification Search
CPC ....... A61K 38/00; A61K 38/02; A61K 38/03;
A61K 38/04; A61K 38/06; A61K 38/07;
A61K 38/08; A61K 51/088; A61K 51/08;
A61K 51/00; A61K 51/04; A61K 51/06;
A61K 49/00; A61K 49/0002; A61K 49/001;
A61K 49/0013; A61K 49/0015; A61K
49/0017; A61K 49/04; A61K 49/06; A61K
49/10; A61K 49/14; A61K 2123/00; A61K
2121/00; C07K 7/06; C07K 7/08; C07K 7/00;
C07K 5/00; C07K 5/06; C07K 5/08; C07K
5/10; C07K 9/00; C07K 9/001; C07K 9/006;
C07K 2/00
USPC ........... 424/1.11, 1.65, 1.69, 1.81, 1.85, 1.89,
424/9.1, 9.3, 9.4, 9.5, 9.6, 9.7, 9.8;
530/300, 317, 324, 325, 326, 327, 328,
530/329, 330, 331; 514/1, 1.1
See application file for complete search history.

(56) References Cited

U.S. PATENT DOCUMENTS

| 4,015,970 | A | 4/1977 | Hennart |
| 5,567,592 | A | 10/1996 | Benet et al. |
| 5,948,932 | A | 9/1999 | Grote et al. |
| 6,004,927 | A | 12/1999 | Benet et al. |
| 6,028,054 | A | 2/2000 | Benet et al. |
| 6,037,378 | A | 3/2000 | Grote et al. |
| 6,043,282 | A | 3/2000 | Bayer et al. |
| 6,130,247 | A | 10/2000 | Bayer et al. |
| 6,172,216 | B1 | 1/2001 | Bennett et al. |
| 6,214,986 | B1 | 4/2001 | Bennett et al. |
| 6,235,879 | B1 | 5/2001 | Kalchman et al. |
| 6,348,185 | B1 | 2/2002 | Piwnica-Worms |
| 6,525,025 | B2 | 2/2003 | Han et al. |
| 6,583,090 | B1 | 6/2003 | Gewehr et al. |
| 6,673,908 | B1 | 1/2004 | Stanton, Jr. |
| 6,979,530 | B2 | 12/2005 | Yan et al. |
| 7,030,132 | B2 | 4/2006 | Schellens et al. |
| 7,045,532 | B2 | 5/2006 | Acton et al. |
| 7,148,204 | B2 | 12/2006 | Bennett et al. |
| 7,151,092 | B2 | 12/2006 | Boyer et al. |
| 7,172,905 | B2 | 2/2007 | Mrksich et al. |
| 7,205,404 | B1 | 4/2007 | Erion et al. |
| 7,259,234 | B2 | 8/2007 | Bachovchin et al. |
| 7,402,556 | B2 | 7/2008 | Trouet et al. |
| 7,427,605 | B2 | 9/2008 | Davis et al. |
| 7,432,304 | B2 | 10/2008 | Wang et al. |
| 7,432,352 | B2 | 10/2008 | Johansen |
| 7,632,492 | B2 | 12/2009 | Grabstein et al. |
| 2002/0128282 | A1 | 9/2002 | Schellens et al. |
| 2004/0171562 | A1 | 9/2004 | Trouet et al. |
| 2005/0049177 | A1 | 3/2005 | Bachovchin et al. |
| 2005/0287639 | A1 | 12/2005 | Kwon et al. |

(Continued)

FOREIGN PATENT DOCUMENTS

| DE | 2455623 | 5/1976 |
| EP | 1127579 | 8/2001 |

(Continued)

OTHER PUBLICATIONS

Bauer et al (Journal of Nuclear Medicine, 2005, vol. 46, No. 6, pp. 1066-1074).*
Huangfu Chao-shen [Reprint Author]; Ma Yong-chao; Fang Na; Kang Yu-hua; Hu Guo-qiang; Yang Rui-sheng; Lie Bin, Effects of triazole Schiff base derivative on the differentiation and apoptosis of human hepatacarcinoma cells, Zhongguo Yaolixue Tongbao, (Apr. 2008) vol. 24, No. 4, pp. 498-503. ISSN: 1001-1978.
Smith, Graham; Perumal, Meg; Nguyen, Quang-De; Aboagye, Eric O. Glaser, Matthias; Shan, Bo; Arstad, Erik Aboagye, E. O. Design, synthesis, and biological characterization of a caspase 3/7 selective isatin labeled with 2- [(18)f] fluoroethylazide, Journal of Medicinal Chemistry, (Dec. 25, 2008) vol. 51, No. 24, pp. 8057-8067.

(Continued)

*Primary Examiner* — D L Jones
(74) *Attorney, Agent, or Firm* — Peter Kendall

(57) ABSTRACT

The present application is directed to radiolabeled imaging agents comprising a radiolabel, and a substrate, pharmaceutical compositions comprising radiolabeled imaging agents, and methods of using the radiolabeled imaging agents. The present application is further directed to methods of preparing the radiolabeled imaging agent. Such imaging agents can used in imaging studies, such as Positron Emitting Tomography (PET) or Single Photon Emission Computed Tomography (SPECT).

4 Claims, 3 Drawing Sheets

(56) References Cited

U.S. PATENT DOCUMENTS

| | | |
|---|---|---|
| 2006/0069038 A1 | 3/2006 | Colucci et al. |
| 2006/0073507 A1 | 4/2006 | Deiters et al. |
| 2006/0127337 A1 | 6/2006 | Radisson |
| 2006/0128743 A1 | 6/2006 | Schellens et al. |
| 2006/0258851 A1 | 11/2006 | Johansen |
| 2006/0275215 A1 | 12/2006 | Hiscock et al. |
| 2007/0178448 A1 | 8/2007 | Tsao et al. |
| 2007/0258996 A1 | 11/2007 | Kramer et al. |
| 2007/0265281 A1 | 11/2007 | Cottens et al. |
| 2007/0286842 A1 | 12/2007 | Brandl et al. |
| 2008/0004241 A1 | 1/2008 | Hangauer |
| 2008/0045530 A1 | 2/2008 | Brandl et al. |
| 2008/0051557 A1 | 2/2008 | Bachovchin et al. |
| 2008/0096819 A1 | 4/2008 | Grabstein et al. |
| 2008/0125347 A1 | 5/2008 | Grabstein et al. |
| 2008/0132412 A1 | 6/2008 | Wagner et al. |
| 2008/0200641 A1 | 8/2008 | Grabstein et al. |
| 2008/0214439 A1 | 9/2008 | Grabstein et al. |
| 2008/0220472 A1 | 9/2008 | Deiters et al. |
| 2008/0253967 A1 | 10/2008 | Kung et al. |
| 2008/0267882 A1 | 10/2008 | Chen et al. |
| 2008/0279768 A1 | 11/2008 | Moore et al. |
| 2008/0279918 A1 | 11/2008 | Morita et al. |
| 2009/0029441 A1 | 1/2009 | Wang et al. |
| 2009/0036674 A1 | 2/2009 | Moore |
| 2009/0041664 A1 | 2/2009 | Kopka et al. |
| 2009/0053137 A1 | 2/2009 | Moore |
| 2009/0076176 A1 | 3/2009 | Trouet et al. |
| 2009/0082324 A1 | 3/2009 | Moore |
| 2009/0110662 A1 | 4/2009 | Breitenkamp et al. |
| 2009/0137424 A1 | 5/2009 | Tsao et al. |
| 2009/0240030 A1 | 9/2009 | Ju et al. |
| 2009/0253609 A1 | 10/2009 | Fleury et al. |
| 2009/0257949 A1 | 10/2009 | Hefti et al. |

FOREIGN PATENT DOCUMENTS

| | | |
|---|---|---|
| EP | 1602663 | 12/2005 |
| EP | 1749540 | 2/2007 |
| EP | 2065057 | 6/2009 |
| ES | 2119676 | 10/1998 |
| GB | 1287749 | 9/1972 |
| JP | 56035992 | 4/1981 |
| JP | 10279371 | 10/1998 |
| JP | 2002-518521 | 6/2002 |
| JP | 2003-501024 | 1/2003 |
| RU | 2119536 | 9/1998 |
| WO | WO 9718187 | 5/1997 |
| WO | WO 9743252 | 11/1997 |
| WO | WO 0215700 | 2/2002 |
| WO | WO 03011342 A2 | 2/2003 |
| WO | WO 03038092 | 5/2003 |
| WO | WO 2005032581 | 4/2005 |
| WO | WO 2005118625 | 12/2005 |
| WO | WO 2006034332 | 3/2006 |
| WO | WO2006/082434 * | 8/2006 |
| WO | WO-2006/082434 * | 8/2006 |
| WO | WO 2006082434 A1 | 8/2006 |
| WO | WO 2006106348 | 10/2006 |
| WO | WO 2007047301 | 4/2007 |
| WO | 2007066115 A2 | 6/2007 |
| WO | WO 2007064661 | 6/2007 |
| WO | WO 2007100563 | 9/2007 |
| WO | WO 2007106544 | 9/2007 |
| WO | WO 2007106546 | 9/2007 |
| WO | WO 2007120193 | 10/2007 |
| WO | WO 2007130453 | 11/2007 |
| WO | 2008033557 A2 | 3/2008 |
| WO | WO 2008033561 A2 | 3/2008 |
| WO | WO 2008075955 | 6/2008 |
| WO | WO 2008085446 | 7/2008 |
| WO | WO 2008130326 | 10/2008 |
| WO | WO 2008134761 | 11/2008 |
| WO | WO 2009026393 | 2/2009 |
| WO | WO 2009036790 | 3/2009 |
| WO | WO 2009/063082 | 5/2009 |
| WO | WO 2009067663 | 5/2009 |
| WO | WO 2009083530 | 7/2009 |
| WO | 2009108606 | 9/2009 |
| WO | WO 2009117344 | 9/2009 |
| WO | WO 2009134405 | 11/2009 |

OTHER PUBLICATIONS

R. Haubner et al., "A18F-Galacto-RGD: Synthesis, Radiolabeling, Metabolic Stability, and Radiation Dose Estimates", Bioconjugate Chemistry, ACS, Washington, DC, vol. 15, No. 1, Jan. 1, 2004, pp. 61-69.

International Search Report of Application No. PCT/US2009/002659 dated May 6, 2010.

Sai Sudhir, V., et al.; Facile Entry into Triazole Fused Heterocycles via Sulfamidate Derived Azidoalkynes; Journal of Organic Chemistry (2009), vol. 74 (19), pp. 7588-7591.

Leyden, Rosaria, et al.; Glycotriazolop Hane Synthesis via Click Chemistry; Synlett (2009), (12), pp. 1949-1950.

Dondoni, Alessandro; Triazole: The Keystone in Glycosylated Molecular Architectures Constructed by a Click Reaction; Chemistry—An Asian Journal (2007); vol. 2 (6); pp. 700-708.

Jacinta A. Watt, et al.; 'Click' Preparation of Carbohydrate 1-Benzotriazoles, 1, 4-; Australian Journal of Chemistry; (2008), vol. 61 (11); pp. 837-846.

Shao Qiong Liu, et al.; Biodegradable Poly(ethyleneglycol)-Peptide Hydrogels with Well-Defined Structure and Properties for Cell Delivery; Biomaterials (2009), vol. 30 (8), pp. 1453-1461.

Yu L. Angell, et al.; Peptidomimetics via Coopercatalyzed Azide-Alkyne Cycloadditions; Chemical Society Reviews (2007) vol. 36 (10), pp. 1674-1689.

Karol Kacprzak; Click Chemistry—a Revolution in OrganicSynthesis; Wiadomosci Chemiczne (2005); vol. 59 (7-8); pp. 583-611.

B. P. Sadhu, et al.; Triazole Derivative (BAS 111..W) Effect on Preservation of Banana (Musaacuminata I. cv. Giant Governor); Geobios (Jodhpur, India) (1997), vol. 24 (1), pp. 55-61.

Van Delft, et al.; Enzymatic Glycosylation of Triazole—Linked GlcNAc/Glc—Peptides: Synthesis, Stability and Anti-HIV Activity of Triazole-Linked HIV-1 gp41 Glycopeptide C34 Analogues; Chembiachem; (May 4, 2009); vol. 10, No. 7; pp. 1234-1242.

R. Gopi, et al.; Differential Effects of Hexaconazole and Paclobutrazol on Biomass, Electrolyte Leakage, Lipid Peroxidation and Antioxidant Potential of *Daucus carota* L.; Colloids and Surfaces, B: Biointerf Aces (2007), vol. 60 (2), pp. 180-186.

Johan F. Billing; et al.; C2-Symmetric Macrocyclic Carbohydrate/Amino Acid Hybrids Through Copper(1)-Catalyzed Formation of 1, 2, 3-Triazoles C2-Symmetric Macrocyclic Carbohydrate/Amino Acid Hybrids Through Cooper(1)-Catalyzed Formaton of 1, 2, 3-Trizazoles; Journal of Organic Chemistry (2005); vol. 70 (12); pp. 4847-4850.

Christian W. Torne, et al.; Peptidotriazoles on Solid Phase: [1, 2, 3]-Triazoles by Regiospecific Cooper(I)-Catalyzed 1, 3-Dipolar Cycloadditions of Terminal Alkynes to Azides; Journal of Organic Chemistry (2002); vol. 67 (9); pp. 3057-3064.

V. Girijavallabhan, et al.; New Antifungal Agents: Synthesis and Biological Activity; Special Publication—Royal Society of Chemistry (1993); vol. 119 (Recent Advances in the Chemistry of Anti-Infective Agents); pp. 192-204.

C. Kar, et al.; Effect of Triazole-Type Plant Growth Regulators on Sunflower and Safflower Seed Viability; Canadian Journal of Botany (1991); vol. 69 (6); pp. 1344-1348.

Nobutaka Imamura, et al.; Occurrence of 1, 2, 4-Triazole Ring in Actinomycetes; Journal of Antibiotics (1985); vol. 38 (8); pp. 1110-1111.

A. S. Narang, et al.; 1, 2, 4 -Triazole Amino Nucleosides. 1-β-D-3'-Amino-3'-Deoxyribofuranosyl-1, 2, 4-Triazole-3-Carboxamide and Related Nucleosides; Journal of Medicinal Chemistry (1977); vol. 20 (12); pp. 1684-1687.

Ernest R. Stamper; The Effect of Chemical Combinations as Herbicides on Johnson Grass in Louisiana Sugar-Cane; Proceedings of the Southern Weed Conference (1957); pp. 40-45.

(56) References Cited

OTHER PUBLICATIONS

Hans-Ulrich Reissig, et al.; Simple Modifications of Enantiopure 1,2-oxazines Leading to Building Blocks for Carbohydrate and Peptide Mimetics; Synlett; (Aug. 13); No. 13; pp. 2069-2072.

Schraufstatteriu, et al.; Proteases and Oxidants in Experimental Pulmonary Inflammatory Injury; Journal of Clinical Investigation; (1984) vol. 73; No. 4; pp. 1175-1184.

McMahons, et al.; The Interrelationship of Super Oxide dismutase ee-1.15.1.1 and per Oxidatic Enzymes in the Red Cell; Biochimica, et Biophysica Acta; (1979); vol. 566; No. 2; pp. 253-258.

Aldhoun Mohammad, et al.; Click Azidenitrile Cycloaddition as a New Ligation Tool for the Synthesis of Tetrazoletethered C-Glycosyl α-amino adds; Journal of Organic Chemistry (Dec. 19, 2008); vol. 73; No. 24; pp. 9565-9575.

Claudia Bauer, et al., "131 I-labeled peptides as caspase substrates for apoptosis imaging", J Nucl Med, 2005, 46(6), 1066-74.

Japanese office action of Application No. 2011-507455 dated Apr. 15, 2014.

Shiroh Futaki, et al., "Membrane Transport Structure Function and Biogenesis: Arginine-rich Peptides: An Abundant Source of Membrane-Permeable Peptides Having Potential A Carriers for Intracellular Protein Delivery", The Journal of Biological Chemistry 2001, 276: 5836-5840.

Eric Vives, et al., "Cell Biology and Metabolism: A Truncated HIV-1 Tat Protein Basic Domain Rapidly Translocates through the Plasma Membrane and Accumulates in the Cell Nucleus", Journal of Biological Chemistry 1997, 272:16010-16017.

* cited by examiner

THE EXEMPLARY MECHANISM OF ACTION FOR A NOVEL
CLASS OF SUBSTRATE BASED RADIOTRACERS

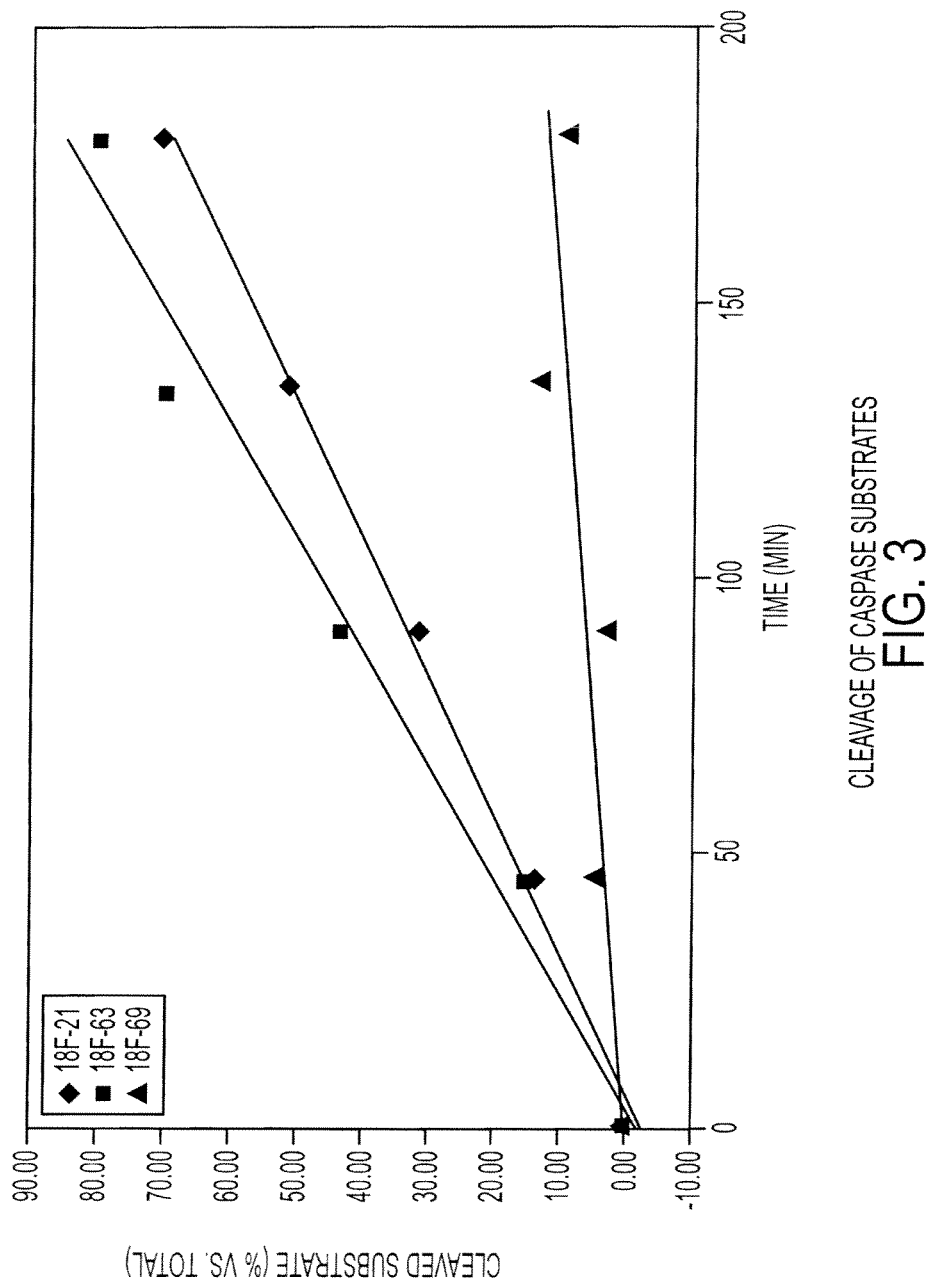

SUBSTRATE BASED PET IMAGING AGENTS

INCORPORATION BY REFERENCE

This application claims benefit of U.S. provisional patent application Ser. No. 61/049,392 filed Apr. 30, 2008.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference in their entirety, and may be employed in the practice of the invention.

FIELD OF THE INVENTION

Embodiments of the present invention are directed to radiolabeled imaging agents comprising a peptide substrate and a cell permeating vector, pharmaceutical compositions comprising the radiolabeled imaging agents, and methods of using the radiolabeled imaging agents. The present invention also includes embodiments that are further directed to methods of preparing the imaging agents. Such imaging agents, as disclosed herein, can be used in imaging studies, such as Positron Emitting Tomography (PET) or Single Photon Emission Computed Tomography (SPECT).

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see *Science*, 1998, 281, 1283-1312; Ellis et al., *Ann. Rev. Cell. Biol.*, 1991, 7, 663). Caspases are a family of cysteine protease enzymes that are key mediators in the signaling pathways for apoptosis and cell disassembly (Thornberry, *Chem. Biol.*, 1998, 5, R97-R103). There are twelve known human caspases, all of which cleave specifically at aspartyl residues and they all have stringent requirements for at least four amino acid residues on the N-terminal side of the cleavage site.

The caspases have been classified into three groups depending on the amino acid sequence that is preferred or primarily recognized. The first group of caspases, 1, 4, and 5, has been shown to prefer hydrophobic aromatic amino acids at position 4 on the N-terminal side of the cleavage site. A second group of caspases 2, 3 and 7, recognize aspartyl residues at both positions 1 and 4 on the N-terminal side of the cleavage site, and preferably a sequence of Asp-Glu-X-Asp. A third group of caspases 6, 8, 9 and 10, tolerate many amino acids in the primary recognition sequence.

A four amino acid sequence primarily recognized by the caspases has been determined for enzyme substrates (Talanian et al., *J. Biol. Chem.* 1997, 272, 9677-9682; Thornberry et al., *J. Biol. Chem.* 1997, 272, 17907-17911). Reversible tetrapeptide inhibitors have been prepared with the structure $CH_3CO—[P4]-[P3]-[P2]-CH(R)CH_2CO_2H$ where P2 to P4 represent an optimal amino acid recognition sequence and R is an aldehyde, nitrile or ketone capable of binding to the caspase cysteine sulfhydryl (Rano and Thornberry, *Chem. Biol.* 1997, 4, 149-155; Mjalli, et al., *Bioorg. Med. Chem. Lett.* 1993, 3, 2689-2692; Nicholson et al., *Nature* 1995, 376, 37-43). The utility of caspase inhibitors to treat a variety of mammalian disease states associated with an increase in cellular apoptosis has been demonstrated using peptidic caspase inhibitors. In general, the peptidic inhibitors described in the art are potent against certain caspase enzymes. Furthermore, the ability to design and employ substrates comprising radiolabeling agents that are also effective as caspase inhibitors to detect or treat these disease states is also desirable.

A number of medical diagnostic procedures, including Positron Emission Tomography (PET), and Single Photon Emission Computed Tomography (SPECT) utilize radiolabeled compounds. PET and SPECT are very sensitive techniques and require small quantities of radiolabeled compounds, called tracers. The labeled compounds are transported, accumulated and converted in vivo in exactly the same way as the corresponding non-radioactively labeled compounds. Tracers, or probes, can be radiolabeled with a radionuclide useful for PET imaging, such as $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$ and $^{131}I$, or with a radionuclide useful for SPECT imaging, such as $^{99}Tc$, $^{75}Br$, $^{61}Cu$, $^{153}Gd$, $^{125}I$, $^{131}I$ and $^{32}P$. One example of a PET probe is [$^{18}F$]-fluorodeoxyglucose ([$^{18}F$]-FDG).

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

The accurate detection of diseased tissue requires both spatial and biochemical feedback. For example, a two-step diagnosis involving both CT-based analysis and tissue biopsy guides clinicians in helping elucidate the presence and nature of a suspected disease. These two steps are necessary because CT analysis, devoid of any biochemical information, has limited benefit without complimentary information. In contrast, other imaging modalities can provide both spatial and biochemical information instantaneously. In vivo imaging of biochemical reporters provides critical biochemical information, deriving from the up- or down-regulation of specific cellular reporters, and in tandem, providing key spatial information. For instance, positron emission tomography (PET) imaging with $^{18}F$-FDG, routinely used by clinicians, accurately detects tumors and monitors tumor progression as a function of time.

$^{18}F$-FDG imaging has broad clinical applications in detecting diseased tissue, such as tumors. However, $^{18}F$-FDG uptake in tumors strictly correlates with hexokinase activity, i.e., glucose metabolism, and thus $^{18}F$-FDG cannot provide critical information regarding a tumor's phenotype, receptor expression or potential to respond to a specific type of therapy. Thus, several tumor imaging approaches focus on employing small molecule ligands or small molecule substrates, for gathering a tumor's clinically relevant information. As an example, $^{18}F$-labeled estrogen analogs differentiate between ER+ and ER− breast tumors, which FDG cannot do, providing information regarding treatment plans involving the use of hormone-based therapies. Another tracer, 3'-Deoxy-3'-[$^{18}F$]fluorothymidine ($^{18}$[F]-FLT), effectively locates proliferating S-phase cells in brain gliomas, exceeding FDG in this application. In addition, $^{18}F$-fluoromisonidazole ($^{18}$F-MISO) accurately targets hypoxic tumors which classically resist normal modes of cancer treatment, and helps guide specialized and effective therapeutic regimens. Clearly, a tumor's detection, characterization and its potential response to therapy provides critical information that guides therapeutic regimens that are more effective for the patient.

The vast majority of PET imaging agents are small molecule ligands that undergo facile radiolabeling, have optimized pharmacokinetic profiles, and efficiently localize to the target site. Unfortunately, they tend to function poorly in diseased tissue containing transiently expressed reporters or reporters expressed in low density, as the stoichiometric binding of ligand to target results in decreased signal output. Alternatively, small molecule substrate analogs useful for PET imaging, such as $^{18}$F-FDG and $^{18}$F-FLT, potentially offer enhanced signal amplification because of enzyme mediated intracellular turnover. Despite the gain in signal, the highly optimized and sensitive nature of the substrate-target interaction disallows major changes to the substrate scaffold making successful development of this class of agents notoriously difficult.

There are tracers that bind to reporters despite non-trivial modifications on the tracer. For example, radiolabeled peptide-based imaging agents possess high binding affinities and selectivities to their targets in vivo, yet these peptides bearing grossly modified chelating ligands appear to sustain their efficient binding affinities. While these tracers are not necessarily substrates for their targets, it is clear that despite their gross modifications, these agents function as effective tracers. Their success not withstanding, their usefulness as tracers is limited. Because of their size and overall electrostatic charge, they possess undesirable clearance half-lives, display poor metabolic profiles, and maintain poor cell permeability properties causing inefficient localization to intracellular reporters.

Consequently, it would be an advancement in the art to have improved imaging tracers which provide signal enhancement associated with substrate analogs in conjunction with specificity and generality associated with radiolabeled peptides. It would also be an advancement in the art to overcome difficulties in cellular transport and permeability while efficiently targeting intracellular reporters.

SUMMARY OF THE INVENTION

Embodiments of the present invention relate to effective imaging agents of formula (I) developed for detecting abnormal apoptosis in vivo:

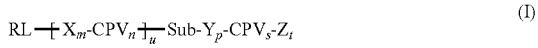

(I)

wherein:
X is a bond or a linker connected to an N-terminus of a peptide substrate;
Y is a bond or a linker;
RL is a radiolabel;
Sub is a peptide substrate;
CPV is a cell permeating vector;
Z is a capping group;
m, n, p, and s are independently 0-4;
t is 0 or 1;
u is 1 or 2; and
or a pharmaceutically acceptable salt thereof.

In the labeled substrates of the present application, the substrate is covalently attached to a cell-permeating vector, and the substrate is further coupled with a moiety comprising a radionuclide. The coupling process may occur via amide based conjugation chemistry, oxime coupling, or a 'click chemistry' linkage (i.e. a 1,4- or 1,5-disubstituted 1,2,3-triazole). These click chemistry-derived compounds are readily prepared and radiolabeled using the methods disclosed herein.

Embodiments of the present invention include, a novel class of highly effective substrate-based imaging agents. These novel agents act as substrates for their targets, have enhanced cell permeability and undergo facile radio labeling. In addition, signal amplification occurs at the target site because the mechanism of localization depends on receptor turnover, rather than stoichiometric binding, which is advantageous for disease states that exhibit transient or minimal reporter expression.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 3 is a graph of cleavage of caspase substrates.

DETAILED DESCRIPTION

The present invention includes embodiments that relate to imaging agents of formula (I) developed for detecting abnormal apoptosis in vivo:

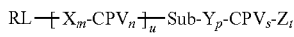
(I)

wherein:
X is a bond or a linker connected to an N-terminus of a peptide substrate;
Y is a bond or a linker;
RL is a radiolabel;
Sub is a peptide substrate;
CPV is a cell permeating vector;
Z is a capping group;
m, n, p, and s are independently 0-4;
t is 0 or 1;
u is 1 or 2; and
or a pharmaceutically acceptable salt thereof.

Figure 1:
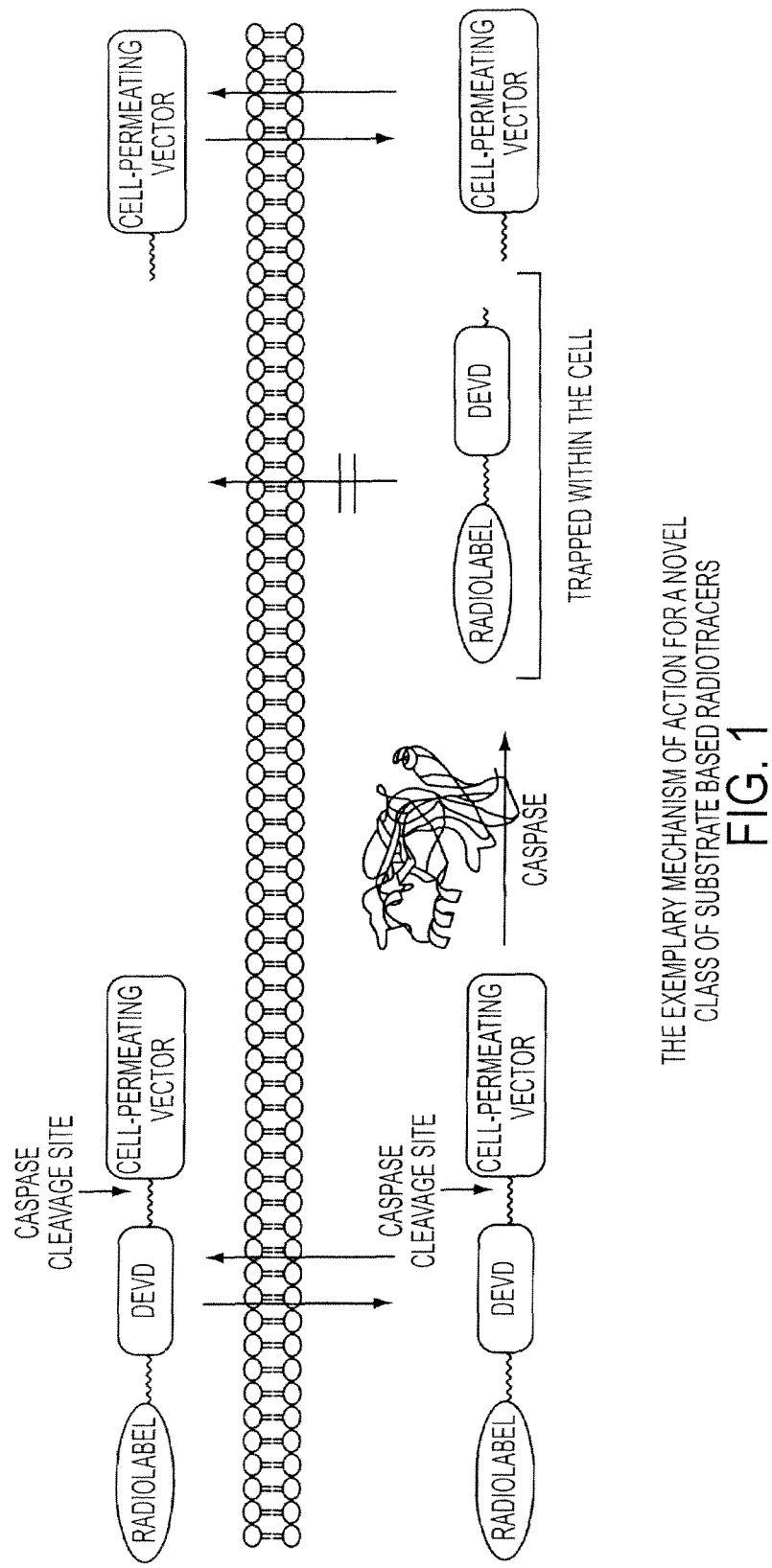
FIG. 1 is a cartoon representation of one embodiment of the compounds of the present application, illustrating the mechanism of substrate based radiotracers ('DEVD' disclosed as SEQ ID NO:2).

There is described herein a substrate that comprises both a cell-permeating vector and a radiolabeled tag (FIG. 1). Without being bound by any theory proposed herein, it is believed that the cell-permeating vector assists in transporting the substrate into the cell. Once the substrate is inside the cell, the protease reacts with the substrate and cleaves the cell-permeating vector. The freed vector freely diffuses from cell; however, the substrate, conjugated to the radiolabel, becomes cell impermeable and remains trapped intracellularly.

In one embodiment, the preferred class of reporters and substrates are proteases and their substrate peptides.

In another embodiment, the preferred radiolabel is $^{18}$F-fluorine.

In yet other embodiments, the preferred vectors are Lys4 (SEQ ID NO:1)(also may be referred to as "(Lys)$_4$" (SEQ ID NO:1)), polyethylene glycol (PEG) or amphiphilic moieties.

Specific examples of these types of novel imaging agents focus on the detection of an active cysteine protease, Caspase 3, useful for detecting apoptotic cells.

In yet other embodiments, there is provided the imaging agent as disclosed herein, wherein conjugation of PEG (poly(ethyleneglycol)) (i.e., PEGylation) to the imaging agents provides improved properties of properties of the imaging agents. Such improved properties may include plasma stability, improved immunogenicity properties, and improved pharmacokinetic profiles.

The current invention displays surprisingly excellent tumor localization, and thus high tumor to muscles ratios in vivo, despite opinions in the prior art that such peptide substrates are not expected to function well as imaging agents (J. Med. Chem. 2008, 51, 8057). In addition, contrary to published reports of the instability of $^{123}$I-labeled tetrapeptides designed to image caspase activity (PCT/GB2006/000398), the tracers in this invention do not readily lose their radiolabel in-vivo.

A published article in 2005 described the in vitro uptake of a TAT-derived DEVD (SEQ ID NO: 2) sequence labeled with $^{131}$I (J. Nucl. Med. 2005, 46, 1066). Many of the substrates failed to show a sufficiently correlative localization of the tracer in induced cells over time. Surprisingly, the present invention shows a good correlation between control and induced cells over time.

DEFINITIONS

Unless specifically noted otherwise herein, the definitions of the terms used are standard definitions used in the art of organic and peptide synthesis and pharmaceutical sciences.

An "alkyl" group is a straight, branched, saturated or unsaturated, aliphatic group having a chain of carbon atoms, optionally with oxygen, nitrogen or sulfur atoms inserted between the carbon atoms in the chain or as indicated. Alkyl groups may be optionally substituted. A ($C_1$-$C_6$)alkyl, for example, includes each of the alkyl groups that have a chain of between 1 and 6 carbon atoms, and include, for example, the groups methyl (i.e., $C_1$ alkyl), ethyl ($C_2$ alkyl), propyl ($C_3$ alkyl), isopropyl ($C_3$ alkyl), vinyl, allyl, 1-propenyl, isopropenyl, ethynyl, 1-propynyl, 2-propynyl, 1,3-butadienyl ($C_4$ alkyl), penta-1,3-dienyl ($C_5$ alkyl), and the like. An alkyl group, such as a "$C_1$-$C_6$ alkyl," that forms a part of a group or linker is a divalent alkyl group, and also may be referred to as an "alkylene" or "alkylenyl" group. Similarly, an alkenyl group, alkynyl group, aryl group, etc in a structure that is shown as a divalent group may be referred to as an alkenylenyl, alkynylenyl and arylenyl group, respectively. The representation of "($C_{1-3}$)alkyl", for example, is used interchangeably with "$C_1$-$C_3$alkyl" to mean the same.

An alkyl as noted with another group such as an aryl group, represented as "arylalkyl" for example, is intended to be a straight, branched, saturated or unsaturated aliphatic divalent group with the number of atoms indicated in the alkyl group (as in ($C_1$-$C_6$)alkyl, for example) and/or aryl group or when no atoms are indicated means a bond between the aryl and the alkyl group. Nonexclusive examples of such group include benzyl, phenylethyl and the like.

An "alkylene" group or "alkylenyl" group is a straight, branched, saturated or unsaturated aliphatic divalent group with the number of atoms indicated in the alkyl group; for example, a —($C_1$-$C_3$)alkylene- or —($C_1$-$C_3$)alkylenyl-.

The term "alkenyl" refers to unsaturated groups which contain at least one carbon-carbon double bond and includes straight-chain, branched-chain and cyclic groups. Alkene groups may be optionally substituted. Exemplary groups include 1-butenyl, 2-butenyl, 3-butenyl, isobutenyl, 1-propenyl, 2-propenyl and ethenyl.

The term "alkoxy" or "alkyloxy" includes linear or branched alkyl groups that are attached to divalent oxygen. The alkyl group is as defined above. Examples of such substituents include methoxy, ethoxy, t-butoxy, and the like. The term "alkoxyalkyl" refers to an alkyl group that is substituted with one or more alkoxy groups. Alkoxy groups may be optionally substituted. The term "aryloxy" refers to an aryl group that is attached to an oxygen, such as phenyl-O—, etc.

The term "alkynyl" refers to unsaturated groups which contain at least one carbon-carbon triple bond and includes straight-chain, branched-chain and cyclic groups. Alkyne groups may be optionally substituted. Exemplary groups include 1-butynyl, 2-butynyl, 3-butynyl, 1-propynyl, 2-propynyl and ethynyl.

The term "amphiphilic" refers to molecules that have two or more functional groups or domains that may be discrete, each group having corresponding and differing physical properties. For example, the molecules may contain both a hydrophobic and a hydrophilic group. Such different physical properties may include different affinities for water, such as one group being water-soluble and the other group or groups being a water-insoluble group. Accordingly, the first group may be hydrophobic nature or character, while one or more second groups may be hydrophilic nature or character.

The term "aryl" means one or more aromatic rings, each of which may comprise 5 or 6 core carbon atoms. Aryl includes multiple aryl rings that may be fused, as in naphthyl or non-fused, as in biphenyl. Aryl rings may also be fused or non-fused with one or more cyclic hydrocarbon, heteroaryl or heterocyclic rings. As used herein, "aryl" includes heteroaryl.

The term "carbocycle" (or carbocyclyl) as used herein refers to a $C_3$ to $C_{14}$ monocyclic or bicyclic, saturated, partially saturated or aromatic ring. Bonds in a carbocycle depicted as "---" indicate bonds that can be either single or double bonds. Carbocycles may be optionally substituted. Non-exclusive examples of carbocycle include cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl and pyrene.

As used herein, the term "cell-permeating vector" (or CPV) means molecules or compounds that enhance the transport of peptides or small molecules across cell membranes. CPV's may be known in the art, and are further described in, by way of non-limiting example, WO 06/082434. and *Bioconj. Chem.* 2000, (11), 762-771. As provided herein, such small molecules or peptides may comprise the CPV as part of the compound. Non-limiting examples of such CPVs include polyalkylene glycol derivatives, polyethylene glycol derivatives (PEGs), PEI, bile acids, cholesterol, steroids, fatty acids, poly-arginine [for example $(Arg)_{7-9}$ (SEQ ID NO: 3)], poly-lysine, antennapedia and TAT peptide fragment, as provided herein. CPVs may also be comprised of saccharide derivatives, non-limiting examples of which include glucose or galactose derivatives. CPVs may also be referred to as cellular delivery vehicles, drug delivery molecules and cell-permeable sequences.

Saccharide derivatives may be derived from mono-, di-, or tri-saccharides. Saccharides are also commonly referred to as pentoses or hexoses. Suitable saccharides include, by way of non-limiting example, glucose, galactose, maltose, mannose and lactose. Optionally, the saccharide may be functionalized to facilitate coupling with adjacent linkers or amino acids. By way of non-limiting example, sugars such as galactose may be further derivatized with groups such as amines and/or acids as follows:

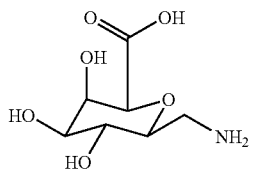 [SMILES: NCC1OC(C(=O)O)C(O)C(O)C1O]

In one embodiment of the invention, the saccharide derivative is

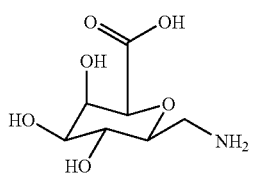 [SMILES: NCC1OC(C(=O)O)C(O)C(O)C1O]

In another embodiment of the invention, the saccharide derivative is

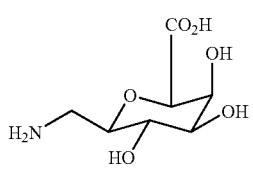

In yet another embodiment of the invention, the saccharide derivative is

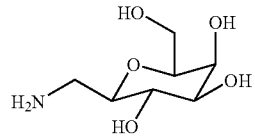

The term "diagnose" or "diagnosing" as used herein refers to methods by which the skilled artisan can estimate and determine whether or not a patient is suffering from a given disease or condition. Diagnostic evaluation may be performed on the basis of one or more diagnostic indicators, such as with a marker, the presence, absence, or the amount of which is indicative of the presence, severity or absence of the disease or condition.

The term "halo" or "halogen" means fluoro, chloro, bromo and iodo.

A "heterocycle" (or "heterocyclyl") is a carbocycle group wherein one or more of the atoms forming the ring is a heteroatom selected from the group consisting of N, O or S. The heterocycle may be saturated, partially saturated or aromatic. Bonds in a heterocycle depicted as "---" indicate bonds that can be either single or double bonds. Heterocycles may be optionally substituted. Non-exclusive examples of heterocyclyl (or heterocycle) include triazoles (e.g., 1,2,3-triazoles), piperidyl, 4-morpholyl, 4-piperazinyl, pyrrolidinyl, 1,4-diazaperhydroepinyl, acetonidyl-4-one, 1,3-dioxanyl, thiophenyl, furanyl, pyrrolyl, pyrazolyl, pyridinyl, pyrimidinyl, pyridazinyl, pyranyl and the like.

The term "linker" as used herein refers to a bond or a carbon chain comprising 1 to 10 atoms, optionally substituted with 1, 2 or 3 adjacent or non-adjacent atoms or groups, such as —NR—, O, S, —S(O)—, —S(O)$_2$—, C(O), —C(O)NR—, —C(NR)—, —C=N—O— and the like, and wherein R is H or is selected from the group consisting of $(C_{1-10})$alkyl, $(C_3-C_8)$cycloalkyl, aryl$(C_1-C_5)$alkyl, heteroaryl$(C_1-C_5)$alkyl, amino, aryl, heteroaryl, hydroxy, $(C_1-C_{10})$alkoxy, aryloxy, heteroaryloxy, each substituted or unsubstituted. The term "linker" as used herein may also be comprised of aryl, heteroaryl, amino acid, or saccharide derivatives. That is, by way of non-limiting example, the linker may be comprised of any of the groups: —CH$_2$—, —CH$_2$—CH$_2$—, —CH$_2$—O—CH$_2$—, —CH$_2$—CH$_2$—O—CH$_2$—CH$_2$—, —CH$_2$—NH—CH$_2$—, —CH$_2$—CH$_2$—NH—CH$_2$—CH$_2$—, —CH$_2$—NHC(O)—CH$_2$—, —CH$_2$—C(O)NH—CH$_2$—, —CH$_2$—C(O)—CH$_2$—, —CH$_2$—NHS(O)$_2$—CH$_2$—, —CH$_2$—S(O)$_2$NH—CH$_2$—, —CH$_2$—S(O)$_2$—CH$_2$—, etc. The linker may also comprise part of a saturated, unsaturated or aromatic ring, including polycyclic and heteroaromatic rings. In certain embodiments of the compounds of the present application, the linker may be a bond, a linker or a linker chain, for example two or more linkers joined consecutively.

As used herein, the term "polar amino acid moiety" refers to the side chain, Q, of a polar natural or unnatural amino acid. Polar natural amino acids include but are not limited to arginine, asparagine, aspartic acid, cysteine, glutamic acid, glutamine, histidine and lysine.

The term "optionally substituted" or "substituted" refers to the specific group wherein one to four hydrogen atoms in the group may be replaced by one to four substituents, independently selected from alkyl, aryl, alkylaryl, hydroxy, alkoxy, aryloxy, perhaloalkoxy, heterocycle, azido, amino (such as —NH$_2$, —NH$(C_1-C_{10})$alkyl, —N$[(C_1-C_{10})$alkyl$]_2$, —NHaryl, —N(aryl)($C_1$-$C_{10}$)alkyl, etc. . . . ), guanidino, amidino, halo, alkylthio, oxo (—C(O)—), acylalkyl, carboxy esters, carboxyl, carboxamido, nitro, acyloxy, aminoalkyl, alkylaminoaryl, alkylaminoalkyl, alkoxyaryl, arylamino, phosphono, sulfonyl, carboxamidoaryl, hydroxyalkyl, haloalkyl, cyano, alkoxyalkyl and perhaloalkyl. In addition, the term "optionally substituted" or "substituted" in reference to X or a linker, for example, includes groups substituted by one to four substituents, as identified above, that further comprises a positron or gamma emitter. Such positron emitters include, but are not limited to, $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P.

As used herein, the term "side chain" of a natural or unnatural amino acid refers to "Q" group in the amino acid formula, as exemplify with the amino acid moiety $NH_2CH(Q)CO_2H$.

As used herein, "natural amino acid" refers to the naturally occurring amino acids: glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine. The peptides, represented as their one letter code, are as known in the art and are as noted in the Table.

| Amino acid | Three letter code | One letter code |
|---|---|---|
| Alanine | ala | A |
| Arginine | arg | R |
| Asparagine | asn | N |
| Aspartic acid | asp | D |
| Asparagine or aspartic acid | asx | B |
| Cysteine | cys | C |
| Glutamic acid | glu | E |
| Glutamine | gln | Q |
| Glutamine or glutamic acid | glx | Z |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | try | W |
| Tyrosine | tyr | Y |
| Valine | val | V |

The term "unnatural amino acid" refers to any derivative of a natural amino acid including for example D and L forms, N-alkylated amino acids (also designated, for example, as N(alkyl)-AA or N-alkyl AA, wherein AA may be any amino acid or amino acid derivative) and α- and β-amino acid derivatives. It is noted that certain amino acids, e.g., hydroxyproline, that are classified as a non-natural amino acid herein, may be found in nature within a certain organism or a particular protein. The following non-exclusive examples of non-natural amino acids and amino acid derivatives may be used according to the invention (common abbreviations in parentheses): β-alanine (β-ALA), γ-aminobutyric acid (GABA), ornithine, 2-aminobutyric acid (2-Abu), α,β-dehydro-2-aminobutyric acid (8-AU), 1-aminocyclopropane-1-carboxylic acid (ACPC), aminoisobutyric acid (Aib), γ-carboxyglutamic acid, 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Stay, aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), biphenylalanine (Bip), para-bromophenylalanine (4-Br-Phe), ortho-chlorophenylalanine (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-$Cl_2$-Phe), 3,4-difluorophenylalanine (3,4-$F_2$-Phe), 3,5-diiodotyrosine (3,5-$I_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-I-Phe), 3-iodotyrosine (3-I-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine and thiazolidine-4-carboxylic acid (thioproline, Th). Additionally, N-alkylated amino acids may be used, as well as amino acids having amine-containing side chains (such as Lys and Orn) in which the amine has been acylated or alkylated.

The term "peptide fragment" as used herein, refers to a divalent peptide comprising at least 2 adjacent amino acids that is divalently linked or bonded to two different groups at the two ends of the peptide fragment. Such amino acids in the peptide fragment may be natural or unnatural amino acids or derivatives of natural or unnatural amino acids. Such derivatives may include, by way of non-limiting example, amino acids wherein side chains containing functional groups are protected with protecting groups, N-alkylated amino acids and amino acids wherein sidechains may be further substituted. Representative peptide fragments may be represented as a combination of the one letter code for each amino acid, for example, -DEVD- (SEQ ID NO: 2), -LEHD (SEQ ID NO: 4), -YVAD- (SEQ ID NO: 5), -LEVD- (SEQ ID NO: 6), -VEID- (SEQ ID NO: 7), -IETD- (SEQ ID NO: 8), -LEHD- (SEQ ID NO: 4), -DEVDD- (SEQ ID NO: 9), -DNLD- (SEQ ID NO: 10), -DQTD (SEQ ID NO: 11), -DMQD- (SEQ ID NO: 12) and the like. Peptide fragments, peptide substrates, or derivatives thereof may be synthesized by methods known to the skilled artisan, non-limiting examples of such are solution-phase chemistry and solid-phase chemistry incorporating a resin. Additionally, automated peptide synthesis may also be used. Various techniques for the synthesis of peptides are described by Lloyd-Williams, P., Albericio, F., and Girald, E. in "Chemical Approaches to the Synthesis of Peptides and Proteins," CRC Press, 1997; also see Barany, et al., Int. J. Peptide Protein Research, 1987, (30), 705-739. Resins which may be employed, by way of non-limiting example, include Rink Amide resins and Cl-trityl resins.

Protecting groups are also known to the skilled artisan, and are further described in "Protective Groups in Organic Synthesis, 3$^{rd}$ ed" Greene, T. W., Wuts, P. G. M, John Wiley & Sons, 1999.

As used herein, "alkylene glycol" refers to a fragment of poly (alkylene glycol), a polymer of an alkylene oxide. Non-limiting examples of such include polypropylene glycol and polyethylene glycol. Polypropylene glycol has the formula $(CH_2CH_2CH_2O)_r$, where r is an integer between 1 and 200, alternatively between 1 and 110 or between 10 and 90; r can also be an integer between 50 and 75.

As used herein, "PEG" or "PEG moiety" refers to a fragment of poly (ethylene glycol), a polymer of ethylene oxide. PEG has the formula $(CH_2CH_2O)_r$, where r is an integer between 1 and 200, alternatively between 1 and 110 or between 10 and 90; r can also be an integer between 50 and 75.

In one embodiment of the present invention, the r is 3-10 in PEG group that is attached to the compound of the formula I.

In further embodiments of the present invention, the PEG or propylene glycol group may also be capped at the terminal hydroxyl group with a ($C_1$-$C_6$)alkyl group. Non-limiting examples include a methyl, ethyl or propyl group and the like, to form the corresponding capped methoxy, ethoxy or propyloxy group.

The term "capping group", as used herein, may be comprised of a ($C_1$-$C_6$)— alkyl group, ($C_1$-$C_6$)-haloalkyl group, ($C_5$-$C_6$)-aryl group, or ($C_5$-$C_6$)-heteroaryl group, each of which may be optionally substituted with, by way of non limiting example, halogen, —OR'—, —C(O)NH$_2$, —C(O)NHR', —C(O)NR', CO$_2$R', SO$_2$R', —SO$_2$NHR', —SO$_2$NR', —NHC(O)R', —NR'C(O)R', or —NR'SO$_2$R'; wherein R' is hydrogen, alkyl, haloalkyl, aryl or heteroaryl.

In one embodiment of the present invention, the capping group may be propionic acid, or an ester of propionic acid.

The term "precursor", as used herein, may comprise a non-radiolabeled derivative of the substrate, designed such that conversion to the desired isotopically radio labeled agent can be performed efficiently with minimal purification requirements.

As used herein, the phrase "pharmaceutically acceptable carrier" refers to an excipient that may optionally be included in the compositions of the present application and that causes no significant adverse toxicological effects when administered in vivo.

As used herein, the term "patient" refers to any warm-blooded animal, such as a mouse, dog or human.

The terms "patient" and "subject" refer to any human or animal subject, particularly including all mammals.

As used herein, "radiochemical" is intended to encompass any organic, inorganic or organometallic compound comprising a covalently-attached radioactive isotope (a radiolabel), any inorganic radioactive ionic solution (e.g., Na[$^{18}$F]F ionic solution), or any radioactive gas (e.g., [$^{11}$C]CO$_2$), particularly including radioactive molecular imaging probes intended for administration to a patient (e.g., by inhalation, ingestion or intravenous injection) for tissue imaging purposes, which are also referred to in the art as radiopharmaceuticals, tracers, radiotracers or radioligands. Although the present invention is primarily directed to synthesis of positron-emitting molecular imaging probes for use in PET imaging systems, the invention could be readily adapted for synthesis of any radioactive compound comprising a radionuclide, including radiochemicals useful in other imaging systems, such as single photon emission computed tomography (SPECT).

As used herein, the term "radiolabel," "radioactive isotope" or "radioactive element" refers to isotopes exhibiting radioactive decay (i.e., emitting positrons) and radio labeling agents comprising a radioactive isotope. Non-limiting examples may include [$^{11}$C]methane, [$^{11}$C]carbon monoxide, [$^{11}$C]carbon dioxide, [$^{11}$C]phosgene, [$^{11}$C]urea, [$^{11}$C] cyanogen bromide, as well as various acid chlorides, carboxylic acids, alcohols, aldehydes and ketones containing carbon-11. Such isotopes or elements are also referred to in the art as radioisotopes or radionuclides. Radioactive isotopes are named herein using various commonly used combinations of the name or symbol of the element and its mass number (e.g., $^{18}$F, F-18, or fluorine-18). Exemplary radioactive isotopes include I-124, F-18 fluoride, C-11, N-13, and O-15, which have half-lives of 4.2 days, 110 minutes, 20 minutes, 10 minutes, and 2 minutes, respectively. The radioactive isotope is preferably dissolved in an organic solvent, such as a polar aprotic solvent. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Preferably, the radioactive isotope used in the present method is F-18. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

"Substituted" or a "substituent" as used herein, means that a compound or functional group comprising one or more hydrogen atoms optionally substituted by a group (a substituent) such as a —$C_1$-$C_5$alkyl, $C_2$-$C_5$alkenyl, halogen or halo (chlorine, fluorine, bromine, iodine atom), haloalkyl (such as —CF$_3$, trifluoromethyl and the like), nitro, amino (—NH$_2$, —NHR, —NR$_2$, etc. . . . ), oxo (i.e., forming —C(=O)—), —OH, carboxyl (—COOH), —C(O)OC$_1$-$C_5$alkyl, —OC$_1$-$C_5$alkyl, —C(O)NHC$_1$-$C_5$alkyl, —NHC(O)C$_1$-$C_5$alkyl, —OSOC$_1$-$C_5$alkyl, —SO$_2$C$_1$-$C_5$alkyl, —SO$_2$NHC$_1$-$C_5$alkyl, —NHSO$_2$C$_1$-$C_5$alkyl, aryl, heteroaryl and the like, each of which may be further substituted.

As used herein, the term "substrate" means a substance, or an element or a part or segment of a compound on which an enzyme acts upon. In the case of the compounds of the present application, the substrate may be a peptide sequence, peptide segment, peptide fragment or derivative thereof that binds to the active site of the enzyme, such as a caspase, including caspase 3 for example, and undergoes cleavage as disclosed herein.

"Triazole" as used herein means either 1,3,4- or 1,2,3-triazole, or mixtures thereof. In a preferred embodiment, the "triazole" is a 1,2,3-triazole, substituted in the 1- and 5-positions ("syn") or in the 1- and 4-positions ("anti") or mixtures thereof. In a particularly preferred embodiment, the 1,2,3-triazole is substituted in the 1- and 4-positions.

The compounds of the present application may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Non-limiting examples of such inorganic acids are hydrochloric, hydrobromic, hydroiodic, nitric, carbonic, sulfuric and phosphoric acid. Appropriate organic acids may be selected from aliphatic (or alkyl), cycloalkyl, aromatic, arylalkyl, heterocyclic, carboxylic and sulfonic classes of organic acids, non-limiting examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include, but are not limited to, metallic salts made from aluminum, calcium, lithium, magnesium, potassium, sodium and zinc or organic salts made from N, NT-dibenzylethylenediamine, chloroprocaine, choline, diethanolamine, ethylenediamine, meglumine-(N-methylglucamine) and procaine. Ascorbic acid may also be used as an excipient. Suitable formulations for each of these methods of administration may be found in, for example, Remington: The Science and Practice of Pharmacy, A. Gennaro, ed., 20th edition, Lippincott, Williams & Wilkins, Philadelphia, Pa.

Click Chemistry Method:

Click chemistry provides chemists an opportunity to rapidly produce libraries of candidate imaging agents, from which potential small molecule PET imaging tracers with optimal pharmacodynamic and pharmacokinetic properties may be identified. Click chemistry is a modular approach to chemical synthesis that utilizes only the most practical and reliable chemical transformations. Click chemistry techniques are described, for example, in the following references, which are incorporated herein by reference in their entirety:

Kolb, H. C.; Finn, M. G.; Sharpless, K. B. *Angewandte Chemie, International Edition* 2001, 40, 2004-2021. Kolb, H. C.; Sharpless, K. B. *Drug Discovery Today* 2003, 8, 1128-1137. Rostovtsev, V. V.; Green, L. G.; Fokin, V. V.; Sharpless, K. B. *Angewandte Chemie, International Edition* 2002, 41, 2596-2599. Tomeøe, C. W.; Christensen, C.; Meldal, M. *Journal of Organic Chemistry* 2002, 67, 3057-3064. Wang, Q.; Chan, T. R.; Hilgraf, R.; Fokin, V. V.; Sharpless, K. B.; Finn, M. G. *Journal of the American Chemical Society* 2003, 125, 3192-3193. Lee, L. V.; Mitchell, M. L.; Huang, S.-J.; Fokin, V. V.; Sharpless, K. B.; Wong, C.-H. *Journal of the American Chemical Society* 2003, 125, 9588-9589. Lewis, W. G.; Green, L. G.; Grynszpan, F.; Radic, Z.; Carlier, P. R.; Taylor, P.; Finn, M. G.; Barry, K. *Angew. Chem., Int. Ed.* 2002, 41, 1053-1057. Manetsch, R.; Krasinski, A.; Radic, Z.; Raushel, J.; Taylor, P.; Sharpless, K. B.; Kolb, H. C. *Journal of the American Chemical Society* 2004, 126, 12809-12818. Mocharla, V. P.; Colasson, B.; Lee, L. V.; Roeper, S.; Sharpless, K. B.; Wong, C.-H.; Kolb, H. C. *Angew. Chem. Int. Ed.* 2005, 44, 116-120. M. Whiting, J. Muldoon, Y.-C. Lin, S. M. Silverman, W. Lindstrom, A. J. Olson, H. C. Kolb, M. G. Finn, K. B. Sharpless, J. H. Elder, V. V. Fokin, *Angew. Chem.* 2006, 118, 1463-1467; *Angew. Chem. Int. Ed. Engl.* 2006, 45, 1435-1439.

Although other click chemistry functional groups can be utilized, such as those described in the above references, the use of cycloaddition reactions is preferred, particularly the reaction of azides with alkynyl groups. Alkynes, such as terminal alkynes, and azides undergo 1,3-dipolar cycloaddition forming 1,4-disubstituted 1,2,3-triazoles. Alternatively, a 1,5-disubstituted 1,2,3-triazole can be formed using azide and alkynyl reagents (Krasinski, A., Fokin, V. V., Sharpless, K. B. *Organic Letters* 2004, 1237-1240). Hetero-Diels-Alder reactions or 1,3-dipolar cycloaddition reactions could also be used (see Huisgen 1,3-*Dipolar Cycloaddition Chemistry* (Vol. 1) (Padwa, A., ed.), pp. 1-176, Wiley; Jorgensen *Angew. Chem. Int. Ed. Engl.* 2000, 39, 3558-3588; Tietze, L. F. and Kettschau, G. *Top. Curr. Chem.* 1997, 189, 1-120). In one particular embodiment, the click chemistry method herein provides novel compounds that are further incorporated with a PET label.

In one embodiment of the present invention, there is provided an imaging agent comprising: a) a radiolabel; b) a substrate; and c) a cell-permeating vector, wherein the radiolabel, substrate and cell-permeating vector are covalently linked together; or a pharmaceutically acceptable salt thereof.

In another embodiment of the invention, the imaging agent is comprised of the structure of formula (I):

wherein:
X is a bond or a linker connected to an N-terminus of a peptide substrate;
Y is a bond or a linker;
RL is a radiolabel;
Sub is a peptide substrate;
CPV is a cell permeating vector;
Z is a capping group;
m, n, p, and s are independently 0-4;
t is 0 or 1;
u is 1 or 2; and
or a pharmaceutically acceptable salt thereof.

In another embodiment of the invention, the imaging agent is comprised of the structure of formula (I), wherein:
X is a bond or a linker connected to an N-terminus of a peptide substrate;
Y is a bond or a linker;
RL is a radiolabel;
Sub is a peptide substrate,
CPV is a cell permeating vector;
Z is a capping group;
m, p, and s are independently 0-4;
n is 0;
t is 1; and
u is 1

In another embodiment of the invention, the imaging agent is comprised of the structure of formula (I), wherein:
$X_m$ is a bond or $X^2X^3X^4$, wherein $X^2$ is a $(C_{1-10})$alkylenyl group, aryl group or heteroaryl group, $X^3$ is a heteroaryl group or —C=N—O—, $X^4$ is a $(C_{1-10})$alkylenyl group, wherein one of the $(C_{1-10})$alkylenyl carbon atoms is optionally replaced with —CO—, —CONR"—, —NR"CO—, —NR"—, —O— or —S—;
Y is a bond or a linker;
RL is a radiolabel selected from the group consisting of $^{11}C$ or $^{18}F$;
Sub is a peptide substrate selected from the group consisting of -DEVD- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD- (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19), -VDVAD- (SEQ ID NO: 20), -VDVADGW- (SEQ ID NO: 21), -RGVDQQDGKNHW- (SEQ ID NO: 22), -GVDQQDGKNW (SEQ ID NO: 23), -VDQQDGKNW- (SEQ ID NO: 24), -DQQDGKNW- (SEQ ID NO: 25), -QQDGKNW- (SEQ ID NO: 26), -VDQQDGKW- (SEQ ID NO: 27), -VDQQDGW- (SEQ ID NO: 28), -VDQQDW- (SEQ ID NO: 29), -WEHD- (SEQ ID NO: 30), -YVAD- (SEQ ID NO: 5), -AEVD- (SEQ ID NO: 31), -IETD- (SEQ ID NO: 8), -AEVD- (SEQ ID NO: 31), -VEHD- (SEQ ID NO: 32), -XEXDAMC- (SEQ ID NO: 33), -DEVDAMC- (SEQ ID NO: 34), -VEHDAMC- (SEQ ID NO: 35), -VAD- FMK- (SEQ ID NO: 36), -YEVDGW- (SEQ ID NO: 37), -LEVDGW- (SEQ ID NO: 38), -VDQMDGW- (SEQ ID NO: 39), -VDVADGW- (SEQ ID NO: 21), -VQVDGW- (SEQ ID NO: 40), VDQVDGW- (SEQ ID NO: 41), -DEVDAMC- (SEQ ID NO: 34), -VD-fmk-, -VAD-fmk-, -YVAD-fmk-('YVAD' disclosed as SEQ ID NO: 5), -ID-fmk-, -LD-fmk, -FD-fmk-, -AD-fmk-, -GD-fink-, -KD-fmk-, -ED-fmk- and -DEVDAFC- (SEQ ID NO: 42);

CPV is selected from the group consisting of polyethyleneimine, PEG, PEI-PEG, PEG-PEI, Lys4(SEQ ID NO: 1), polyamines, histidylated poly-L-lysine, polyarginine, polyornithine, cationic liposomes and lipids, saccharide derivatives and polylysine;

Z is a capping group;
p is 0-4;
n is 0; and
s is 1;

In another embodiment of the invention, the imaging agent is comprised of the structure of formula (I), wherein:

$X_m$ is $X^2X^3X^4$, wherein $X^2$ is $-(CH_2)_2-$, $X^3$ is a triazole, $X^4$ is $-CH_2C(O)-$;
Y is a —AlaNH—;
RL is $^{18}F$;
Sub is -DEVD- (SEQ ID NO: 2);
CPV is $(-CH_2CH_2O-)_4$;
Z is $-CH_2CH_2CO_2H$;
n is 0; and
s is 1;

In another embodiment of the invention, the imaging agent is comprised of the structure of formula (I), wherein:

X is a bond or a linker connected to an N-terminus of a peptide substrate;
Y is a bond or a linker;
RL is a radiolabel;
Sub is a peptide substrate;
CPV is a cell permeating vector;
Z is a capping group;
m, p, and n are independently 0-4; and
s is 0;

In another embodiment of the invention, the imaging agent is comprised of the structure of formula (I), wherein:

$X_m$ is $X^2X^3X^4$, wherein $X^2$ is $C_1$-$C_6$alkylene, $X^3$ is a heteroaryl group, $X^4$ is a $(C_{1-10})$alkylenyl group, wherein one of the $(C_{1-10})$alkylenyl carbon atoms is optionally replaced with —CO—;
Y is a bond or a linker;
RL is $^{18}F$;
Sub is a peptide substrate selected from the group consisting of -DEVD- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD- (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19) and -VDVAD- (SEQ ID NO: 20);
CPV is selected from the group consisting of a polyethyleneimine, PEG, PEI-PEG, PEG-PEI, Lys4 (SEQ ID NO: 1), polyamines, histidylated poly-L-lysine, polyarginine, polyornithine, cationic liposomes and lipids, saccharide derivatives and polylysine;
Z is a capping group;
p is 0-4;
n is 1; and
s is 0;

In another embodiment of the invention, the imaging agent is comprised of the structure of formula (I), wherein:

$X_m$ is $X^2X^3X^4$, wherein $X^2$ is $C_1$-$C_6$alkylene, $X^3$ is a heteroaryl group, $X^4$ is a $(C_{1-10})$alkylenyl group, wherein one of the $(C_{1-10})$alkylenyl carbon atoms is optionally replaced with —CO—;
Y is a bond or a linker;
RL is $^{18}F$;
Sub is a peptide substrate selected from the group consisting of -DEVD- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD- (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19) and -VDVAD- (SEQ ID NO: 20);
CPV is independently selected from the group consisting of a polyethyleneimine, PEG, PEI-PEG, PEG-PEI, Lys4 (SEQ ID NO: 1), polyamines, histidylated poly-L-lysine, polyarginine, polyornithine, cationic liposomes and lipids, saccharide derivatives and polylysine;
Z is a capping group;
p is 0-4;
n is 1; and
s is 1;

In one embodiment of the invention, the radiolabel is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

In another embodiment, the radiolabel is selected from the group consisting of $^{11}C$ and $^{18}F$.

In one embodiment of the invention, the radiolabel is a PET or SPECT based isotope.

In another embodiment of the invention, the PET or SPECT based isotope is selected from the group consisting of $^{18}F$, $^{64}Cu$ and $^{99m}Tc$.

In one embodiment, the radiolabel is attached to the substrate using click chemistry, chelation chemistry, oxime formation, or amide based conjugation chemistry.

In another embodiment, the radiolabel is attached to the substrate using click chemistry.

In another embodiment of the invention, the substrate comprises a peptide fragment.

In yet another embodiment of the invention, the peptide substrate is selected from the group consisting of a dipeptide, tripeptide, tetrapeptide, pentapeptide, hexapeptide, heptapeptide, octapeptide and nonapeptide.

In yet a further embodiment of the invention, the peptide fragment is comprised of N-alkyl valine.

In yet a further embodiment of the invention, the peptide fragment is Asp-Glu-N-methyl Val-Asp.

In a further embodiment, the peptide fragment is selected from the group consisting of -DEVD- (SEQ ID NO: 2), -DE(N-alkyl V)D- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD- (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19), -VDVAD- (SEQ ID NO: 20), -VDVADGW- (SEQ ID NO: 21), -RGVDQQDGKNHW- (SEQ ID NO: 22), -GVDQQDGKNW (SEQ ID NO: 23), -VDQQDGKNW- (SEQ ID NO: 24), -DQQDGKNW- (SEQ ID NO: 25), -QQDGKNW- (SEQ ID NO: 26), -VDQQDGKW- (SEQ ID NO: 27), -VDQQDGW- (SEQ ID NO: 28), -VDQQDW- (SEQ ID NO: 29), -WEHD- (SEQ ID NO: 30), -YVAD- (SEQ ID NO: 5), -AEVD- (SEQ ID NO: 31), -IETD- (SEQ ID NO: 8), -AEVD- (SEQ ID NO: 31), -WEHD- (SEQ ID NO: 30), -VEHD- (SEQ ID NO: 32), -XEXDAMC- (SEQ ID NO: 33), -DEVDAMC- (SEQ ID NO: 34), -VEHDAMC- (SEQ ID NO: 35), -VADFMK- (SEQ ID NO: 36), -YEVDGW- (SEQ ID NO: 37), -LEVDGW- (SEQ ID NO: 38), -VDQMDGW- (SEQ ID NO: 39), -VD-VADGW- (SEQ ID NO: 21), -VQVDGW- (SEQ ID NO: 40), VDQVDGW- (SEQ ID NO: 41), -DEVDAMC- (SEQ ID NO: 34), -VD-fmk-VAD-fmk-, -YVAD-fmk-('YVAD' disclosed as SEQ ID NO: 5), -ID-fmk-, -L-D-fmk, -FD-fmk-, -AD-fmk-, -GD-fmk-, -KD-fmk-, -ED-fmk- and -DEVDAFC- (SEQ ID NO: 42). As used herein, fmk is fluoromethylketone.

In one embodiment of the invention, the peptide substrate is synthesized via solid-phase synthesis.

In another embodiment of the invention, the peptide substrate is synthesized using a Rink or Cl-trityl resinIn a particular embodiment of the invention, X is a bond or a $(C_{1-10})$ alkylenyl group, unsubstituted or substituted with 1, 2, 3 or 4 $X^1$, wherein one of the $(C_1-C_{10})$alkylenyl carbon atoms is optionally replaced by a group selected from —C(O)—, —C(O)NR'—, —NR'C(O)—, —NR'—, —O— and —S—; Y is a bond or a $(C_1-C_{10})$alkylenyl group, unsubstituted or substituted with 1, 2, 3 or 4 $X^1$, wherein one of the $(C_1-C_{10})$ alkylenyl carbon atoms is optionally replaced by a group selected from —C(O)—, —C(O)NR"—, —NR"C(O)—, —NR"—, —O— and —S—; R' and R" are independently selected from the group consisting of H, $(C_1-C_6)$alkyl, —C(O)$(C_1-C_3)$alkyl, —C(O)NH$(C_1-C_3)$alkyl and —CO$_2$ $(C_1-C_3)$alkyl; and each $X^1$ is independently selected from the group consisting of hydroxyl, thiol, amino, $(C_1-C_6)$alkyl, $(C_1-C_6)$alkoxy, thio$(C_1-C_6)$alkyl and halo.

In another embodiment, X is a $(C_{1-10})$alkylenyl, unsubstituted or substituted with 1 or 2 $X^1$.

In one embodiment, the cell-permeating vector is selected from the group consisting of polyethyleneimine (PEI, MW=25 kDA), PEG, PEI-PEG, PEG-PEI, Lys4 (SEQ ID NO: 1), polyamines, histidylated poly-L-lysine, polyarginine, polyornithine, cationic liposomes and lipids, saccharide derivatives, TAT peptide fragment and polylysine.

In a particular embodiment, the cell-permeating vector is an amphiphilic moiety.

In another embodiment, the amphiphilic moiety is selected from the group consisting of polyethyleneimine, polyamines, histidylated poly-L-lysine, polyarginine, polyornithine, cationic liposomes and lipids, and polylysine.

In a another embodiment, the cell-permeating vector is sacharide derivative.

In embodiments wherein the cell-permeating vector is a polypeptide, such as poly-L-lysine, polyarginine, polyornithine, polylysine or TAT peptide fragment, the C-terminus of the amino acid may exist as an aldehyde (i.e., —CHO), an amide, or an amide derivative, such as a protected amide.

In still a further embodiment, the cell permeating vector is selected from the group consisting of a polyethyleneimine, PEG, PEI-PEG, PEG-PEI, Lys4 (SEQ ID NO: 1), polyamines, histidylated poly-L-lysine, polyarginine, polyornithine, cationic liposomes and lipids, polylysine and saccharide derivatives; the peptide substrate is selected from the group consisting of -DEVD- (SEQ ID NO: 2), -DE(N-alkyl V)D- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD- (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19) and -VDVAD- (SEQ ID NO: 20); X is —CH$_2$CH$_2$-triazole-CH$_2$C(O)—; and the radiolabel is $^{18}$F.

In yet another embodiment, the imaging agent is selected from the group consisting of:

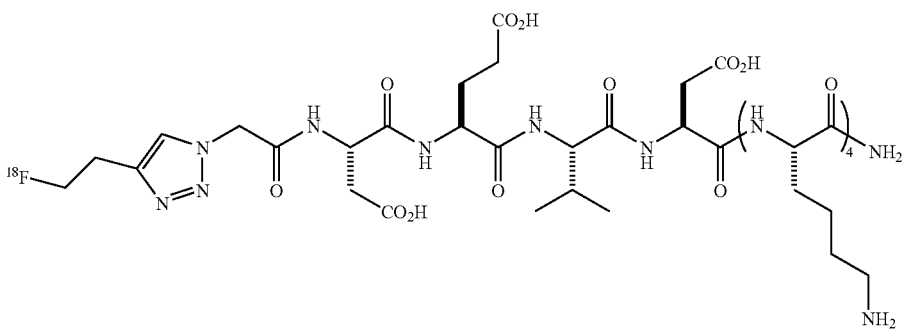

1

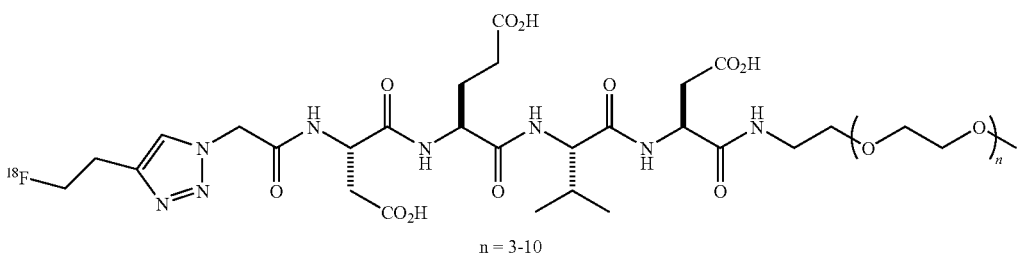

2 n = 3-10

-continued

3

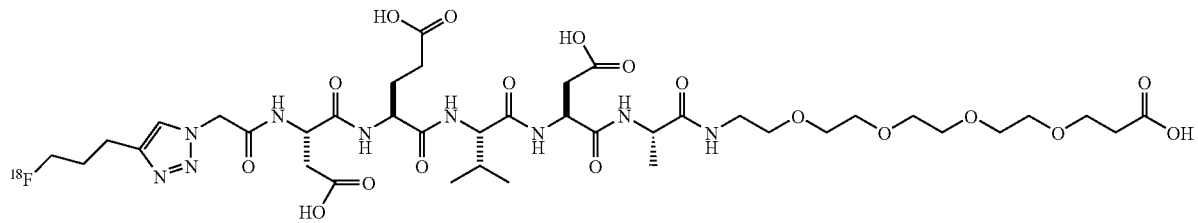

Also provided herein is a method for a imaging reporter in vivo, the method comprising contacting the imaging agent of any of the above embodiments and variations, to a cell and imaging the reporter in-vivo.

In one embodiment, the reporter is a protease or nuclease.

In another embodiment, the protease is a caspase.

In yet another embodiment, the protease is Caspase 3.

Also provided herein is a method for detecting or diagnosing a disease involving abnormal apoptosis in a mammal, the method comprising administering an imaging agent of any one of the above to the mammal, and detecting the presence of retained radioactivity in the mammal.

In yet another embodiment, there is provided the above method, wherein the detecting step employs a nuclear imaging technique selected from the group consisting of positron emission tomography (PET) and single photon emission computed tomography (SPECT) for monitoring a distribution of the imaging agent within the body or within a portion thereof.

In still a further embodiment, there is provided a method of visualizing caspase activity in a body of a patient, the method comprising: (a) administering to the patient the imaging agent of any one of the above; and (b) employing a nuclear imaging technique selected from the group consisting of positron emission tomography (PET) and single photon emission computed tomography (SPECT) for visualizing a distribution of the imaging agent within the body or within a portion thereof.

All of the compounds disclosed herein may be single enantiomers or mixtures of diastereomers.

One embodiment of the present invention is a pharmaceutical composition comprising any of the compounds and imaging agents described herein, and a pharmaceutically acceptable carrier.

In another embodiment of the present invention, the pharmaceutically acceptable carrier contains ascorbic acid.

Another embodiment of the present invention is a method of using the above pharmaceutical composition as a tracer in Positron Emission Tomography (PET) or Single Photon Emission Computed Tomography (SPECT).

A further embodiment of the present invention is a method of visualizing caspase activity within a body of a patient, the method comprising: (a) administering to the patient any of the above cited compounds and compositions; and (b) employing a nuclear imaging technique selected from the group consisting of positron emission tomography (PET) and single photon emission computed tomography (SPECT) for visualizing a distribution of the compounds within the body or within a portion thereof Pharmaceutical compositions of the compounds of the invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Non-limiting examples of suitable diluents are normal isotonic saline solution, 5% dextrose in water or buffered sodium or ammonium acetate solution. Such formulations are especially suitable for parenteral administration but may also be used for oral administration. Excipients, such as, for example, ascorbic acid, polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers may include, but are not limited to, syrup, peanut oil, olive oil, glycerin, saline, alcohols, or water. Solid carriers may include, but are not limited to, starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The pharmaceutical preparations may be made following the any of the conventional techniques of pharmacy involving, by way of non-limiting example, milling, mixing, granulation, and compressing, when necessary, for tablet forms; or milling, mixing, and filling for hard gelatin capsule forms. When a liquid carrier is used, the preparation may be in the form of a syrup, elixir, emulsion, or an aqueous or non-aqueous suspension. Such a liquid formulation may be administered directly, by way of non-limiting example, orally or subcutaneously, or filled into a soft gelatin capsule. Suitable formulations for each of these methods of administration may be found in, for example, REMINGTON: THE SCIENCE AND PRACTICE OF PHARMACY, A. Gennaro, ed., 20th edition, Lippincott, Williams & Wilkins, Philadelphia, Pa.

The pharmaceutical compositions of the invention may also be in the form of a sterile injectable preparation. Formulations suitable for parenteral administration include, by way of non-limiting example, aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

In one embodiment, the compounds disclosed herein may be prepared, in part, using click chemistry. Click chemistry, as used in this application, describes the rapid, selective and specific formation of 1,4- or 1,5-disubstituted 1,2,3-triazoles starting from alkyl azides and terminal alkynes. One or more triazole moieties comprising the radiolabeled tag are attached to the substrate, which is also attached to the cell-permeating vector. As disclosed herein, click chemistry is a high-yielding and modular approach and as such, the pharmacokinetic properties of these substrates and their analogs are readily modified.

In an another embodiment, [F-18]labeled tracers may be prepared by first preparing [F-18]fluoroazide and coupling this group with a terminal alkyne present on a suitable precursor. Couplings of this nature are also known in the art (Bioconjugate Chem. 2007, 18(3), 989-993). An example is shown, for example, in Scheme A.

Scheme A: General synthesis of radiolabeled tracer synthesis via click chemistry.

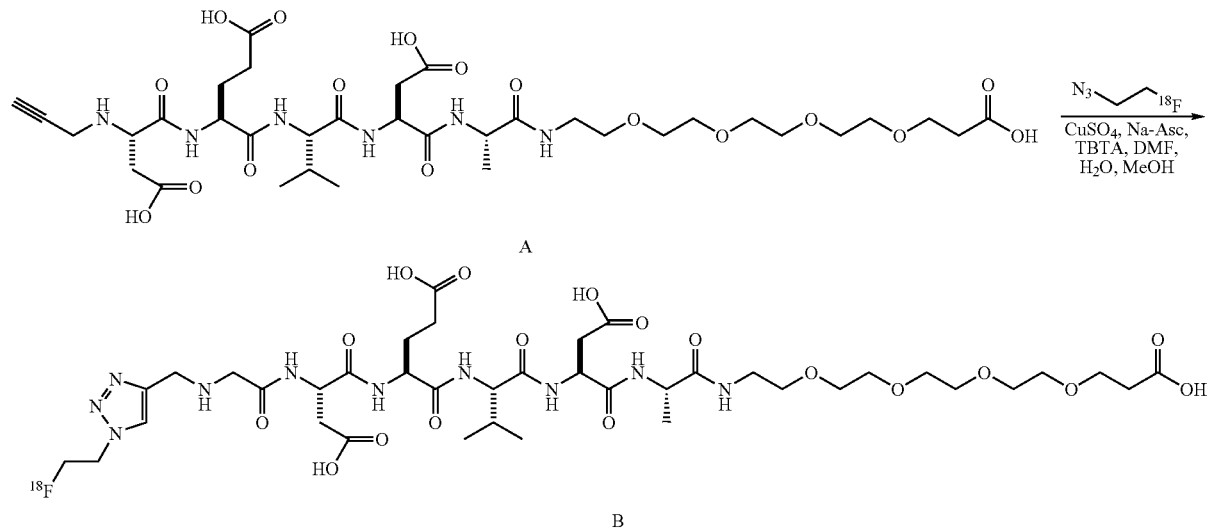

In an another embodiment, the coupling of [F-18]labeled tracers may proceed via thermal coupling of either [F-18] labeled azides or alkynes with precursors containing the complimentary azide or alkyne functionality as shown, for example, in Scheme B.

Scheme B: General synthesis of radiolabeled tracer synthesis via click chemistry.

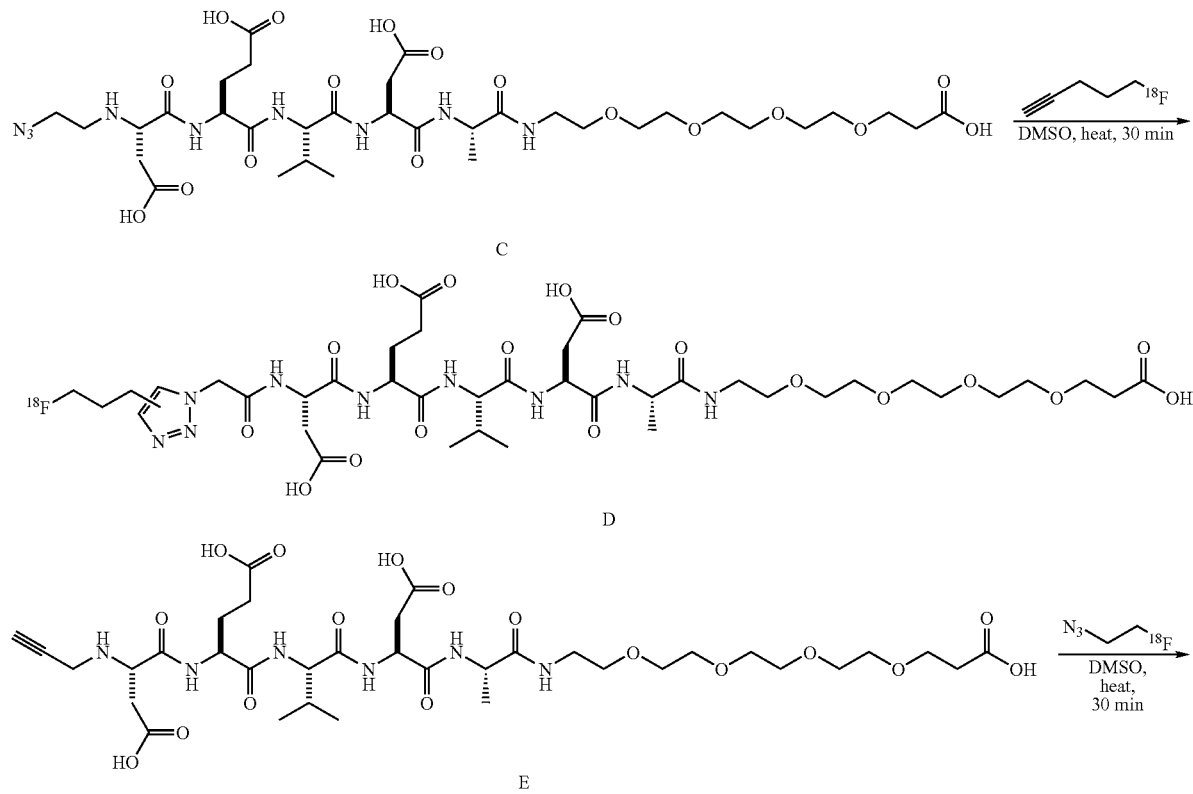

-continued

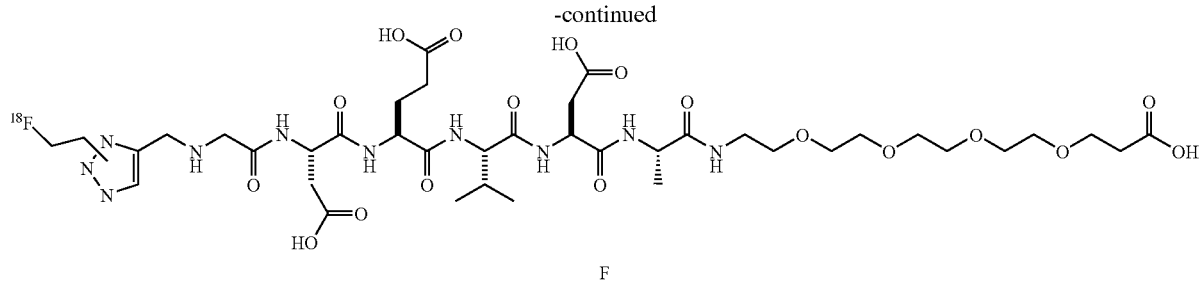

F

In yet another embodiment, [F-18]labeled tracers may be prepared by first synthesizing [F-18]fluoroethylamine and coupling with the free acid on a suitable precursor followed by deprotection and RP-HPLC purification. The coupling of [F-18]fluoroethylamine with peptides bearing a free acid is known in the art (J. Labelled Cmpds. Radiopharm. 2002, 45(3), 217-229). Several examples are shown, for example, in Scheme C.

Scheme C: General synthesis of radiolabeled tracer synthesis via amide coupling.

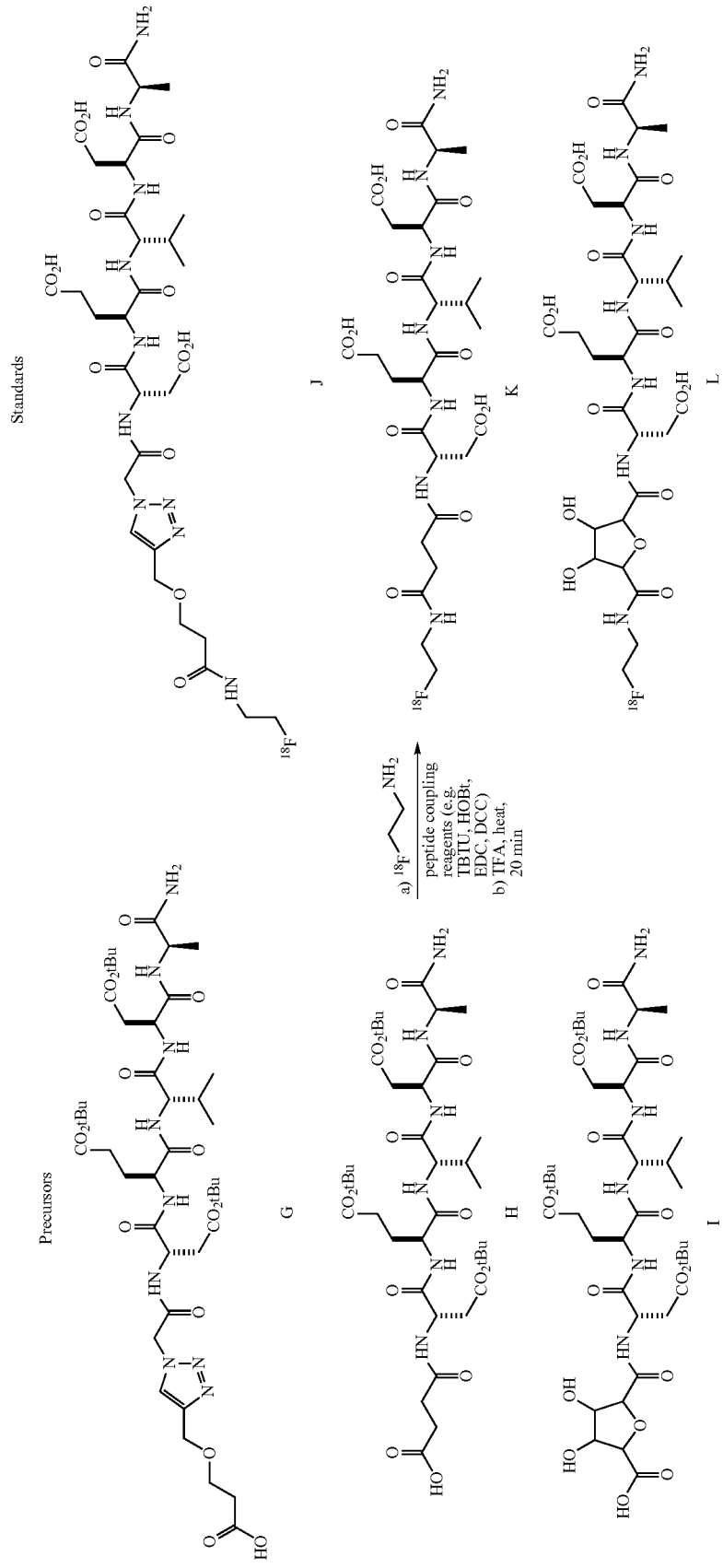
Scheme C: General synthesis of radiolabeled tracer synthesis via amide coupling.

The invention will now be further described by way of the following non-limiting examples:

Example 1

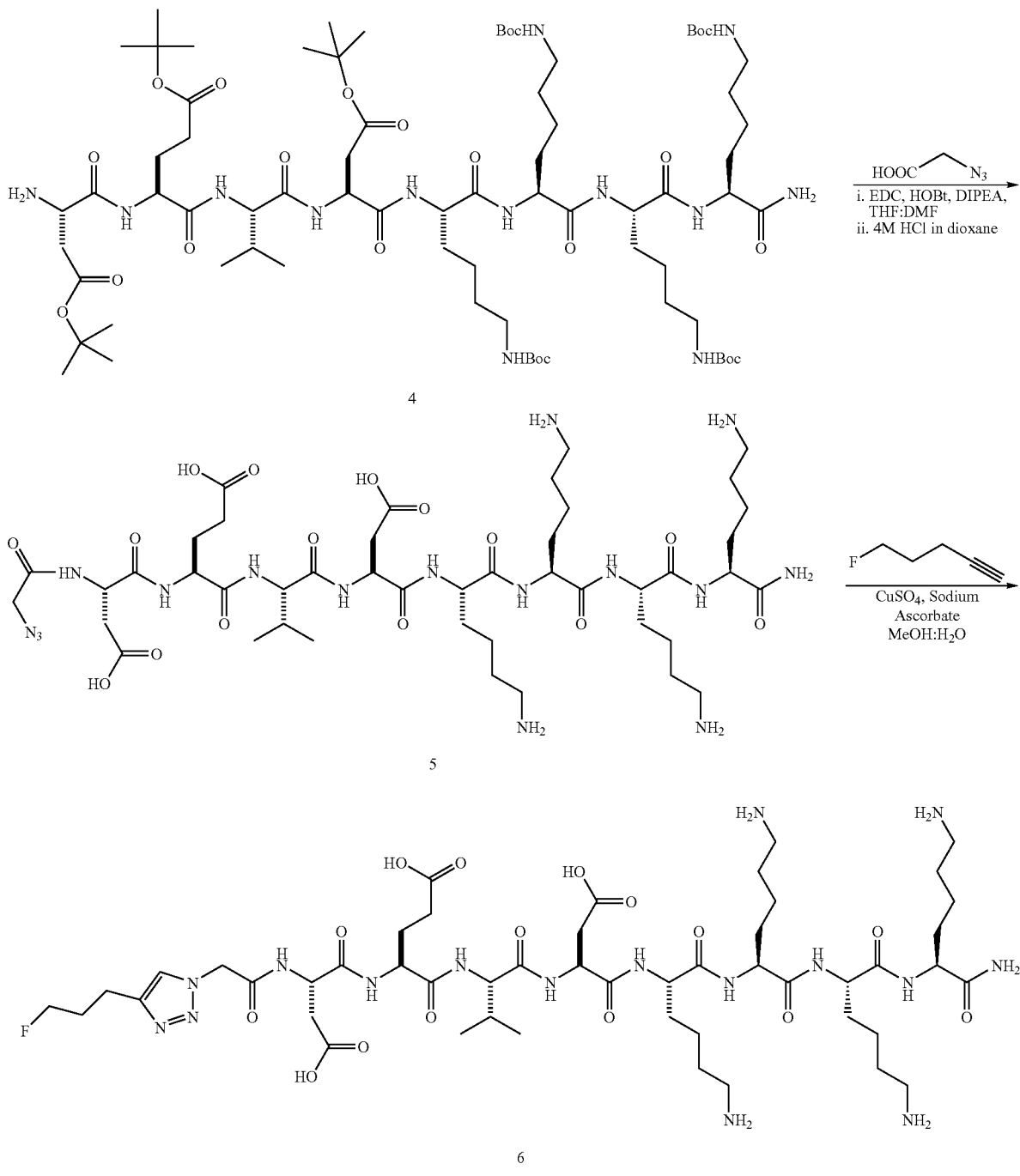

Scheme 1

Synthesis of 5

To a 10 mL round bottom flask containing 2-azidoacetic acid (50 mg, 0.48 mmol) in THF (2 mL) was treated with EDC (92 mg, 0.48 mmol), HOBt (65 mg, 0.48 mmol) at RT and stirred for 2 h. After 2 h, 4 (250 mg, 0.161 mmol) in DMF (2 mL), DIPEA (0.14 mL, 0.8 mmol) were added at room temperature and was stirred for 12 h. The reaction was concentrated, washed with EtOAc to get the product as a white solid. To a 10 mL round bottom flask containing the above product (250 mg, 0.152 mmol) at 0° C., was added 4M HCl in dioxane (3 mL). The temperature was raised to RT and stirred for 2.5 h. After the reaction is finished, dioxane was removed and the residue was dissolved in $H_2O$ and purified by HPLC to afford 5 (84 mg, 52%) as white solid. Mass Spec (lo-res): Calc'd for $C_{44}H_{78}N_{16}O_{15}$: 1070.6. found: 1071.6 (M+H).

Synthesis of 6

To a 5 mL round bottomed flask equipped with a magnetic stir bar containing MeOH:$H_2O$ (1:1, 1 mL) was placed 5 (14 mg, 0.013 mmol) and 5-fluoropent-1-yne (2 mg, 0.026 mmol). To this solution $CuSO_4$ (0.3 mg, 0.001 mmol), sodium ascorbate (0.5 g, 0.003 mmol) were added and stirred for 2 h. MeOH was evaporated and the residue was dissolved in $H_2O$ and purified by HPLC to afford product 6 (9 mg, 60%) as white solid. Mass Spec (lo-res): Calc'd for $C_{49}H_{85}FN_{16}O_{15}$: 1156.6. found: 1157.5 (M+H).

Example 2

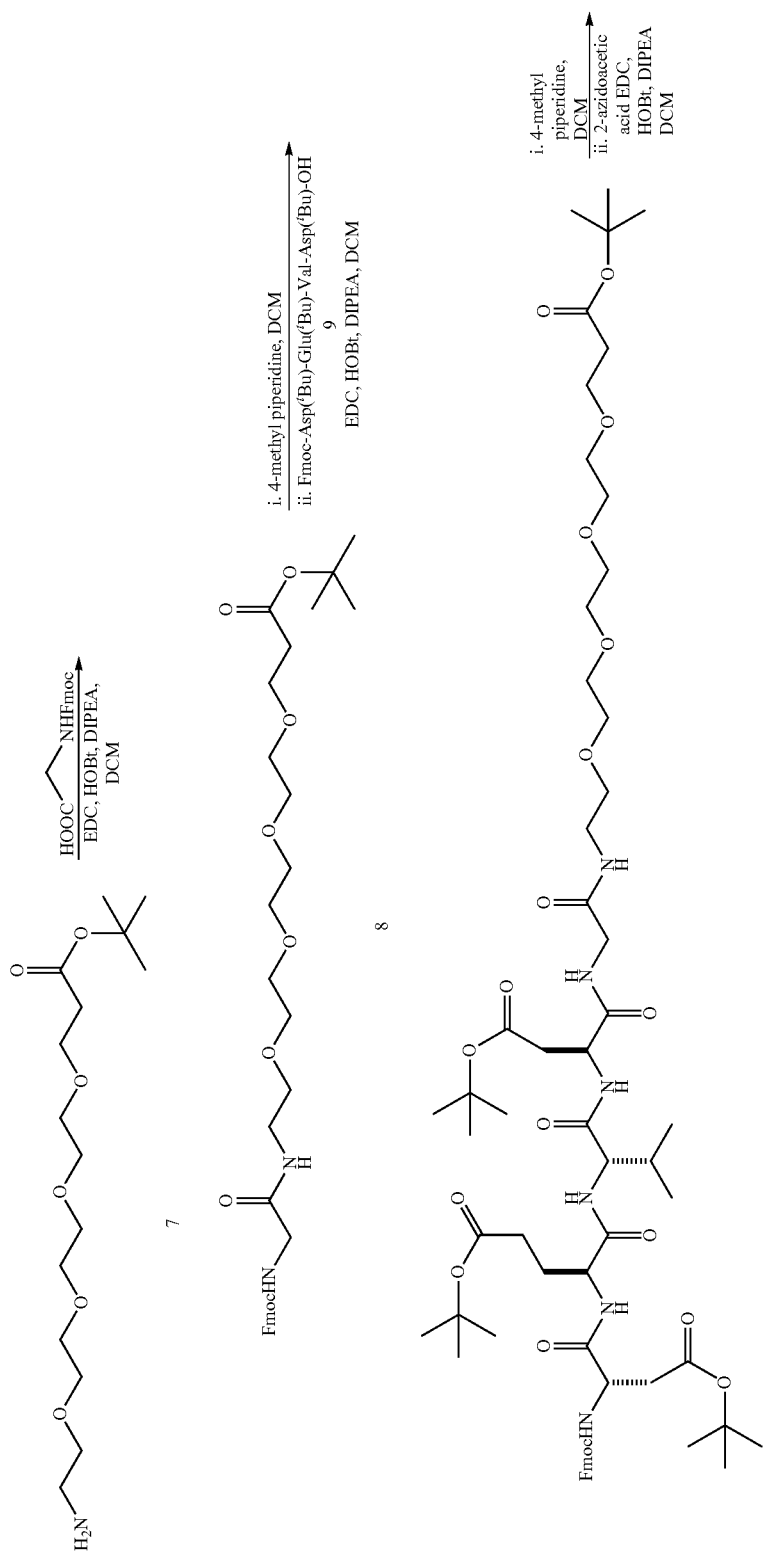
Scheme 2 ('Asp('Bu)-Glu('Bu)-Val-Asp('Bu)' disclosed as SEQ ID NO: 2)

-continued
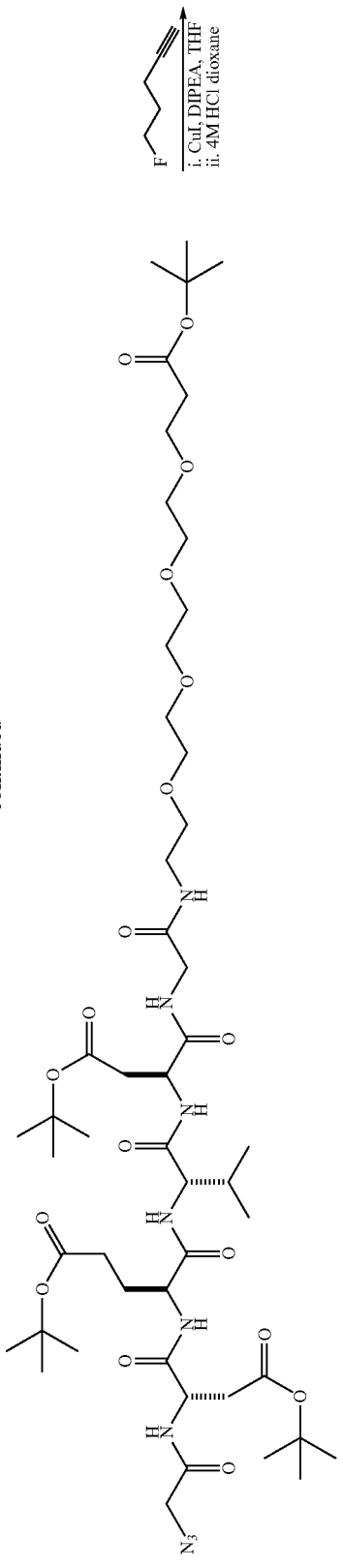
11
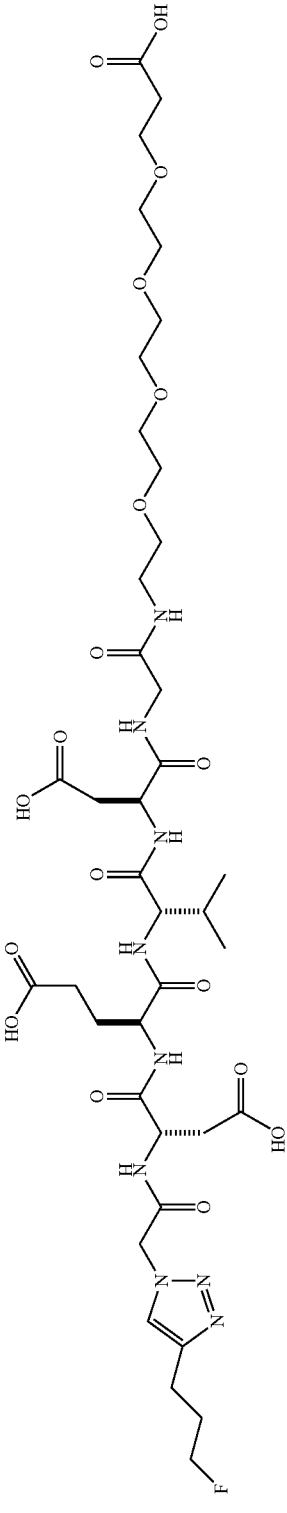
12

Synthesis of 8

To a 10 mL round bottom flask containing 2-(((9H-fluoren-9-yl)methoxy)carbonylamino)acetic acid (140 mg, 0.47 mmol) in DCM (3 mL) was treated with EDC (90 mg, 0.47 mmol), HOBt (60 mg, 0.47 mmol) at RT and stirred for 2 h. After 2 h, 7 (100 mg, 0.311 mmol) in DCM (1 mL), DIPEA (0.08 mL, 0.47 mmol) were added at room temperature and was stirred for 3 h. The reaction was concentrated on silica gel and purified over silica gel using EtOAc:Hexanes (1:1) as an eluent to afford 8 (178 mg, 95%) as white solid. Mass Spec (lo-res): Calc'd for $C_{32}H_{44}N_2O_9$: 600.3. found: 601.3 $(M+H)^+$.

Synthesis of 10

To a 10 mL round bottom flask containing 8 (178 mg, 0.297 mmol) in DCM (5 mL) was treated with 4-methyl piperidine (0.07 mL, 0.593 mmol) at RT and stirred for 2 h, solvent evaporated and washed the residue with 2-3 times with ether and used for the next step. To a 10 mL round bottom flask containing 9 (180 mg, 0.417 mmol) in DCM (3 mL) was treated with EDC (80 mg, 0.417 mmol), HOBt (60 mg, 0.417 mmol) at RT and stirred for 2 h. After 2 h, amine (105 mg, 0.278 mmol) in DCM (1 mL), DIPEA (0.07 mL, 0.417 mmol) were added at room temperature and was stirred for 12 h. The reaction was concentrated on silica gel and purified over silica gel using EtOAc:MeOH (95:5) as an eluent to afford 10 (119 mg, 35%) as white solid. Mass Spec (lo-res): Calc'd for $C_{62}H_{94}N_6O_{19}$: 1226.7. found: 1227.5 $(M+H)^+$.

Synthesis of 11

To a 10 mL round bottom flask containing 10 (119 mg, 0.1 mmol) in DCM (2 mL) was treated with 4-methyl piperidine (0.1 mL, 1.0 mmol) at RT and stirred for 2 h, solvent evaporated and washed the residue with 2-3 times with ether and used for the next step. To a 10 mL round bottom flask containing azido acid (20 mg, 0.189 mmol) in DCM (2 mL) was treated with EDC (40 mg, 0.189 mmol), HOBt (30 mg, 0.189 mmol) at RT and stirred for 2 h. After 2 h, amine (95 mg, 0.09 mmol) in DCM (1 mL), DIPEA (0.03 mL, 0.189 mmol) were added at room temperature and was stirred for 12 h. The reaction was concentrated on silica gel and purified over silica gel using MeOH:DCM (1:9) as an eluent to afford 11 (83 mg, 81%) as white solid. Mass Spec (lo-res): Calc'd for $C_{49}H_{85}N_9O_{18}$: 1087.6. found: 1088.5 $(M+H)^+$.

Synthesis of 12

To a 5 mL round bottomed flask equipped with a magnetic stir bar containing THF (1 mL) was placed 11 (41 mg, 0.038 mmol) and 5-fluoropent-1-yne (6 mg, 0.078 mmol). To this solution CuI (0.7 mg, 0.004 mmol), DIPEA (0.007 mL, 0.04 mmol) were added and stirred for 2 h. THF evaporated and used for the next step. To a 5 mL round bottom flask containing the above product (44 mg, 0.041 mmol) at 0° C., was added 4M HCl in dioxane (1 mL). The temperature was raised to RT and stirred for 2 h. After the reaction is finished, dioxane was removed and the residue was dissolved in $H_2O$ and purified by HPLC to afford product (15 mg, 39%) as white solid. Mass Spec (lo-res): Calc'd for $C_{38}H_{60}FN_9O_{18}$: 949.4. found: 950.4 $(M+H)^+$.

Example 3

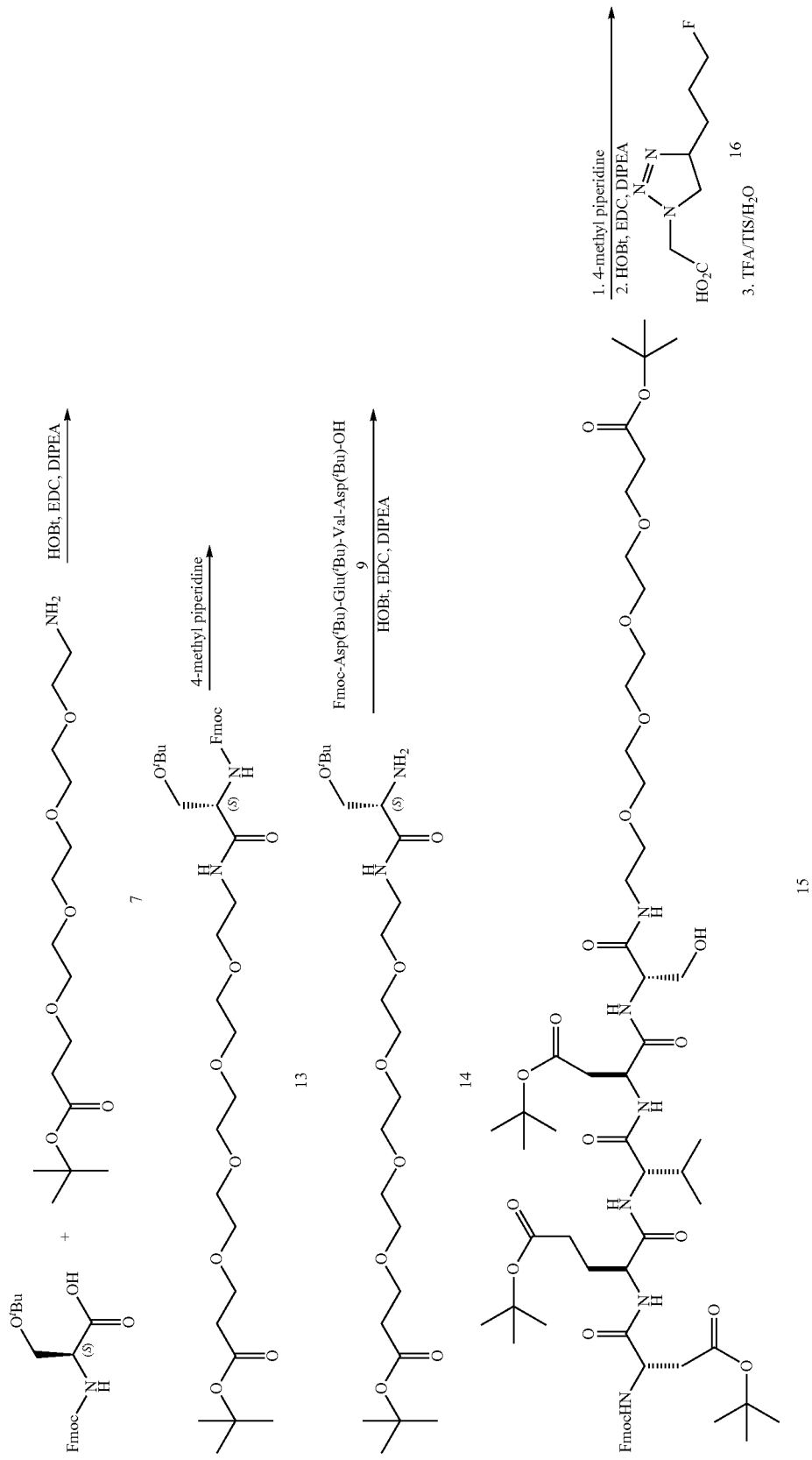

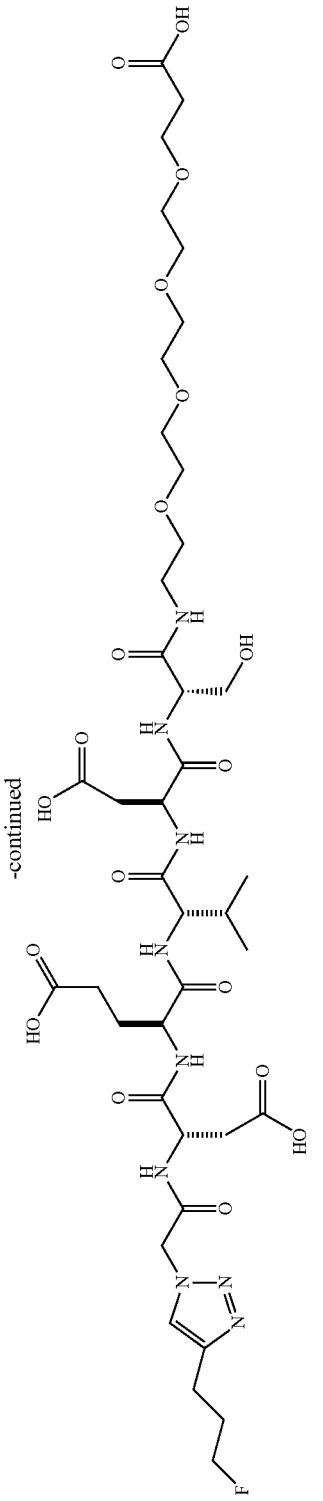
17

Synthesis of 13

To Fmoc-protected L-serine (286 mg, 0.747 mmol) in DCM (1 ml), was added HOBt (101 mg, 0.747 mmol) and EDC (143 mg, 0.747 mmol). After 20 min, $NH_2$-d(PEG)$_4$-O-$^t$Bu (200 mg, 0.622 mmol) and DIPEA (121 mg, 0.933 mmol) were added. The reaction was stirred at room temperature for 2 h and concentrated. The residue was then loaded on to a silica gel column (EtOAc:Hexanes=4:1) to afford a colorless oil 13 (310 mg, 0.451 mmol, 72.5% yield). Mass Spec (lo-res): Calc'd for $C_{37}H_{54}N_2O_{10}$: 686.4. found: 686.4 (M+H)$^+$).

Synthesis of 14

Compound 13 (310 mg, 0.451 mmol) was dissolved in 4-methyl piperidine (224 mg, 2.26 mmol) and DCM (2 ml). The mixture was stirred at room temperature for 2 h. The reaction was concentrated and co-evaporated with MeCN (×2) to remove all residue 4-methyl piperidine. The reaction mixture was purified on a silica gel column to afford 14 (200 mg, 0.430 mmol, 95% yield) as colorless oil (EtOAc, then MeOH:DCM=1:3). Mass Spec (lo-res): Calc'd for $C_{22}H_{44}N_2O_8$: 464.3. found: 465.3 (M+H)$^+$.

Synthesis of 15

To compound 9 (85 mg, 0.098 mmol) in solution of DMF (0.5 ml) was added HOBt (14.5 mg, 0.108 mmol) and EDC (20.6 mg, 0.108 mmol). The reaction was stirred at room temperature for 20 min. Then, 14 (50 mg, 0.108 mmol) was added with DIPEA (0.026 ml, 0.147 mmol) in DCM (0.500 ml). The resulting mixture was stirred at room temperature for another 2 h. The reaction was concentrated and purified by a silica gel column (MeOH:DCM=15:85) to afford 15 (111 mg, 0.085 mmol, 86% yield). Mass Spec (lo-res): Calc'd for $C_{63}H_{96}N_6O_{20}$: 1256.7. found: 1257.6 (M+H)$^+$.

Synthesis of 17

Compound 15 (111 mg, 0.085 mmol) was dissolved in DCM (3 ml). To the mixture was added 4-methyl piperidine (41.9 mg, 0.423 mmol). The resulting mixture was stirred at room temperature for 30 min. The mixture was concentrated in vacuo to afford the deprotected intermediate. To the solution of 2-(4-(3-fluoropropyl)-1H-1,2,3-triazol-1-yl)acetic acid 16 (27.4 mg, 0.147 mmol) in DMF (2 ml), was added HOBt (19.81 mg, 0.147 mmol) and EDC (28.1 mg, 0.147 mmol). After 20 min, to the mixture was added the deprotected intermediate (80 mg, 0.073 mmol) in solution of DMF (1 ml) and DIPEA (0.026 ml, 0.147 mmol). The reaction was stirred at room temperature for 15 h. The reaction was concentrated and dried in vacuo again. To the residue was added TFA:TIS:Water (ratio 95:2.5:2.5, 10 ml). After 30 min, the reaction was concentrated, and dissolved in water, filtered (0.45 um) and purified by HPLC to afford product (20 mg, 0.020 mmol, 27.8% yield). $^1$H NMR (D$_2$O, 400 MHz), δ: 8.38 (b, 1H), 8.01 (b, 1H), 7.84 (b, 1H), 7.65 (s, 1H), 5.12 (d, 2H, J=2.0 Hz), 4.55-4.50 (m, 2H), 4.40 (t, 1H, J=5.2 Hz), 4.28 (t, 1H, J=5.2 Hz), 4.25-4.16 (m, 2H), 3.88-3.84 (m, 1H), 3.70-3.58 (m, 4H), 3.48 (m, 13H), 3.43 (t, 2H, J=6.0 Hz), 3.26-3.20 (m, 2H), 2.82-2.62 (m, 6H), 2.46 (t, 2H, J=6.0 Hz), 2.27-2.18 (m, 2H), 2.00-1.74 (m, 4H), 0.70-0.67 (m, 6H). $^{19}$F NMR (D$_2$O, 376 MHz), δ: −76.55 (TFA, —CF$_3$), −219.2 (tt, J=47 Hz, 27 Hz). Mass Spec (lo-res): Calc'd for $C_{39}H_{62}FN_9O_{19}$: 979.4. found: 980.3 (M+H)$^+$.

Example 4

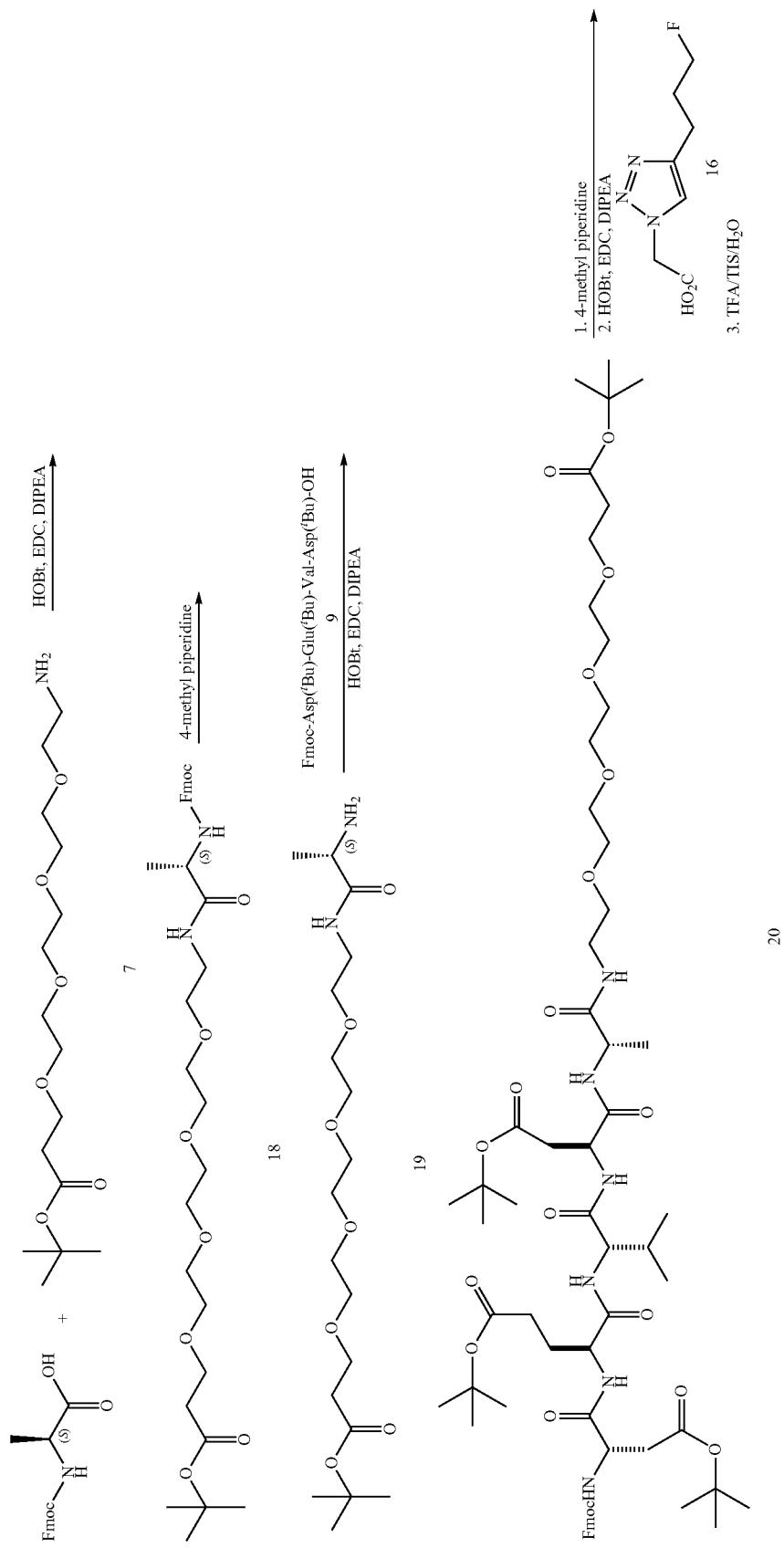

-continued
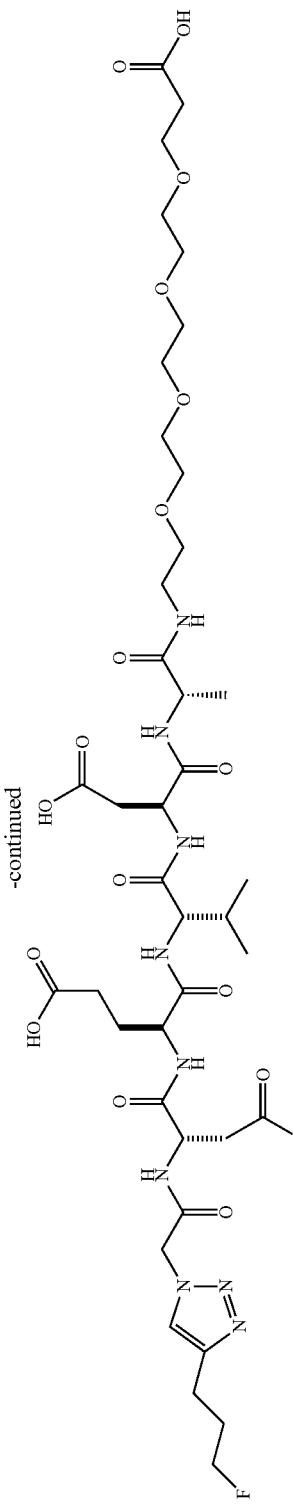
21

Synthesis of 18

To Fmoc-protected L-alanine (246 mg, 0.747 mmol) in DCM (1 ml), was added HOBt (101 mg, 0.747 mmol) and EDC (143 mg, 0.747 mmol). The reaction was stirred at room temperature for 20 min. To the reaction was added $NH_2$-d$(PEG)_4$-O$^t$Bu (200 mg, 0.622 mmol) and DIPEA (121 mg, 0.933 mmol). The reaction was stirred for another 2 h. Then the mixture was concentrated and purified on a silica gel column (EtOAc:Hexanes=4:1) to afford 18 (240 mg, 0.390 mmol, 62.7% yield). Mass Spec (lo-res): Calc'd for $C_{33}H_{46}N_2O_9$: 614.3. found: 615.3 (M+H)$^+$.

Synthesis of 19

Compound 18 (240 mg, 0.390 mmol) was dissolved in DCM, 4-methyl piperidine (194 mg, 1.95 mmol) was added at room temperature. The reaction was stirred overnight. The reaction was concentrated and purified on a silica gel column to afford 19 (110 mg, 0.280 mmol, 71.8% yield) as a colorless oil (EtOAc, then MeOH:DCM=1:3). Mass Spec (lo-res): Calc'd for $C_{18}H_{36}N_2O_7$: 392.3. found: 393.2 (M+H)$^+$.

Synthesis of 20

To compound 9 (100 mg, 0.116 mmol) in solution of DMF (1 ml), was added HOBt (17.2 mg, 0.127 mmol) and EDC (24.4 mg, 0.127 mmol). The reaction was stirred at rt for 20 min. Compound 19 (50 mg, 0.127 mmol) was added in DCM (1.0 ml) followed by DIPEA (22.5 mg, 0.174 mmol). The reaction was stirred at room temperature overnight. The resulting mixture was then concentrated and purified on a silica gel column (MeOH:DCM=1:9) to afford 20 (100 mg, 0.081 mmol, 69.6% yield). Mass Spec (lo-res): Calc'd for $C_{59}H_{88}N_6O_{19}$: 1184.6. found: 1185.5 (M+H)$^+$.

Synthesis of 21

Compound 20 (100 mg, 0.081 mmol) was dissolved in DCM (1 ml). To the solution, was added piperidine (343 mg, 4.03 mmol). After 2 h, the reaction was concentrated in vacuo to afford the deprotected intermediate. To the solution of 2-(4-(3-fluoropropyl)-1H-1,2,3-triazol-1-yl)acetic acid (29.4 mg, 0.157 mmol) in DCM (1 ml), was added HOBt (21.2 mg, 0.157 mmol) and EDC (30.1 mg, 0.157 mmol). The mixture was stirred at room temperature for 20 min. To the mixture was added the deprotected intermediate (80 mg, 0.078 mmol) in solution of DMF (1.00 ml) and DIPEA (0.027 ml, 0.157 mmol). The reaction was stirred at room temperature overnight. The reaction mixture was concentrated in vacuo. To the residue was added TFA:TIS:Water (ratio 95:2.5:2.5, 10 ml). After 30 min, the reaction was concentrated, and dissolved in water, filtered (0.45 um) and purified by HPLC to afford 21 (30 mg, 0.031 mmol, 39.7% yield). $^1$H NMR (D$_2$O, 400 MHz), δ: 7.98 (b, 1H), 7.82 (b, 1H), 7.65 (s, 1H), 5.14 (d, 2H, J=2.4 Hz), 4.57-4.50 (m, 2H), 4.40 (t, 1H, J=5.4 Hz), 4.28 (t, 1H, J=5.4 Hz), 4.20 (m, 1H), 4.08 (m, 1H), 3.86-3.82 (m, 1H), 3.58 (t, 2H, J=6.4 Hz), 3.48 (m, 13H), 3.41 (t, 2H, J=5.6 Hz), 3.23-3.17 (m, 2H), 2.82-2.58 (m, 6H), 2.47 (t, 2H, J=6.0 Hz), 2.27-2.20 (m, 2H), 2.00-1.74 (m, 5H), 1.17 (d, 3H, J=7.2 Hz), 0.69-0.67 (m, 6H). $^{19}$F NMR (D$_2$O, 376 MHz), δ: −76.55 (TFA, —CF$_3$), −219.9 (tt, J=47 Hz, 27 Hz). Mass Spec (lo-res): Calc'd for $C_{39}H_{62}FN_9O_{18}$, calc'd: 963.4. found: 964.3 (M+H)$^+$.

The compound of Example 4 can also be synthesized as follows:

Synthesis of Precursor for Radiolabeled Compound 21

Scheme 5

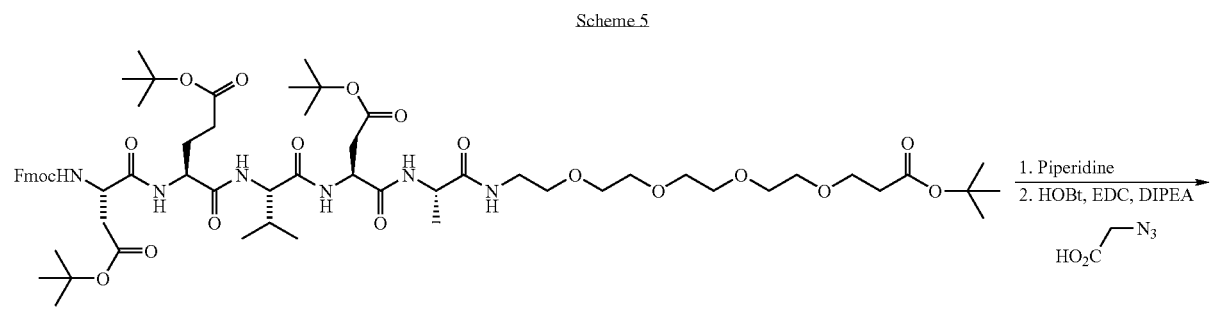

20

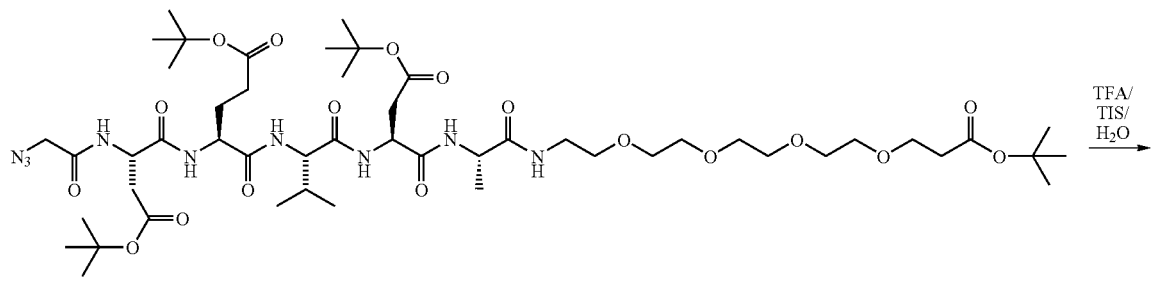

22

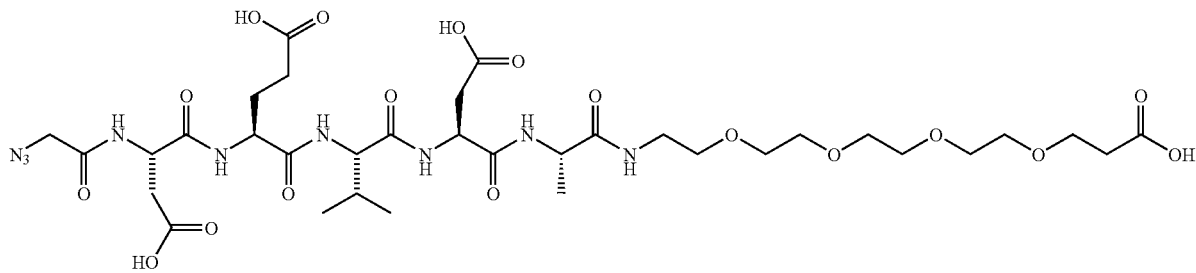

23

Synthesis of 22

Compound 20 (95 mg, 0.077 mmol) was dissolved in DCM (1 mL). To the solution, was added piperidine (326 mg, 3.83 mmol). After 2 h, the reaction was concentrated in vacuo to afford the deprotected intermediate (78 mg). To the solution of 2-azido acetic acid (258 mg, 6% wt solution in DCM, 0.153 mmol) in DCM (1 mL), was added HOBt (20.7 mg, 0.153 mmol) and EDC (29.3 mg, 0.153 mmol). The mixture was stirred at room temperature for 20 min. To the mixture was added the deprotected intermediate (78 mg, 0.077 mmol) in solution of DMF (1.00 ml) and DIPEA (0.027 ml, 0.153 mmol). The reaction was stirred at room temperature for 30 min. The mixture was concentrated in vacuo and diluted with water (15 mL). The white solid precipitate was filtered and dried to afford 22 (71 mg, 0.064 mmol, 84% yield). Mass Spec (lo-res): Calc'd for $C_{50}H_{87}N_9O_{15}$, calc'd: 1101.6 found: 1102.5 (M+H)$^+$.

Synthesis of 23

Compound 22 (120 mg, 0.109 mmol) was added to the mixture of TFA:TIS:Water (ratio 95:2.5:2.5, 1.1 mL). After stirred at rt for 2 h, the reaction was concentrated, and dissolved in water (5 mL), filtered (0.45 um) and purified by HPLC (Phenomenex C-18 LUNA, gradience 10% MeCN in Water to 40% MeCN in water, 0.05% wt of TFA in both eluents) to afford 23 (80 mg, 0.091 mmol, 84% yield). $^1$H NMR (D$_2$O, 400 MHz), δ: 4.60-4.50 (m, 2H), 4.25-4.20 (m, 1H), 4.10-4.06 (m, 1H), 3.88 (s, 2H), 3.60 (t, 2H, J=6.0 Hz), 3.48 (m, 13H), 3.43 (t, 2H, J=6.0 Hz), 3.22-3.18 (m, 2H), 2.82-2.60 (m, 4H), 2.46 (t, 2H, J=6.0 Hz), 2.30-2.25 (m, 2H), 2.00-1.74 (m, 3H), 1.18 (d, J=7.2 Hz, 3H), 0.74 (t, J=6.8 Hz, 6H). $^{13}$C NMR (D$_2$O, 100 MHz), δ: 176.9, 176.0, 174.6, 173.8, 173.8, 173.1, 173.0, 172.1, 171.5, 170.4, 69.5, 69.5, 69.4, 69.4, 69.4, 69.3, 68.6, 66.0, 59.7, 53.0, 51.5, 49.9, 49.8, 38.8, 35.1, 35.0, 34.1, 29.8, 29.7, 25.6, 18.1, 17.7, 16.6. Mass Spec (lo-res): Calc'd for $C_{34}H_{55}N_9O_{18}$, calc'd: 877.4. found: 878.2 (M+H)$^+$.

Example 5

Scheme 6

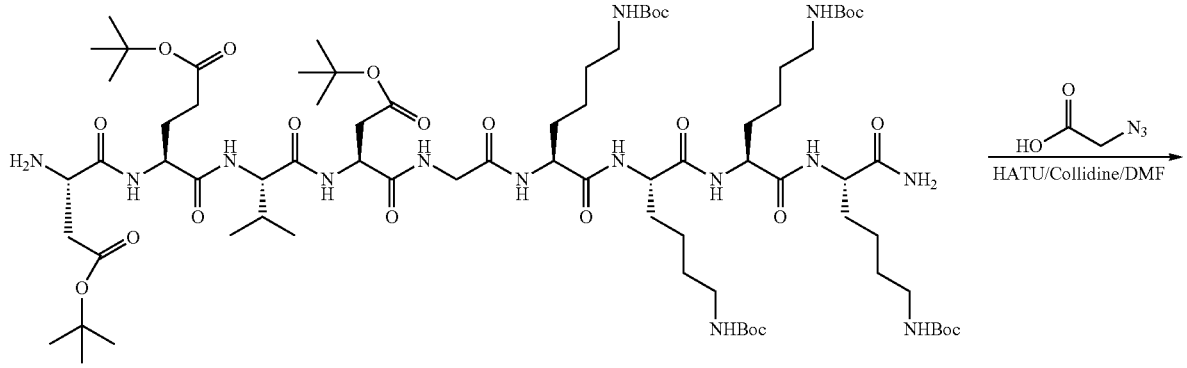

24

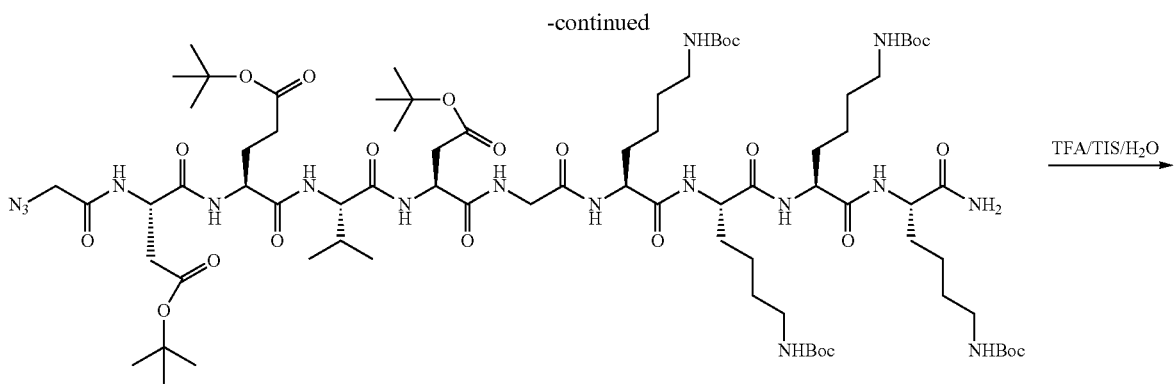

25

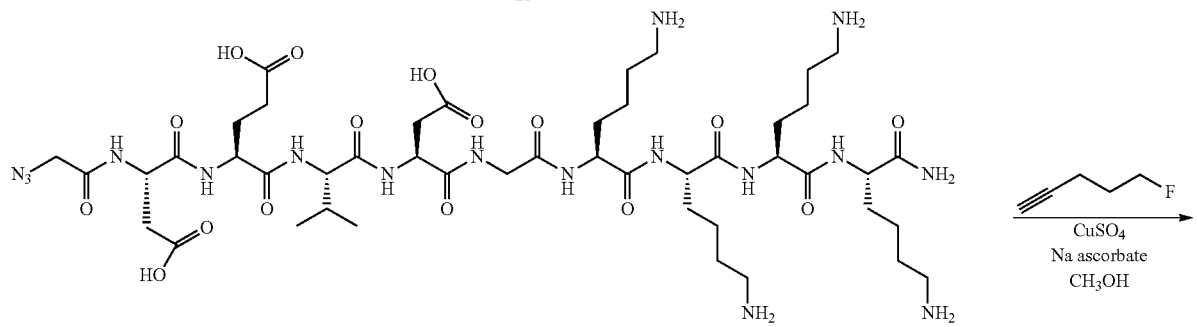

26

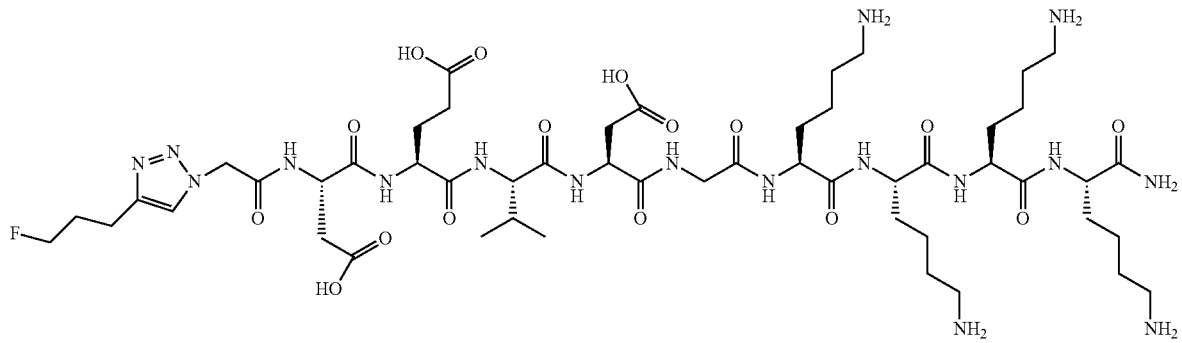

27

Synthesis of 25

To a round bottom flask containing azido acetic acid (1.185 g, 0.293 mmol, 2.5%) in DMF (5 mL) at room temperature, was added HATU (67 mg, 0.176 mmol) and 2,4,6-collidine (35.5 mg, 0.293 mmol). The reaction was stirred at room temperature for 2 h. Then compound 24 (220 mg, 0.117 mmol) was added to the mixture. The reaction was stirred at room temperature overnight until LC/MS indicates the completion of the reaction. The mixture was concentrated in vacuo and then washed with EtOH (5 mL×3) to afford the product (160 mg, 80% yield). Mass Spec (lo-res): Calc'd for $C_{78}H_{137}N17O24$: 1696.00. found: 1696.9 (M+H)$^+$.

Synthesis of 26

Compound 25 (60 mg, 0.035 mmol) was dissolved in a cocktail solution of TFA:TIS:H$_2$O=95:2.5:2.5 (5 mL) and stirred for 2 h at room temperature. The reaction was concentrated, redissolved in water, filtered, purified on semi-prep HPLC, and lyophilized to afford the product (20 mg, 70% yield). $^1$H NMR (400 MHz, D$_2$O) δ 0.74-0.76 (dd, 6H, J=6.8 Hz), 1.24-1.28 (m, 9H), 1.46-1.53 (m, 10H), 1.55-1.67 (m, 7H), 1.78-1.82 (m, 1H), 1.87-1.93 (m, 1H), 2.20-2.29 (m, 1H), 2.64-2.74 (m, 3H), 2.77-2.84 (m, 10H), 3.74 (s, 2H), 3.89-3.92 (m, 3H), 4.04-4.17 (m, 4H), 4.24-4.28 (m, 1H), 4.49-4.53 (m, 1H). Mass Spec (lo-res): Calc'd for $C_{46}H_{81}N_{17}O_{16}$: 1127.60. found: 1128.3 (M+H)$^+$.

Synthesis of 27

To a round bottom flask containing compound 26 (14 mg, 0.012 mmol) in MeOH (0.8 mL), was added CuSO$_4$ solution (0.012 mL, 0.1 M), sodium ascorbate solution (5 uL, 0.5 M), and a drop of fluoropentyne. The reaction was stirred at room temperature for 2 hr until LC/MS indicates the completion of the reaction. The reaction was concentrated, redissolved in water, filtered, purified on semi-prep HPLC, and lyophilized to afford the product (10 mg, 66% yield). $^1$H NMR (400 MHz, CD$_3$OD) δ 0.82-0.95 (dd, 6H), 1.43-1.55 (m, 9H), 1.65-1.90 (m, 17H), 2.00-2.11 (m, 4H), 2.40-2.44 (m, 1H), 2.81-2.97 (m, 13H), 3.75-3.80 (d, 1H), 3.89 (s, 1H), 3.93-3.97 (t, 1H), 4.26-4.33 (m, 6H), 4.41-4.45 (m, 2H), 4.47-4.51 (q, 1H), 4.52-4.55 (t, 1H), 4.69-4.72 (t, 1H), 5.19-5.31 (q, 1H, J=13.6 Hz), 7.83 (s, 1H). $^{19}$F NMR (CD$_3$OD, 376 MHz), δ: −76.9 (TFA, —CF$_3$), −222.05 (tt, J=47.8 Hz, 25.6 Hz). Mass Spec (lo-res): Calc'd for C$_{51}$H$_{88}$FN$_{17}$O$_{16}$: 1213.66. found: 1214.3 (M+H)$^+$.
Example 6
Scheme 7
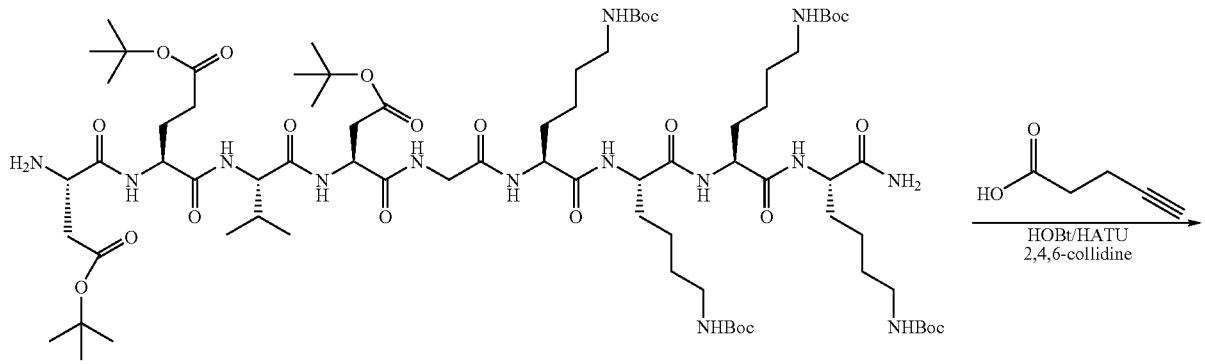
24
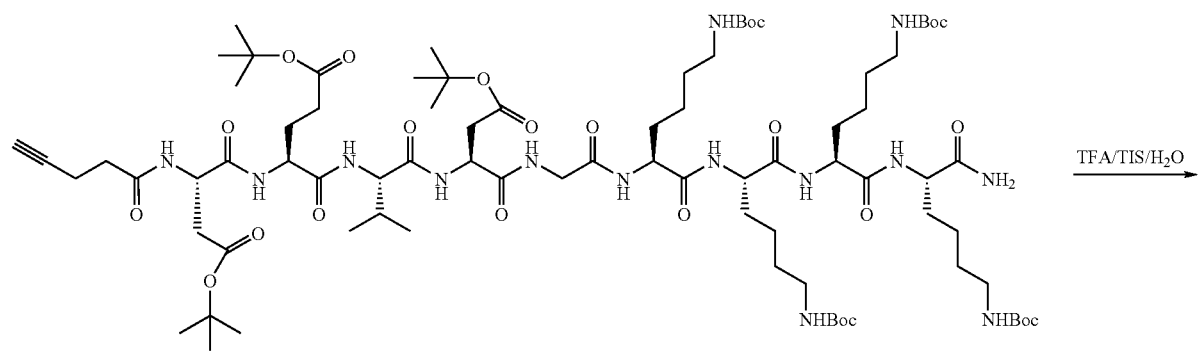
28
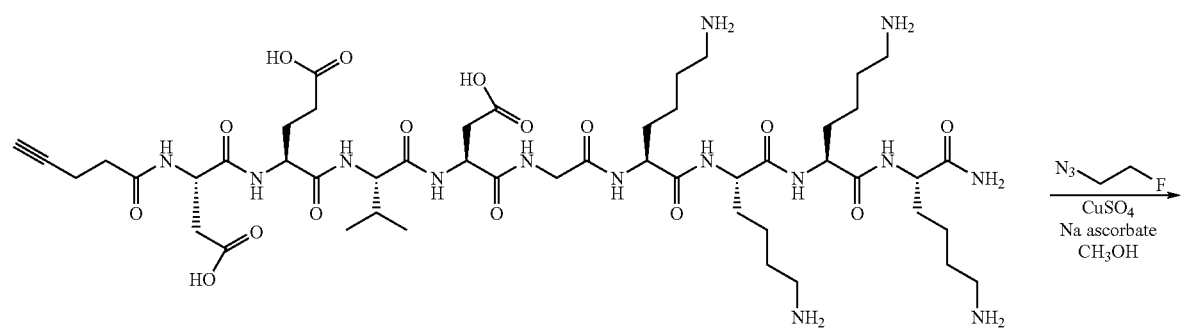
29

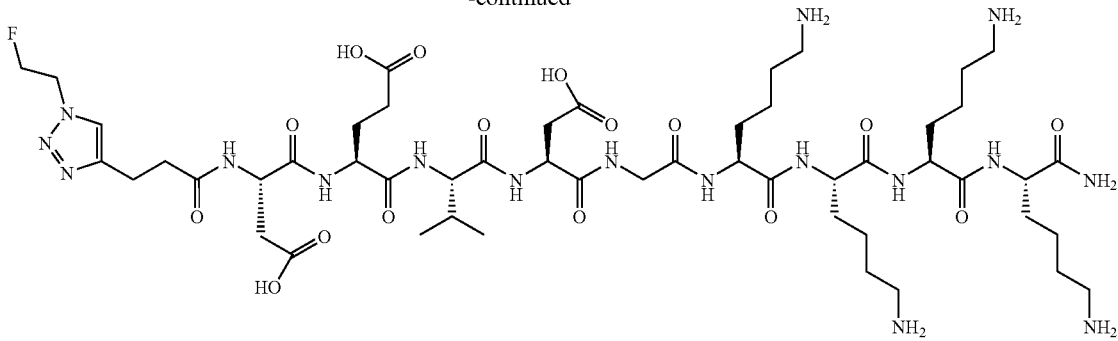

30

Synthesis of 28

To a round bottom flask containing pent-4-ynoic acid (15.68 mg, 0.16 mmol) in DMF (5 mL) at room temperature, was added HATU (61 mg, 0.16 mmol) and 2,4,6-collidine (32 mg, 0.266 mmol). The reaction was stirred at room temperature for 45 min. Then compound 24 (200 mg, 0.107 mmol) was added to the mixture. The reaction was stirred at room temperature for 3 hr and LC/MS demonstrated the completion of the reaction. The mixture was concentrated in vacuo and then washed with water (5 mL×3) and ether (5 mL×3) to afford the product (151 mg, 84% Yield). Mass Spec (lo-res): Calc'd for $C_{81}H_{140}N_{14}O_{24}$: 1693.02. found: 1594.9 (M+H-Boc)$^+$.

Synthesis of 29

Compound 28 (38 mg, 0.022 mmol) was dissolved in a cocktail solution of TFA:TIS:H$_2$O=95:2.5:2.5 (2 mL) and stirred for 2 h at room temperature. The reaction was concentrated, redissolved in water, filtered, purified on semi-prep HPLC, and lyophilized to afford the product (24 mg, 94% yield). $^1$H NMR (400 MHz, D$_2$O) δ 0.84-0.86 (t, 6H, J=6.0 Hz), 1.35-1.37 (m, 8H), 1.56-1.73 (m, 17H), 1.89-1.92 (m, 1H), 1.98-2.02 (m, 2H), 2.29 (s, 1H), 2.33-2.43 (m, 6H), 2.73-2.84 (m, 3H), 2.90-2.93 (m, 10H), 3.85 (s, 1H), 4.00-4.02 (d, 1H), 4.15-4.28 (m, 3H), 4.36-4.39 (m, 1H), 4.58-4.60 (m, 2H). Mass Spec (lo-res): Calc'd for $C_{49}H_{84}N_{14}O_{16}$: 1124.62. found: 1125.4 (M+H)$^+$.

Synthesis of 30

To a vial was added compound 29 (15 mg, 0.013 mmol) and azidoethyl fluoride in DMF followed by CuSO$_4$ solution (8 μL, 0.1 M) and sodium ascorbate solution (8 μL, 0.2 M). After 2 hrs, LC/MS indicated that the starting material was consumed. The solvent was then evaporated. The residue was dissolved in CAN, purified using semi-prep HPLC, and lyophilized to afford 12 mg (75% yield) of product. $^1$H NMR (400 MHz, CD$_3$OD) δ 0.87-0.94 (dd, 6H), 1.44-1.55 (m, 8H), 1.68-1.88 (m, 17H), 2.03-2.09 (m, 1H), 2.19-2.25 (m, 2H), 2.38-2.42 (m, 1H), 2.50-2.58 (m, 1H), 2.62-2.68 (t, 3H), 2.78-2.86 (m, 3H), 2.90-2.95 (m, 10H), 3.09-3.18 (m, 2H), 3.78-3.82 (d, 1H), 3.90-3.94 (m, 2H), 4.27-4.39 (m, 3H), 4.39-4.50 (m, 2H), 4.55-4.62 (m, 1H), 4.63-4.68 (m, 1H), 4.71-4.76 (m, 1H), 7.83 (s, 1H). $^{19}$F NMR (CD$_3$OD, 376 MHz), δ: −76.9 (TFA, —CF$_3$), −224.49 (tt, J=47.4 Hz, 26.7 Hz). Mass Spec (lo-res): Calc'd for $C_{51}H_{88}FN_{17}O_{16}$: 1213.66. found: 1214.5 (M+H)$^+$.

Example 7

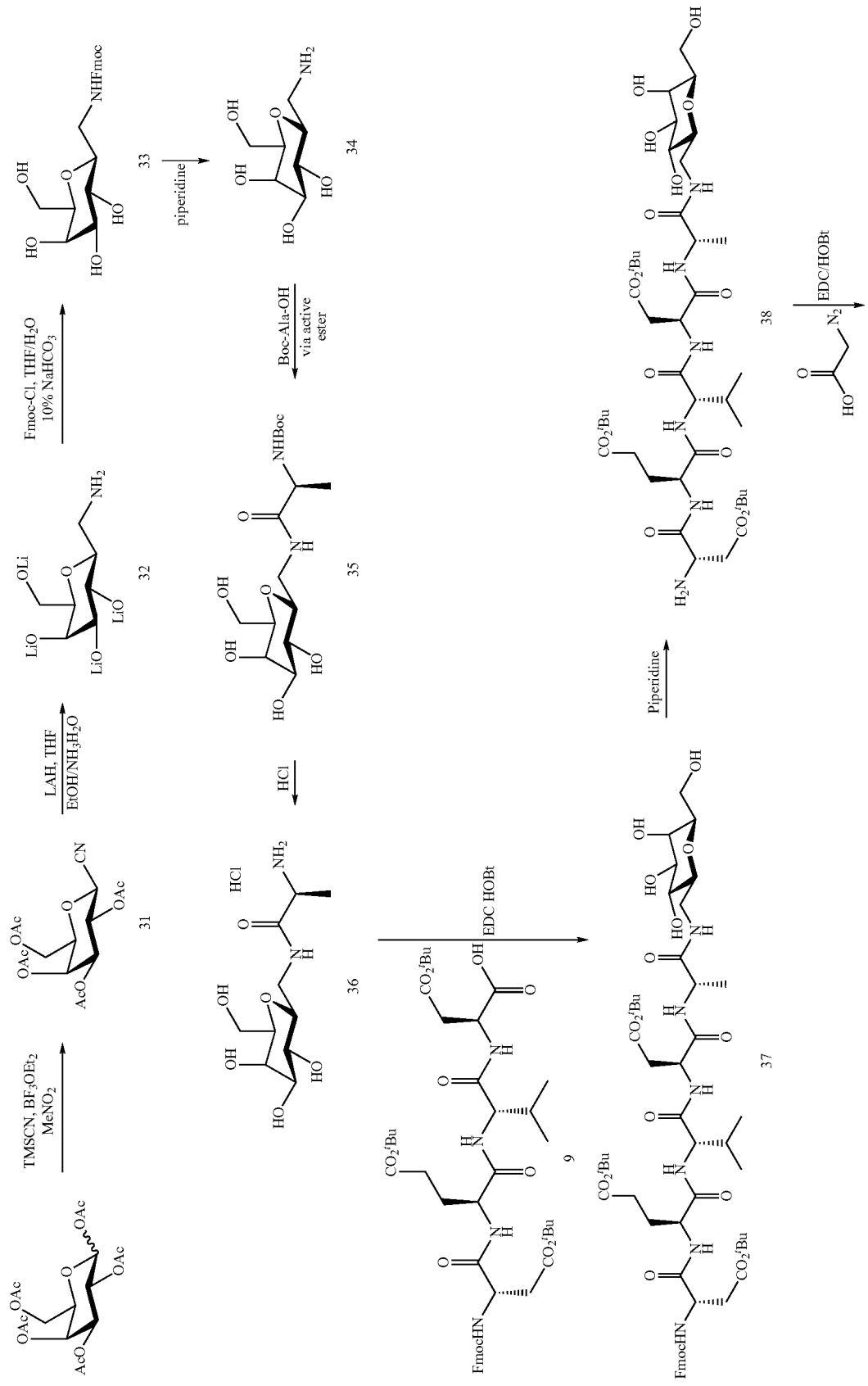

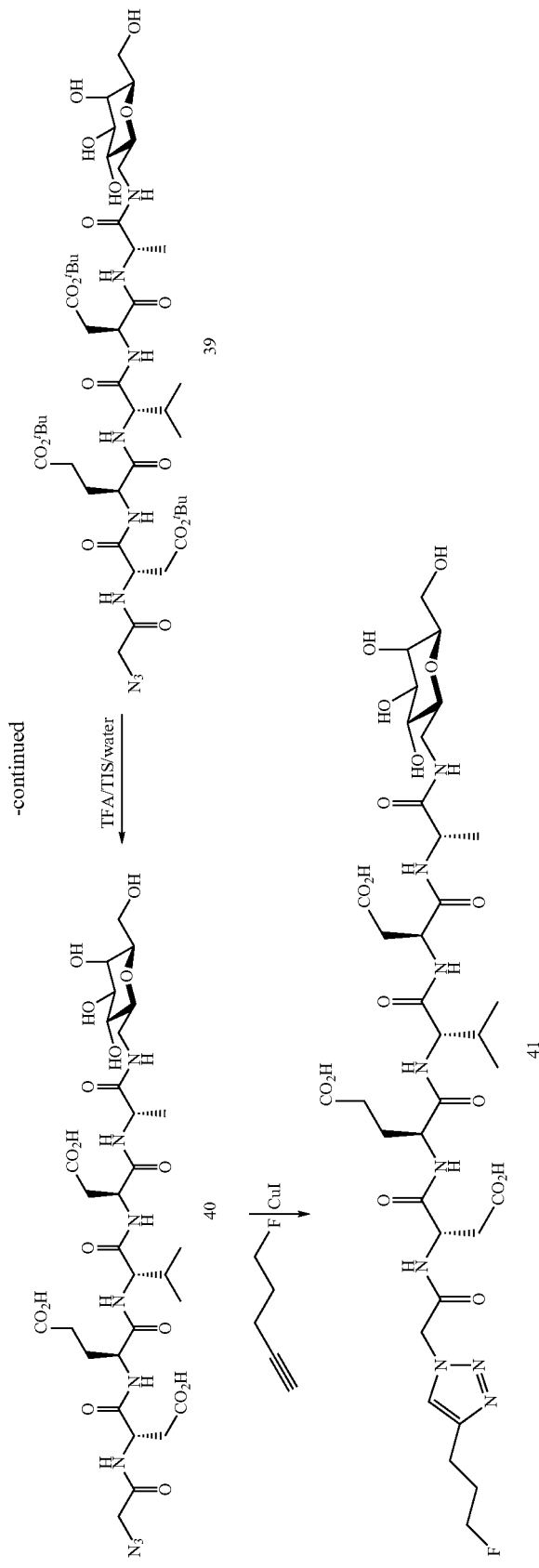

Synthesis of 31 beta-D-Galactose Pentaacetate (50 g, 0.12 mol) in nitromethane (200 mL) was treated with trimethylsilyl cyanide (15 mL, 0.21 mol) and $BF_3.OEt_2$ (3 mL, 0.05 mol) at room temperature. The reaction mixture was stirred at room temperature for 1 h. Additional amount of TMSCN (15 mL, 0.21 mol) and $BF_3.OEt_2$ (3 mL, 0.05 mol) were added and stirred at room temperature for 1 h. Volatiles were removed under vacuo and the crude reaction mixture was redissolved in ethyl acetate (1 L), washed with $NaHCO_3$ solution (2×250 mL), water (1×500 mL), brine (1×250 mL) and dried over $Na_2SO_4$. Organic layer was concentrated under vacuo to reduce half of its volume and recrystallized by cooling to 0° C. Pale yellow solid was filtered and washed with EtOAc, dried under vacuo to afford of 31 (32 g, 0.08 mol, 75% yield). $^1H$ NMR ($CDCl_3$, 400 MHz), δ: 5.54 (t, 1H), 5.43 (dd, 1H, J=3.2 Hz, 1.2 Hz), 5.01 (dd, 1H, J=10 Hz, 3.2 Hz), 4.30 (d, 1H, J=10 Hz), 4.12 (d, 2H, J=6.4 Hz), 3.95 (td, 1H, J=1.2 Hz, 6.4 Hz), 2.19-2.00 (4s, 12H, acetyl-$CH_3$). Mass Spec (lo-res): Calc'd for $C_{15}H_{19}NO_9$: 357.11. found: 380.1 $(M+Na)^+$.

Synthesis of 32

Lithium aluminum hydride (17.7 g, 444 mmol) was added to THF (anhydrous, 75 ml) to form a suspension. Compound 31 (39.7 g, 111 mmol) in anhydrous THF (420 ml) was added to the suspension through an addition funnel at 0° C. to in 2 hours to form a light yellow suspension. The mixture was allowed to room temperature and stirred over night. To the mixture stirred in an ice bath, was added EtOH 80 mL drop wise and ammonium hydroxide solution (aq, 28-30%) 86 mL. The mixture was stirred at room temperature for 2 hours. The result mixture was filtered and washed with water (25 mL×3) and diethyl eterh (30 mL×3). The cake was dried over $P_2O_5$ under vacuo for two days to afford a white solid 32 with inorganic salt and small amount of water (128 g, ca. purity 16%, 95% yield) to be carried out to next step without purification. The product can be characterized by NMR after filtration of its $D_2O$ suspension. $^1H$ NMR ($D_2O$, 400 MHz), δ: 3.74 (d, 1H, J=3.6 Hz), 3.56-3.51 (m, 2H), 3.44-3.29 (m, 2H), 3.29 (t, 1H, J=9.6 Hz), 3.05 (m, 1H), 2.83 (m, 1H), 2.51 (dd, 1H, J=13.6 Hz, J=8.0 Hz). Mass Spec (lo-res): Calc'd for $C_7H_{15}NO_5$: 193.10. found: 194.1 $(M+H)^+$.

Synthesis of 33

Compound 32 (132 g, 109 mmol, 16% purity) was dissolved in an aqueous solution of NaHCO3 (10% wt, 300 mL). To the mixture at the ice bath temperature, was added Fmoc-Cl (26.5 g, 93 mmol) in THF (150 mL) drop wise. Addition time was 1.5 h. After addition, LCMS indicates completion of the reaction. HCl (conc. 37%, 90 mL) was added drop wise to quench the reaction until pH reached 3-4. The suspension was concentrated under vacuum to remove THF. The resulting sticky suspension was washed with hot THF (250 mL×5) with ultrasound. The combined liquid phases were concentrated under vacuo to afford a white solid crude product (90 g). The crude product was triturated with hot EtOAc (400 mL) and washed with water (50 mL) and diethyl ether (50 mL×2) to afford the desired product as a white solid 33 (40 g, 106 mmol, 97% yield) after overnight drying under vacuo with $P_2O_5$. $^1H$ NMR (DMSO, 400 MHz), δ: 7.89 (d, 2H, J=7.2 Hz), 7.70 (d, 2H, J=7.2 Hz), 7.42 (t, 2H, J=7.2 Hz), 7.33 (t, 2H, J=7.2 Hz), 7.24 (t, 1H, J=4.4 Hz), 4.85 (b, 1H), 4.69 (b, 1H), 4.49 (b, 1H), 4.25-3.72 (m, 3H), 3.64 (b, 1H), 3.60-3.41 (m, 3H), 3.31-3.26 (m, 4H), 3.02 (t, 1H, J=7.6 Hz), 2.91 (m, 1H). Mass Spec (lo-res): Calc'd for $C_{22}H_{25}NO_7$: 415.16. found: 416.0 $(M+H)^+$.

Synthesis of 34

Compound 33 (1.65 g, 3.97 mmol) was dissolved in DCM (20 ml). To the solution, was added piperidine (8 mL, 79 mmol). After stirred at rt for 3 h, the reaction was concentrated in vacuo, co-evaporate with MeCN and lypholized overnight to afford a brown solid 34 (1.1 g, 4.0 mmol, purity 70% (contains 1 eq of piperidine carbonate) 100% yield). Mass Spec (lo-res): Calc'd for $C_7H_{15}NO_5$, calc'd: 193.1. found: 194.2 $(M+H)^+$.

Synthesis of 35

To compound 34 (300 mg, 1.087 mmol) and N-Boc-L-Alanine-activated ester (622 mg, 2.17 mmol) in solution of DMF (2 ml), was added DIPEA (0.568 mL, 3.26 mmol). The reaction was stirred at rt for 2 h. The mixture was diluted with diethyl ether (50 mL). The insoluble residue was isolated and dissolved in water and purified on RP-HPLC to provide 35 (80 mg, 0.22 mmol, 20% yield). Mass Spec (lo-res): Calc'd for $C_{15}H_{28}N_2O_8$: 364.2. found: 365.1 $(M+H)^+$.

Synthesis of 36

To compound 35 (80 mg, 0.22 mmol), was added HCl (4 M solution in dioxane, 2 mL). The reaction was stirred at rt for 3 h. The reaction was concentrated and dissolved in water and lypholized to afford a yellow solid 36 (32 mg, 0.121 mmol, 55% yield). Mass Spec (lo-res): Calc'd for $C_{10}H_{20}N_2O_6$: 264.1. found: 265.2 $(M+H)^+$.

Synthesis of 37

Compound 9 (103 mg, 0.119 mmol), HOBt (15.3 mg, 0.114 mmol) and EDC (21.8 mg, 0.114 mmol) was dissolved in DMF (0.5 mL). The reaction mixture was stirred at rt for 30 min. Compound 36 (30 mg, 0.116 mmol) and DIPEA (0.02 mL, 0.114 mmol) in solution of DMF (0.5 mL) was added. The reaction was stirred at rt for 5 h. To the mixture was added water (20 mL). White precipitates were collected via filtration to afford 37 (120 mg, 0.112 mmol, 98%). Mass Spec (lo-res): Calc'd for $C_{55}H_{80}N_6O_{18}$: 1112.6. found: 1113.4 $(M+H)^+$.

Synthesis of 38

To compound 37 (100 mg, 0.09 mmol) in solution of DCM (5 mL), was added piperidine (382 mg, 4.49 mmol). The reaction was stirred at rt for 2 h. The reaction was concentrated and suspended in ether (30 mL). The solid was collected via filtration. The crude product was dissolved in water and purified on RP-HPLC to afford 38 (50 mg, 0.056 mmol, 63% yield). Mass Spec (lo-res): Calc'd for $C_4H_{70}N_6O_{16}$: 890.5. found: 891.4 $(M+H)^+$.

Synthesis of 39

Azido acetic acid (349 mg, 0.224 mmol, 6% wt in DCM) and HOBt (15.2 mg, 0.112 mmol) and EDC (43 mg, 0.224 mmol) was stirred in DCM (1 mL) at rt. After 30 min, compound 38 (50 mg, 0.056 mmol) in solution of DMF (1 ml), was added with DIPEA (0.02 mL, 0.112 mmol). The reaction was stirred at rt for 30 min, then diluted with water, and purified on HPLC to afford 39 (35 mg, 0.036 mmol, 64% yield). Mass Spec (lo-res): Calc'd for $C_{59}H_{88}N_6O_{19}$: 973.6. found: 974.4 $(M+H)^+$.

Synthesis of 40

To compound 39 (35 mg, 0.036 mmol), was added TFA/TIS/water (95:2.5:2.5, 1 mL). The reaction was stirred at rt for 30 min. The reaction was concentrated and redissloved in water and purified on RP-HPLC to afford 40 (25 mg, 0.031 mmol, 86% yield). $^1$H NMR ($D_2O$, 400 MHz), δ: 8.35 (b, 1H), 8.00 (b, 2H), 7.92 (b, 1H), 4.25-4.20 (m, 1H), 4.10-4.06 (m, 1H), 3.88 (s, 2H), 3.80 (m, 1H), 3.60-3.42 (m, 6H), 3.43 (t, 1H, J=6.0 Hz), 3.22-3.14 (m, 2H), 2.82-2.60 (m, 4H), 2.30-2.25 (m, 2H), 2.30-2.25 (m, 2H), 2.00-1.74 (m, 3H), 1.18 (d, J=7.2 Hz, 3H), 0.74 (t, J=6.8 Hz, 6H). Mass Spec (lo-res): Calc'd for $C_{30}H_{47}N_9O_{17}$: 805.3. found: 806.2 $(M+H)^+$.

Synthesis of 41

To compound 40 (2 mg, 2.5 umol) in solution of MeOH (0.2 ml), was added $CuSO_4$ (5 drops, 0.1 M aq solution), sodium ascorbate (3 mg) and fluoropentyne (3 drops). The reaction was stirred at rt for 30 min. The reaction was concentrated and purified on HPLC to afford 41 (1.4 mg, 1.6 umol, 63% yield). $^1$H NMR ($CD_3OD$, 400 MHz), δ: 7.81 (s, 1H), 5.22 (s, 2H), 4.70 (m, 2H), 4.53 (t, J=5.4 Hz, 1H), 4.41 (t, J=5.4 Hz, 1H), 4.35-4.30 (m, 1H), 4.08-4.04 (m, 1H), 3.83-3.60 (m, 4H), 3.54-3.20 (m, 8H), 2.95-2.75 (m, 6H), 2.45-2.43 (m, 2H), 2.20-1.95 (m, 5H), 1.37 (d, J=7.2 Hz, 3H), 0.92 (d, J=6.8 Hz, 6H). $^{19}$F NMR ($CD_3OD$, 376 MHz), δ: −76.55 (TFA, —$CF_3$), −221.6 (tt, J=47 Hz, 27 Hz). Mass Spec (lo-res): Calc'd for $C_{35}H_{54}N_9O_{17}$: 891.2. found: 892.3 $(M+H)^+$.

Example 8

Scheme 9

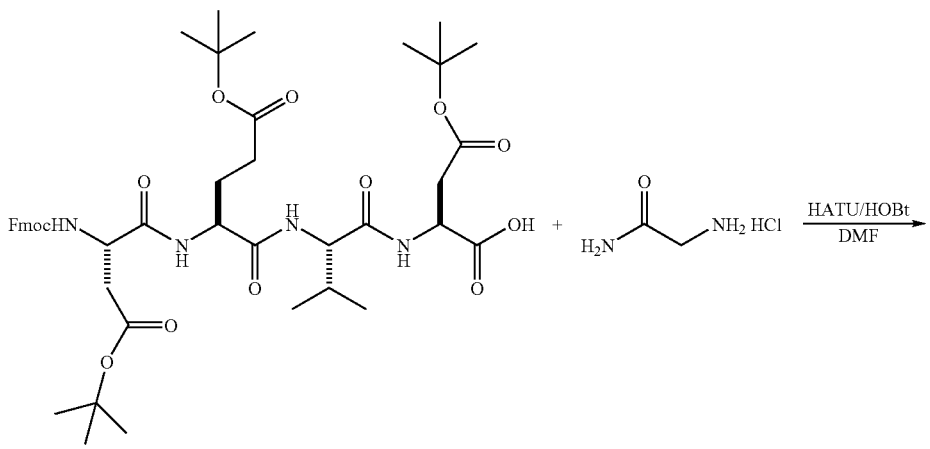

9

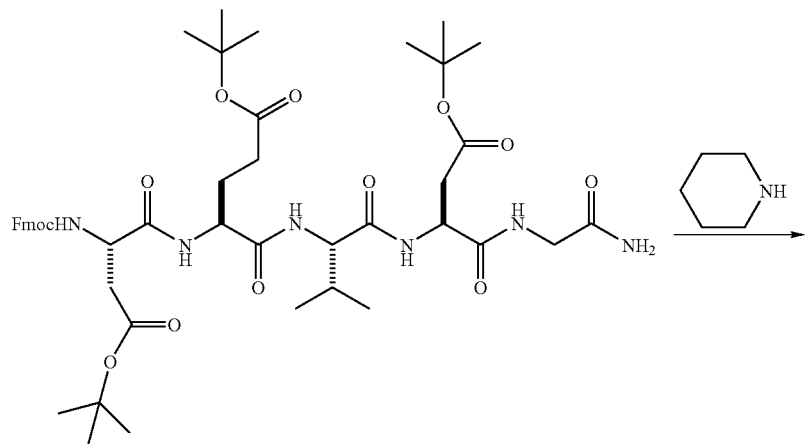

-continued
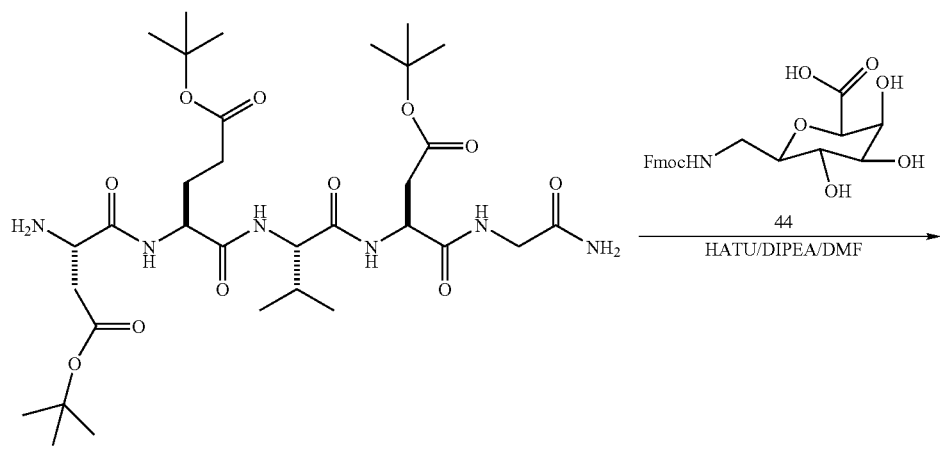
43
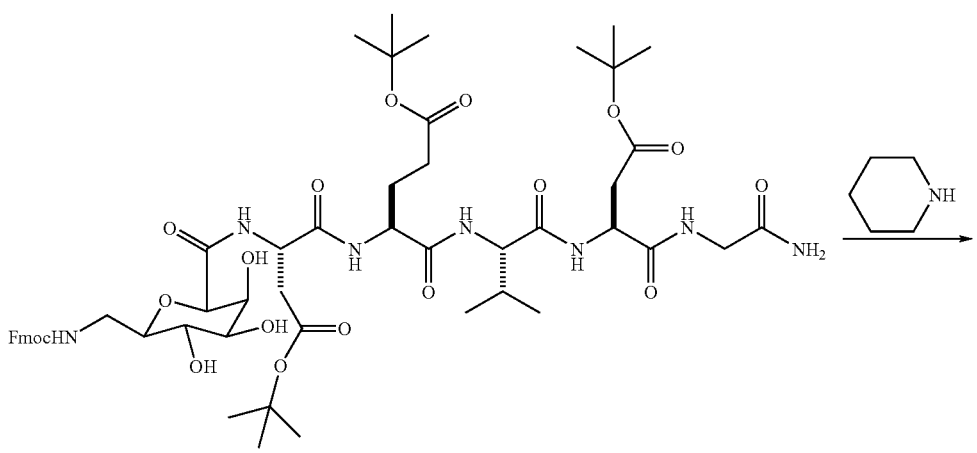
45
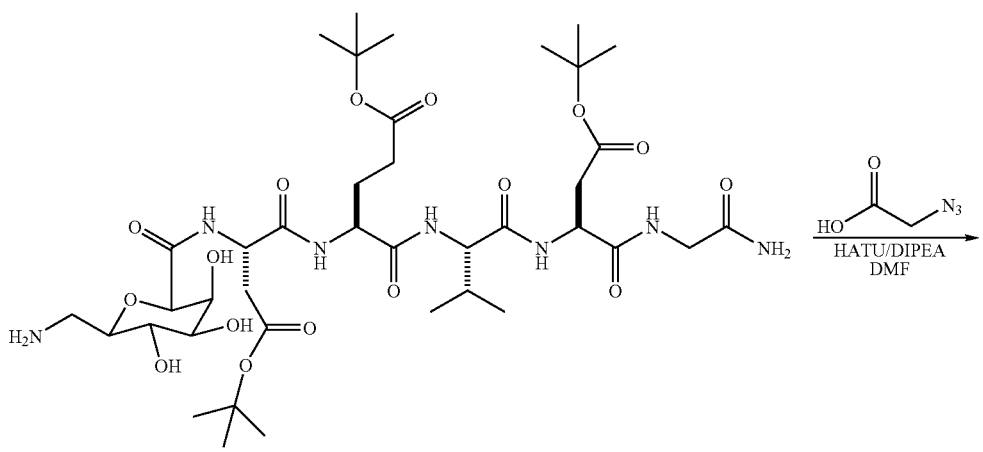
46

-continued

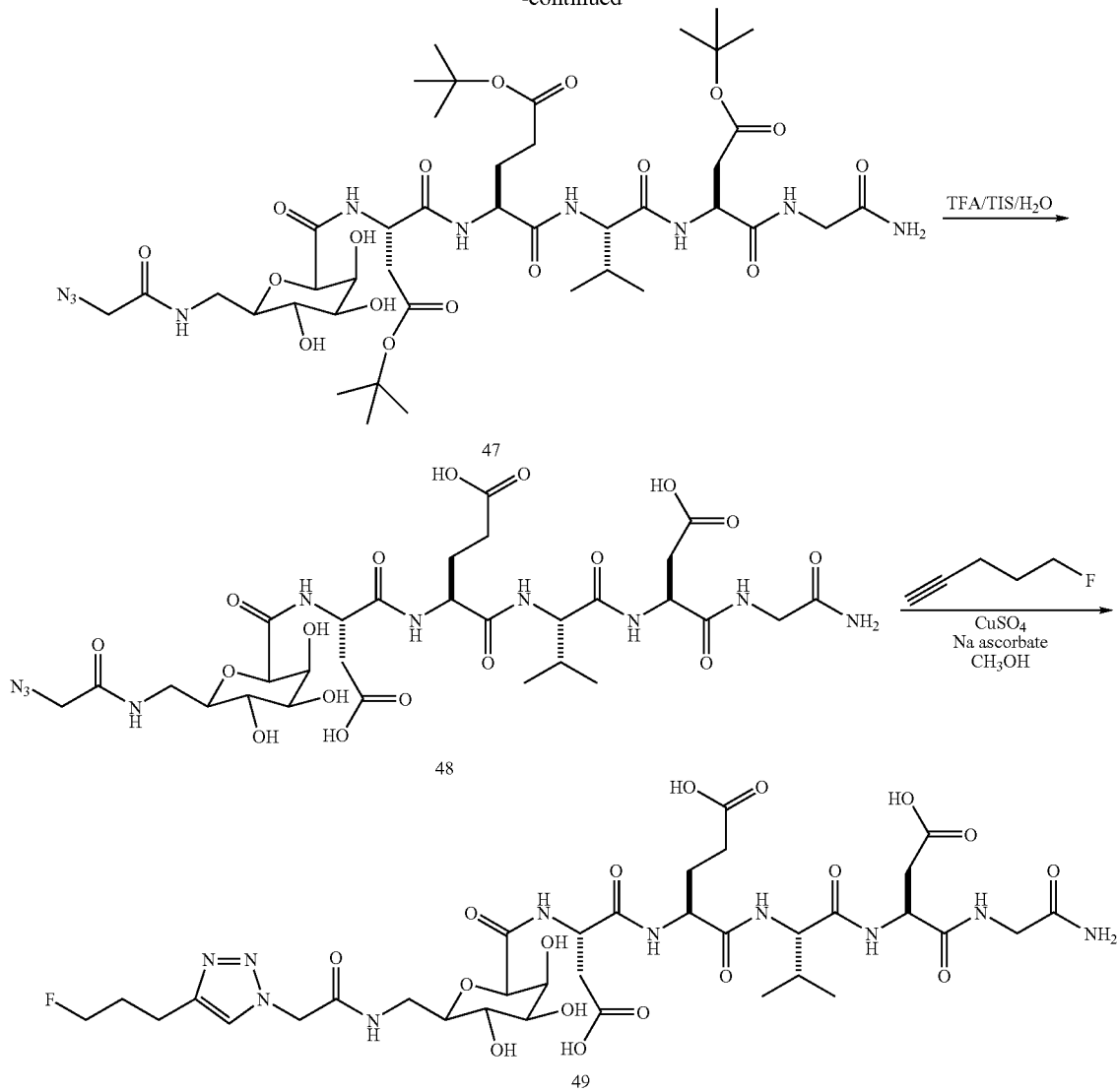

Synthesis of 42

To a round bottom flask containing compound 9 (300 mg, 0.346 mmol) in DMF (5 mL) at room temperature, was added HATU (145 mg, 0.381 mmol) and DIPEA (0.181 mL, 1.038 mmol). The reaction was stirred at room temperature for 45 min. Then 2-aminoacetamide hydrochloride (38.3 mg, 0.346 mmol) was added to the mixture. The reaction was stirred at room temperature for 3 hr and LC/MS demonstrated the completion of the reaction. The mixture was concentrated in vacuo and then washed with water (5 mL×3) and ether (5 mL×3) to afford the product (300 mg, 94% Yield). Mass Spec (lo-res): Calc'd for $C_{47}H_{66}N_6O_{13}$: 922.47. found: 923.4 (M+H)$^+$.

Synthesis of 43

To a round bottle flask containing compound 42 (300 mg, 0.325 mmol) in DCM (5 mL), was added piperidine (0.161 mL, 1.625 mmol). LCMS indicates completion of the reaction after overnight stirring. The reaction was concentrated to remove piperidine. Acetonitrile (10 mL×3) was added to facilitate co-evaporation. The residue was dried under vacuo for 2 hrs. The white solid residue was then washed with ether (10 mL×3) by ultrasound. The residue solid was filtered and dried under vacuo overnight to afford compound 43 (200 mg, 88% yield). Mass Spec (lo-res): Calc'd for $C_{32}H_{56}N_6O_{11}$: 700.40. found: 701.3 (M+H)$^+$.

Synthesis of 45

To a round bottom flask containing compound 44 (43 mg, 0.1 mmol) in DMF (5 mL) at room temperature, was added HATU (42 mg, 0.11 mmol) and DIPEA (0.052 mL, 0.3 mmol). The reaction was stirred at room temperature for 1 hr. Compound 43 (70 mg, 0.1 mmol) was then added to the mixture. The reaction was stirred at room temperature for 4 hr and LC/MS demonstrated the completion of the reaction. The mixture was concentrated under vacuo and then washed with water (5 mL×3) and ether (5 mL×3) to afford the product (70 mg, 63% yield). Mass Spec (lo-res): Calc'd for $C_{54}H_{77}N_7O_{18}$: 1111.53. found: 1112.3 (M+H)$^+$.

Synthesis of 46

To a round bottle flask containing compound 45 (65 mg, 0.058 mmol) in DCM (3 mL), was added piperidine (0.029 mL, 0.292 mmol). LCMS indicates completion of the reaction after 4 hrs. The reaction was concentrated to remove piperidine. Acetonitrile (5 mL×3) was added to facilitate co-evaporation. The residue was dried under vacuo for 2 hrs. The white solid residue was then washed with ether (5 mL×3) by ultrasound. The residue solid was filtered and dried under vacuo overnight to afford compound 46 (46 mg, 88% yield). Mass Spec (lo-res): Calc'd for $C_{39}H_{67}N_7O_{16}$: 889.46. found: 890.4 $(M+H)^+$.

Synthesis of 47

To a round bottom flask containing azido acetic acid (21 mg, 0.103 mmol, 50% in THF) in DMF (5 mL) at room temperature, was added HATU (41.3 mg, 0.109 mmol) and DIPEA (45 µL, 0.258 mmol). The reaction was stirred at room temperature for 2 hr. Compound 46 (46 mg, 0.052 mmol) was then added to the mixture. The reaction was stirred at room temperature overnight until LC/MS indicates the completion of the reaction. The mixture was concentrated under vacuo and then washed with EtOH (5 mL×3) to afford the product (40 mg, 80% yield). Mass Spec (lo-res): Calc'd for $C_{41}H_{68}N_{10}O_{17}$: 972.48. found: 973.4 $(M+H)^+$.

Synthesis of 48

Compound 47 (20 mg, 0.021 mmol) was dissolved in a cocktail solution of TFA:TIS:$H_2O$=95:2.5:2.5 (2 mL) and stirred for 2 hr at room temperature. The reaction was concentrated, redissolved in water, filtered, purified on semi-prep HPLC, and lyophilized to afford the product (11.5 mg, 69.5% yield). $^1$H NMR (400 MHz, $CD_3OD$) δ 0.95-0.98 (dd, 8H, J=7.6 Hz), 1.95-2.03 (m, 1H), 2.10-2.17 (m, 2H), 2.39-2.45 (m, 2H), 2.80-2.89 (m, 2H), 2.92-3.00 (m, 2H), 3.33-3.36 (m, 1H), 3.48-3.65 (m, 4H), 3.72-3.80 (m, 2H), 3.89-3.90 (m, 1H), 3.93-3.95 (m, 2H), 4.04-4.07 (m, 2H), 4.19-4.21 (m, 1H), 4.35-4.39 (m, 1H), 4.59-4.62 (t, 1H), 4.70-4.73 (t, 1H). Mass Spec (lo-res): Calc'd for $C_{29}H_{44}N_{10}O_{17}$: 804.29. found: 805.2 $(M+H)^+$.

Synthesis of 49

To a round bottom flask containing compound 48 (11.5 mg, 0.014 mmol) in MeOH (0.8 mL), was added $CuSO_4$ solution (0.014 mL, 0.1 M), sodium ascorbate solution (6 µL, 0.5 M), and a drop of fluoropentyne. The reaction was stirred at room temperature for 2 hr until LC/MS indicates the completion of the reaction. The reaction was concentrated, redissolved in water, filtered, purified on semi-prep HPLC, and lyophilized to afford the product (8 mg, 63% Yield). $^1$H NMR (400 MHz, $CD_3OD$) δ 0.95-0.98 (t, 8H, J=6.8 Hz), 1.96-2.16 (m, 5H), 2.40-2.46 (m, 1H), 2.80-2.99 (m, 7H), 3.36-3.38 (m, 1H), 3.48-3.55 (m, 4H), 3.73-3.78 (m, 2H), 3.89-3.93 (d, 1H), 4.05-4.09 (m, 2H), 4.19-4.21 (m, 1H), 4.37-4.43 (m, 2H), 4.52-4.55 (t, 1H), 4.59-4.62 (t, 1H), 4.71-4.74 (t, 1H), 5.20 (s, 2H), 7.84 (s, 1H). $^{19}$F NMR ($CD_3OD$, 376 MHz), δ: −76.9 (TFA, —$CF_3$), −222.08 (tt, J=47.0 Hz, 25.9 Hz). Mass Spec (lo-res): Calc'd for $C_{34}H_{51}FN_{10}O_{17}$: 890.34. found: 891.3 $(M+H)^+$.

Example 9

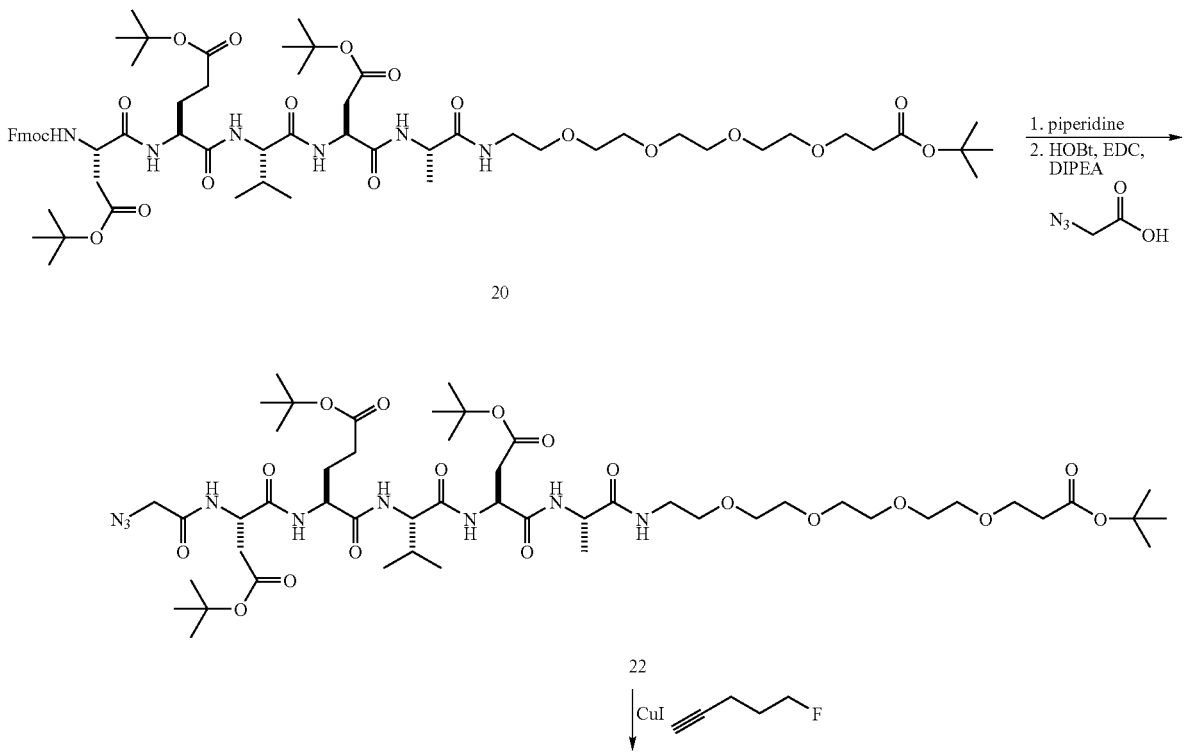

Scheme 10

-continued

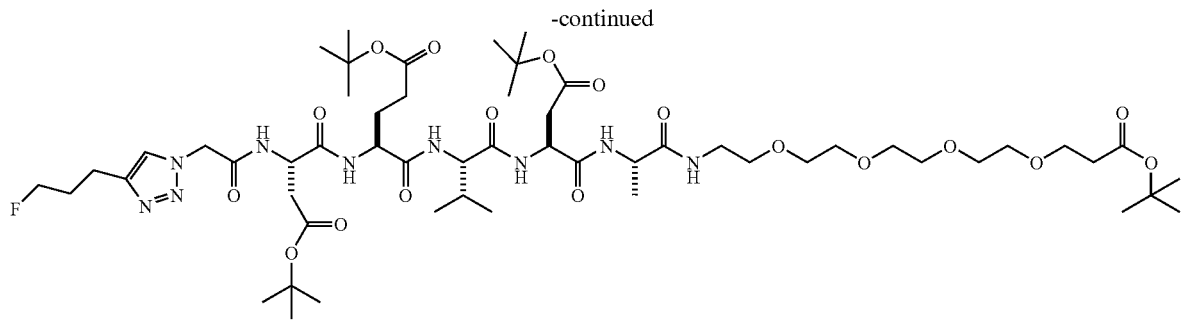

30

Synthesis of 22

Compound 20 (95 mg, 0.077 mmol) was dissolved in DCM (1 mL). To the solution, was added piperidine (326 mg, 3.83 mmol). After 2 h, the reaction was concentrated in vacuo to afford the deprotected intermediate (78 mg). To the solution of 2-azido acetic acid (258 mg, 6% wt solution in DCM, 0.153 mmol) in DCM (1 mL), was added HOBt (20.7 mg, 0.153 mmol) and EDC (29.3 mg, 0.153 mmol). The mixture was stirred at room temperature for 20 min. To the mixture was added the deprotected intermediate (78 mg, 0.077 mmol) in solution of DMF (1.00 ml) and DIPEA (0.027 ml, 0.153 mmol). The reaction was stirred at room temperature for 30 min. The mixture was concentrated in vacuo and diluted with water (15 mL). The white solid precipitate was filtered, dried and purified on RP-HPLC to afford 22 (71 mg, 0.064 mmol, 84% yield). $^1$H NMR (CD$_3$OD, 400 MHz) δ: 4.72-4.62 (m, 2H), 4.38-4.28 (m, 2H), 4.07 (d, J=7.2 Hz, 1H), 3.93 (s, 2H), 3.69 (t, J=7.2 Hz, 2H), 3.62-3.58 (m, 13H), 3.55 (t, J=7.2 Hz, 2H), 3.40-3.35 (m, 2H), 2.87-2.81 (m, 2H), 2.71-2.65 (m, 2H), 2.47 (t, J=6.0 Hz), 2.36-2.30 (m, 2H), 2.15-2.06 (m, 2H), 1.95-1.88 (m, 1H), 1.45-1.44 (m, 36H), 1.35 (d, J=7.2 Hz, 3H), 0.97 (t, J=6.4 Hz, 6H). Mass Spec (lo-res): Calc'd for C$_{50}$H$_{87}$N$_9$O$_{18}$, calc'd: 1101.6 found: 1102.5 (M+H)$^1$.

Synthesis of 50

To compound 22 (10 mg, 9.1 μmol) in solution of MeOH (0.5 ml), was added CuSO$_4$ (5 drops, 0.1 M aq solution), Sodium Ascorbate (20 mg) and Fluoropentyne (2 drops). The reaction was stirred at rt for 30 min. The reaction was concentrated and purified on HPLC to afford 50 (6 mg, 5.1 μmoL, 56% yield). $^1$H NMR (CD$_3$OD, 400 MHz) δ:8.75 (d, J=7.2 Hz, 1H), 8.40 (d, J=6.8 Hz, 1H), 8.23 (d, J=7.2 Hz, 1H), 7.95 (d, J=7.2 Hz, 1H) 7.88-7.84 (m, 2H), 7.80 (s, 1H), 5.19 (s, 2H), 4.74-4.62 (m, 2H), 4.53 (t, J=5.6 Hz, 1H), 4.41 (t, J=5.6 Hz, 1H), 4.38-4.30 (m, 2H), 4.06 (t, J=6.4 Hz, 1H), 3.69 (t, J=6.4 Hz, 2H), 3.64-3.52 (m, 13H), 3.36 (m, 2H), 2.85-2.81 (m, 2H), 2.72-2.64 (m, 1H), 2.46 (t, J=6.0 Hz, 1H), 2.35 (m, 1H), 2.21-1.90 (m, 3H), 1.44 (m, 36H), 1.35 (d, J=7.2 Hz, 3H), 0.93 (d, J=6.8 Hz, 6H). $^{19}$F NMR (CD$_3$OD, 376 MHz), δ: −76.55 (TFA, —CF$_3$), −221.6 (tt, J=47 Hz, 27 Hz). Mass Spec (lo-res): Calc'd for C$_{55}$H$_{94}$FN$_9$O$_{18}$: 1187.7. found: 1188.6 (M+H)$^+$.

Example 10

Scheme 11
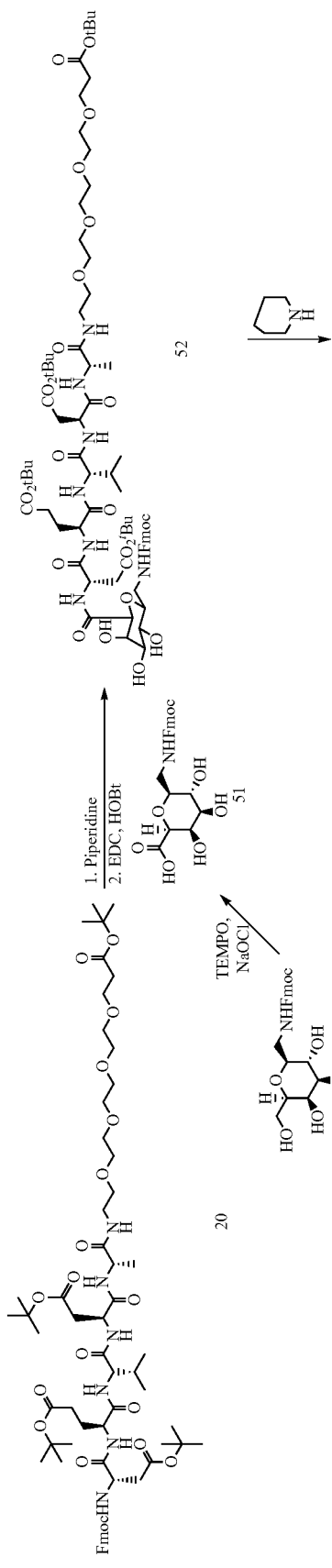
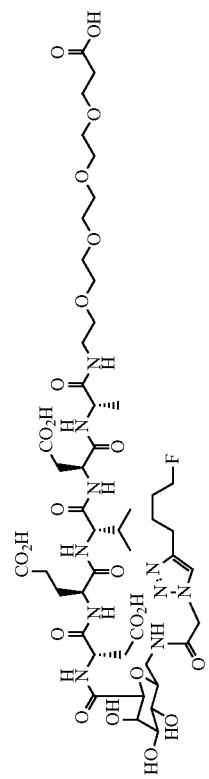
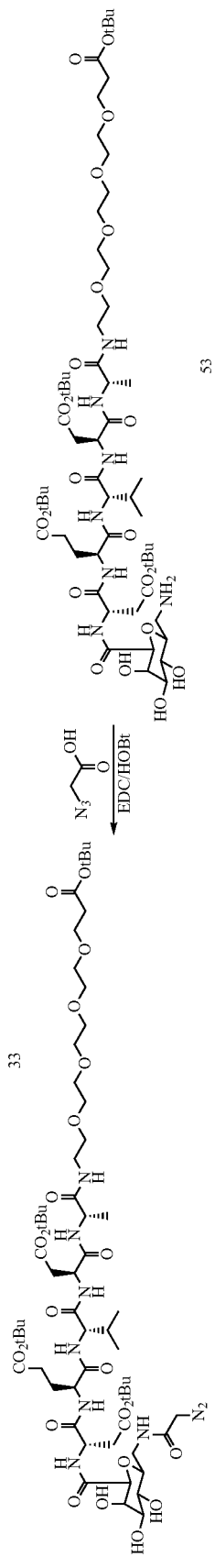
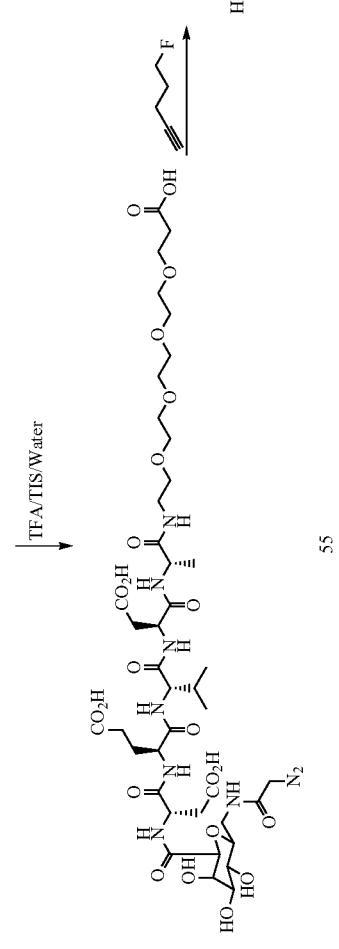

Synthesis of 51

To compound 33 (10 g, 24 mmol) in THF (115 ml) and water (115 ml), was added the sodium bicarbonate (12 g, 143 mmol). To the mixture was added TEMPO (2,2,6,6-Tetramethyl Piperidinyloxy, Free Radical) (0.752 g, 4.81 mmol) and sodium bromide (0.743 g, 7.22 mmol). The mixture was cooled to 0° C. with ice bath, sodium hypochrolite solution (aq, 10%-13% chorine) (39.4 g, 53.0 mmol) drop wise in 45 minutes. After addition, the reaction mixture was concentrated under vacuum without heating to remove organic volatiles. The aqueous layer was extracted with $Et_2O$ (50 mL×2), then acidified with HCl (aq, conc. 37%, 15 mL) until pH reached 2. The aqueous layer was extracted with ethyl acetate (100 mL×4). The combined organic layers were concentrated to afford crude product as a white solid. The crude product was triturated with hot diethyl ether (75 mL×3) under ultrasound to give a while solid 51 (9.2 g, 89% yield). $^1$H NMR (DMSO, 400 MHz), δ: 12.10 (b, 1H), 7.89 (d, 2H, J=7.2 Hz), 7.70 (d, 2H, J=7.2 Hz), 7.42 (t, 2H, J=7.2 Hz), 7.34 (t, 2H, J=7.2 Hz), 7.26 (t, 1H, J=4.4 Hz), 4.93 (b, 1H), 4.89 (b, 1H), 4.76 (b, 1H), 4.31 (d, 2H, J=6.8 Hz), 4.24 (d, 1H, J=6.8 Hz), 4.04 (s, 1H), 3.94 (s, 1H), 3.58-3.51 (m, 1H), 3.30-3.25 (m, 1H), 3.17-2.97 (m, 3H). Mass Spec (lo-res): Calc'd for $C_{22}H_{23}NO_8$: 429.14. found: 430.1 $(M+H)^+$.

Synthesis of 53

Compound 20 (1.0 g, 0.81 mmol) was dissolved in DCM (25 mL). To the solution was added piperidine (0.399 mL, 4.03 mmol). The reaction was stirred at rt for 6 h. The mixture was concentrated and washed with hexanes (15 mL×3). The resulted white solid (580 mg, 0.569 mmol, 71% yield) was used in coupling reaction directly without any further purification. Compound 51 (120 mg, 0.279 mmol) was dissolved in DMF (1 mL), HOBt (37.8 mg, 0.279 mmol) and EDC (58.9 mg, 0.279 mmol) were added. The reaction mixture was stirred at rt for 20 min. To the reaction mixture was added the above white solid (285 mg, 0.279 mmol) in DMF with DIPEA (0.107 mL, 0.615 mmol). The reaction was stirred at rt for 2 h, then diluted with water (30 mL) to afford white solid 52 (350 mg). The intermediate 52 was then dissolved in DCM (5 mL). The reaction suspension was stirred with addition of piperidine (104 mg, 1.22 mmol). After 30 min, the reaction was concentrated. The residue was washed with hexanes (5 mL×2) and ether (5 mL×2) to afford 53 (140 mg, 0.116 mmol, 47% yield). Mass Spec (lo-res): Calc'd for $C_{55}H_{97}N_7O_{22}$: 1207.7. found: 1208.5 $(M+H)^+$.

Synthesis of 54

To the solution of 2-azido acetic acid (1171 mg, 6% wt solution in DCM, 0.695 mmol) in DCM (2 ml), was added HOBt (94 mg, 0.695 mmol) and EDC (133 mg, 0.695 mmol). The mixture was stirred at room temperature for 20 min. To the mixture was added 53 (140 mg, 0.116 mmol) and DIPEA (45 mg, 0.348 mmol) in the solution of DMF (1.00 ml). The reaction was stirred at room temperature for 2 h. The reaction was concentrated and diluted with water (20 mL). The white precipitate was collected, redissloved in MeOH (3 mL) and purified on HPLC to afford 54 (40 mg, 0.031 mmol, 27% yield). Mass Spec (lo-res): Calc'd for $C_{57}H_{98}N_{10}O_{23}$, calc'd: 1290.8. found: 1291.6 $(M+H)^+$.

Synthesis of 55

To compound 54 (40 mg, 0.031 mmol), was added TFA/TIS/water (95:2.5:2.5, 2 mL). The reaction was stirred at rt for 30 min. The reaction was concentrated and dissolved in water and purified on RP-HPLC to afford 55 (30 mg, 0.028 mmol, 91% yield). $^1$H NMR ($CD_3OD$, 400 MHz), δ: 8.30 (d, 1H, J=6.8 Hz), 8.22 (m, 1H), 8.04 (d, 1H, J=7.2 Hz), 8.00 (d, 1H, J=8.0 Hz), 7.93 (d, 1H, J=6.8 Hz), 7.80 (t, 1H, J=6.0 Hz), 4.76-4.64 (m, 2H), 4.40-4.29 (m, 2H), 4.20 (dd, 1H, J=3.2, 1.6 Hz), 4.08-4.04 (m, 2H), 3.95 (s, 2H), 3.74-3.70 (m, 3H), 3.64-3.58 (m, 13H), 3.57-3.44 (m, 5H), 3.38-3.34 (m, 2H), 3.00-2.74 (m, 6H), 2.55 (t, 2H, J=6.0 Hz), 2.46-2.34 (m, 2H), 2.20-2.08 (m, 2H), 2.02-1.92 (m, 1H), 1.36 (d, 3H, J=6.8 Hz), 0.96 (t, 6H, J=6.8 Hz). Mass Spec (lo-res): Calc'd for $C_{41}H_{66}N_{10}O_{23}$: 1066.4. found: 1067.3 $(M+H)^+$.

Synthesis of 56

To compound 55 (7.0 mg, 6.6 umol) in solution of MeOH (1 ml), was added $CuSO_4$ (5 drops, 0.1 M aq solution), Sodium Ascorbate (5 mg) and Fluoropentyne (2 drops). The reaction was stirred at rt for 30 min. The reaction was concentrated and purified on HPLC to afford 56 (4.5 mg, 3.9 umoL, 60% yield). $^1$H NMR ($CD_3OD$, 400 MHz), δ: 8.42 (t, 1H, J=5.6 Hz), 8.32 (d, 1H, J=7.2 Hz), 8.23 (d, 1H, J=7.6 Hz), 8.05 (d, 1H, J=7.2 Hz), 7.99 (d, 1H, J=8.0 Hz), 7.93 (d, 1H, J=7.2 Hz), 7.86 (s, 1H), 7.81 (t, 1H, J=5.6), 5.20 (s, 2H), 4.76-4.64 (m, 2H), 4.53 (t, 1H, J=6.0 Hz), 4.44-4.26 (m, 3H), 4.21 (dd, 1H, J=3.2, 1.6 Hz), 4.08-4.04 (m, 2H), 3.80-3.71 (m, 3H), 3.64-3.58 (m, 13H), 3.57-3.44 (m, 5H), 3.38-3.34 (m, 3H), 3.00-2.74 (m, 6H), 2.55 (t, 2H, J=6.0 Hz), 2.46-2.34 (m, 2H), 2.20-1.92 (m, 6H), 1.35 (d, 3H, J=7.2 Hz), 0.96 (t, 6H, J=6.8 Hz). $^{19}$F NMR ($CD_3OD$, 376 MHz), δ: -76.55 (TFA, —$CF_3$), -221.85 (tt, J=47 Hz, 27 Hz). Mass Spec (lo-res): Calc'd for $C_{46}H_{73}FN_{10}O_{23}$: 1152.5. found: 1153.3 $(M+H)^+$.

Example 11

Scheme 12

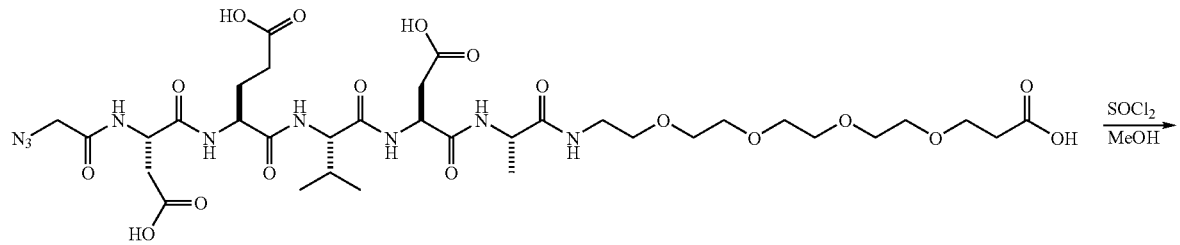

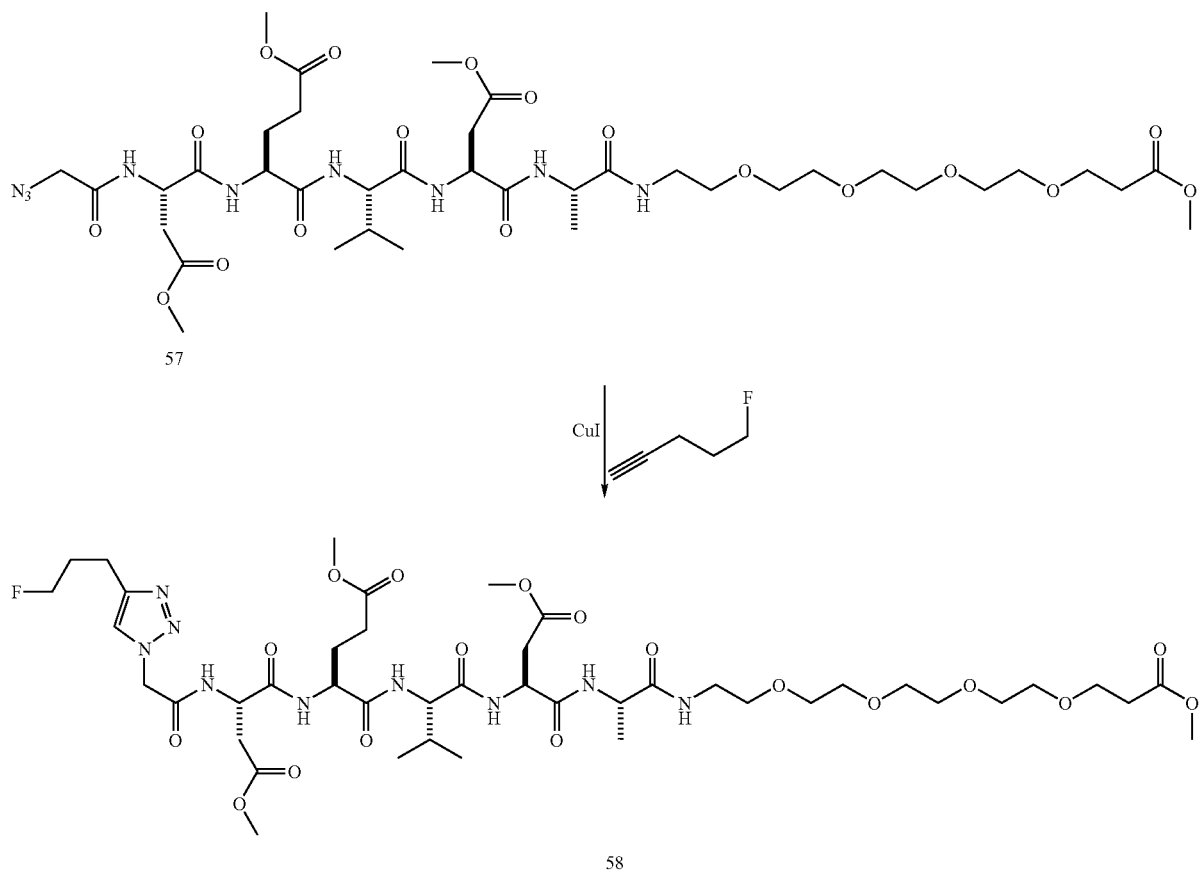

57

58

Synthesis of 57

To a solution of compound 23 (25 mg, 0.028 mmol) in MeOH (3 mL), was added thionyl chloride (0.042 mL, 0.57 mmoL). The reaction mixture was stirred at rt for 20 min. The mixture was diluted with water (3 mL) and purified on HPLC to afford 57 (20 mg, 0.021 mmol, 75% yield). $^1$H NMR (CD$_3$OD, 400 MHz), δ: 7.82 (b, 1H), 4.75-4.68 (m, 2H), 4.36-4.28 (m, 2H), 4.06 (d, 1H, J=7.2 Hz), 3.93 (s, 2H), 3.73 (t, 2H, J=6.4 Hz), 3.69-3.60 (m, 21H), 3.57-3.51 (m, 2H), 3.38-3.34 (m, 2H), 2.96-2.89 (m, 2H), 2.83-2.75 (m, 2H), 2.58 (t, 2H, J=6.4 Hz), 2.48-2.42 (m, 2H), 2.20-2.10 (m, 2H), 2.03 (s, 3H), 2.02-1.92 (m, 1H), 1.36 (d, 3H, J=7.2 Hz), 0.97 (t, 6H, J=7.2 Hz). Mass Spec (lo-res): Calc'd for C$_{38}$H$_{63}$N$_9$O$_{18}$: 933.4. found: 934.3 (M+H)$^+$.

Synthesis of 58

To compound 57 (4.0 mg, 4.28 umol) in solution of MeOH (1 mL), was added CuSO$_4$ (5 drops, 0.1 M aq solution), sodium ascorbate (5 mg) and fluoropentyne (2 drops). The reaction was stirred at rt for 30 min. The reaction was concentrated and purified on HPLC to afford 58 (3.0 mg, 2.94 umol, 68.7% yield). $^1$H NMR (CD$_3$OD, 400 MHz), δ: 7.80 (s, 1H), 5.19-5.20 (s, 2H), 4.72-4.68 (m, 2H), 4.54-4.52 (m, 2H), 4.42-4.40 (m, 2H), 4.25 (s, 2H), 4.09 (t, 2H, J=6.4 Hz), 3.69-3.60 (m, 21H), 3.57-3.51 (m, 2H), 3.38-3.34 (m, 2H), 2.96-2.89 (m, 2H), 2.83-2.75 (m, 2H), 2.58 (t, 2H, J=6.4 Hz), 2.48-2.42 (m, 2H), 2.20-1.90 (m, 6H), 1.80-1.60 (m, 2H), 2.02-1.92 (m, 1H), 1.36 (d, 3H, J=7.2 Hz), 0.95 (t, 6H, J=7.2 Hz). $^{19}$F NMR (CD$_3$OD, 376 MHz), δ: −76.55 (TFA, —CF$_3$), −221.72 (tt, J=47 Hz, 27 Hz). Mass Spec (lo-res): Calc'd for C$_{43}$H$_{70}$FN$_9$O$_{18}$: 1019.5. found: 1020.4 (M+H)$^+$.

Example 12

Scheme 13 ('Asp($^t$Bu)-Glu($^t$Bu)-Val-Asp($^t$Bu)' disclosed as SEQ ID NO: 2)

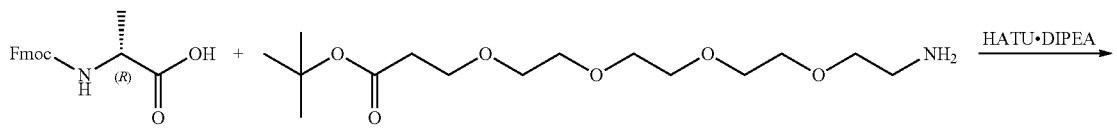

-continued

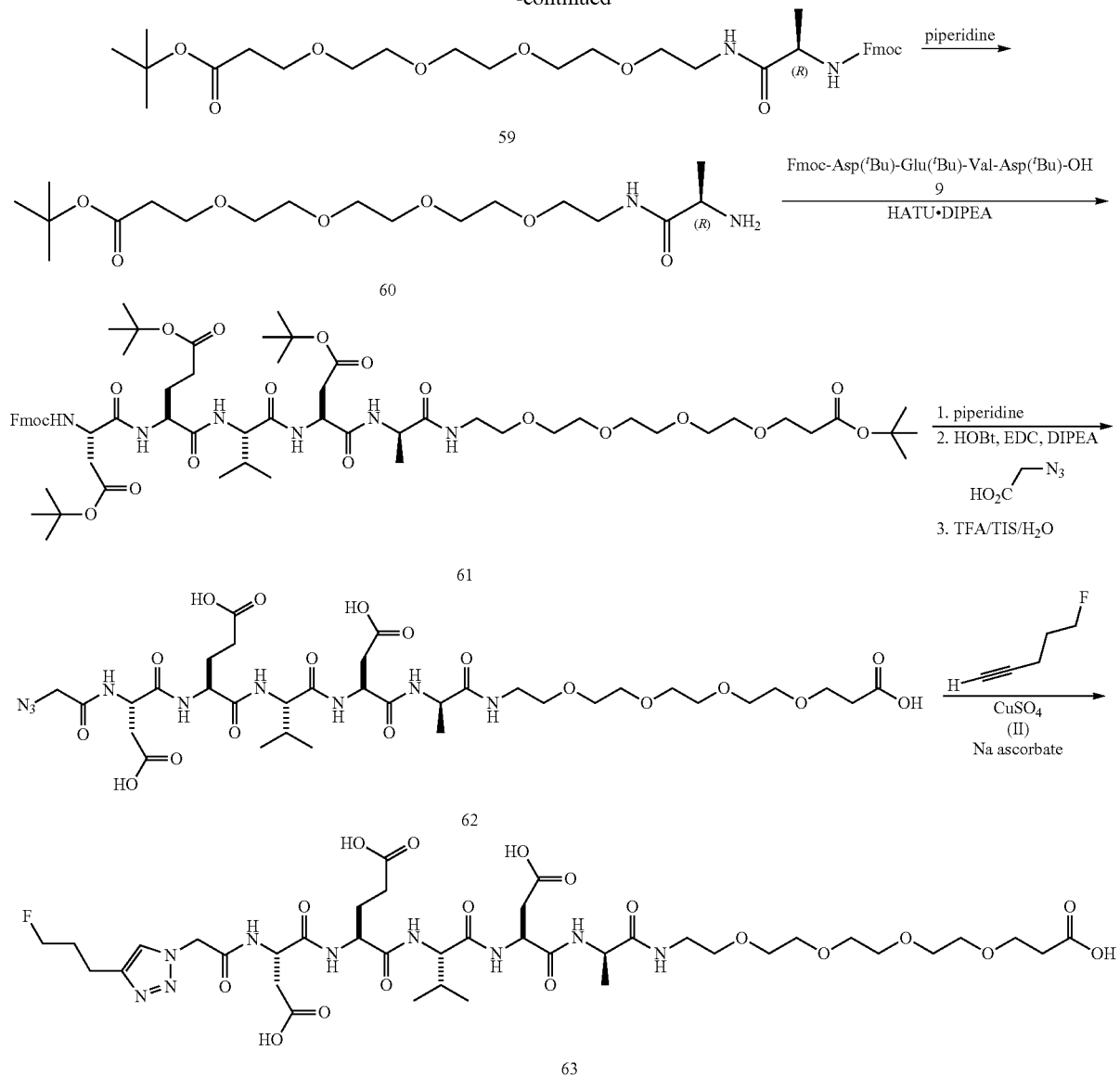

Synthesis of 59

To Fmoc-protected D-alanine (685 mg, 2.2 mmol) and NH$_2$-d(PEG)$_4$-O$^t$Bu (575 mg, 1.8 mmol) in DCM (4 mL), was added HATU (895 mg, 2.6 mmol) followed by DIPEA (349 mg, 2.7 mmol). The reaction was stirred at room temperature for 2 hours. The reaction mixture was then diluted with DCM (50 ml) and washed with NH$_4$Cl (sat. aq., 30 mL) and then H$_2$O (30 mL). The mixture was concentrated and purified on a silica gel column using EtOAc as the eluent to afford 59 (993 mg, 1.6 mmol, 73% yield). Mass Spec (lo-res): Calc'd for C$_{33}$H$_{46}$N$_2$O$_9$: 614.3. found: 615.3 (M+H)$^+$.

Synthesis of 60

To a solution of compound 59 (990 mg, 1.6 mmol) in DCM (4 mL) was added piperidine (682 mg, 8.0 mmol). The reaction was stirred for 8 hours at room temperature. The reaction was concentrated on a rotary evaporator and then co-evaporated with MeCN (3×5 mL). The residue was then purified on a silica gel column using EtOAc and then 3:1 DCM:MeOH to elute 60 (569 mg, 1.5 mmol, 90% yield). Mass Spec (lo-res): Calc'd for C$_1$H$_{36}$N$_2$O$_7$: 392.3. found: 393.2 (M+H)$^+$.

Synthesis of 61

To compound 9 (2.0 g, 2.3 mmol) in a solution of DMF (7 mL), was added HOBt (360 mg, 2.7 mmol) and EDC (507 mg, 2.7 mmol). The reaction was stirred at room temperature for 20 min. Compound 60 (569 mg, 1.5 mmol) was added in DCM (6.0 mL) followed by DIPEA (491 mg, 3.8 mmol). The reaction was stirred at room temperature overnight. The resulting mixture was then diluted with DCM (30 mL) and washed with H$_2$O (2×30 mL), dried (MgSO$_4$), and evaporated. The residue was purified on a silica gel column eluting with EtOAc to afford 61 (850 mg, 0.68 mmol, 46% yield). Mass Spec (lo-res): Calc'd for C$_{63}$H$_{96}$N$_6$O$_{19}$: 1240.67. found: 1241.7 (M+H)$^+$.

Synthesis of 62

Compound 61 (25 mg, 0.020 mmol) was dissolved in DCM (1 mL). To the solution, was added piperidine (86 mg, 1.0 mmol). After 2 h, the reaction was concentrated by rotary evaporation. The residue was co-evaporated with MeCN (3×2 mL) to afford the deprotected intermediate. To a solution of 2-azidoacetic acid (60 mg, 0.060 mmol) in DCM (1 mL), was added HOBt (9 mg, 0.067 mmol) and EDC (15 mg, 0.078 mmol). The mixture was stirred at room temperature for 20 min. To the mixture was added the deprotected intermediate (20 mg, 0.020 mmol) in a solution of DMF (1.0 mL) and DIPEA (0.013 ml, 0.070 mmol). The reaction was stirred at room temperature overnight. The reaction was then diluted with DCM (20 mL) and washed with $H_2O$ (2×10 mL). The DCM layer was dried with $MgSO_4$ and then concentrated in vacuo. The residue was co-evaporated with MeCN (2×5 mL). To the residue was added TFA:TIS:Water (ratio 95:2.5:2.5, 1 ml). After 30 min, the reaction was concentrated, and dissolved in water, filtered (0.45 µm) and purified by HPLC to afford 62 (5 mg, 0.006 mmol, 30% yield). Mass Spec (lo-res): Calc'd for $C_{34}H_{55}FN_9O_{18}$, calc'd: 877.37. found: 878.3 $(M+H)^+$.

Synthesis of 63

To a solution 62 (5 mg, 5.7 µmol) in MeOH (0.5 mL) was added a 0.1 M solution of $CuSO_4$ in $H_2O$ (5.7 µL, 0.57 µmol), a 0.2 M solution of sodium ascorbate in $H_2O$ (5.5 µL, 1.1 µmol), and finally 2 drops of 5-fluoropent-1-yne. After stirring at r.t. for 20 min the reaction was filtered through a 0.45 µm syringe filter, evaporated, dissolved in $H_2O$, and purified by HPLC to afford 63 (1.3 mg, 1.3 µmol, 23% yield). $^1$H NMR (400 MHz, DMSO-CD$_3$OD) δ 0.93-0.96 (dd, 6H, J=6.8 Hz), 1.40 (d, 3H, J=7.2 Hz), 1.99-2.15 (m, 5H), 2.39-2.56 (m, 5H), 2.77-2.99 (m, 7H), 3.12-3.13 (m, 1H), 3.35-3.45 (m, 1H), 3.48-3.65 (m, 12H), 3.71-3.74 (m, 2H), 3.95-3.99 (m, 1H), 4.29-4.32 (m, 2H), 4.40-4.43 (m, 1H), 4.52-4.55 (m, 1H), 4.65-4.74 (m, 2H), 5.23 (s, 2H), 7.78-7.87 (m, 5H), 8.61-8.75 (m, 2H). Mass Spec (lo-res): Calc'd for $C_{39}H_{62}FN_9O_{18}$: 963.42. found: 964.3 $(M+H)^+$.

Example 13

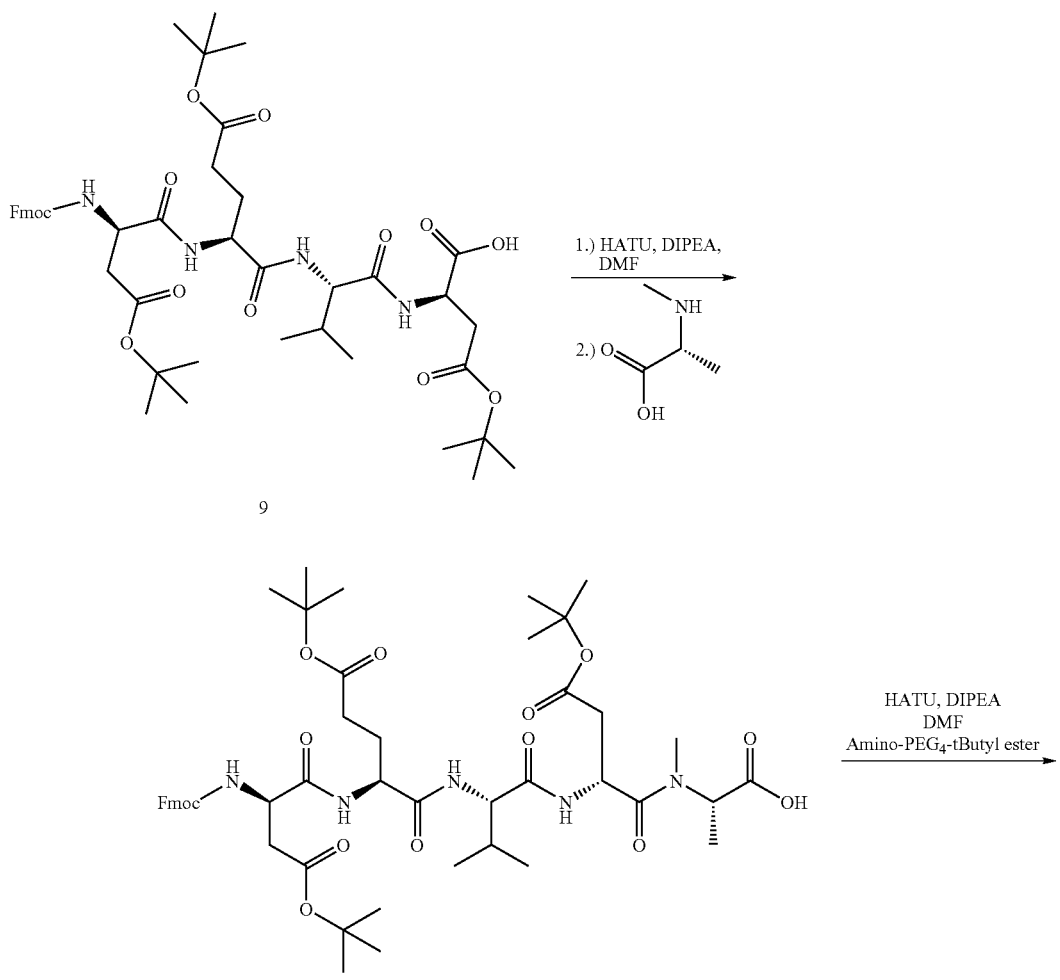

Scheme 14

-continued
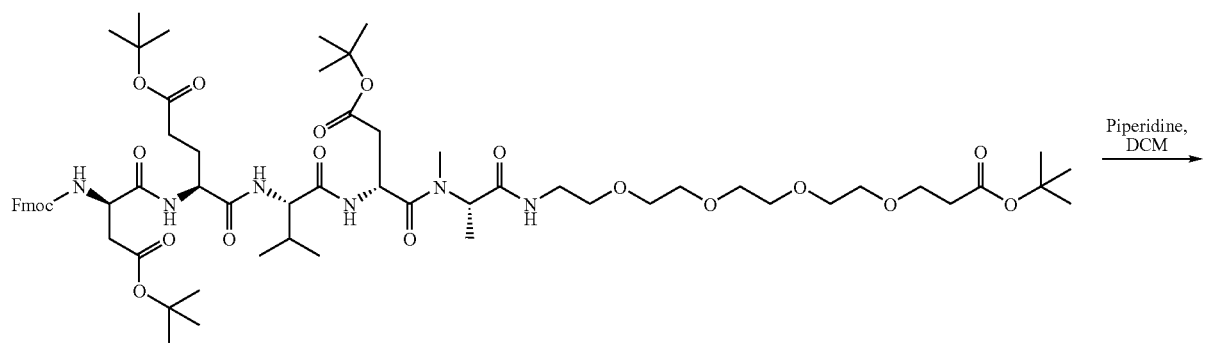
65
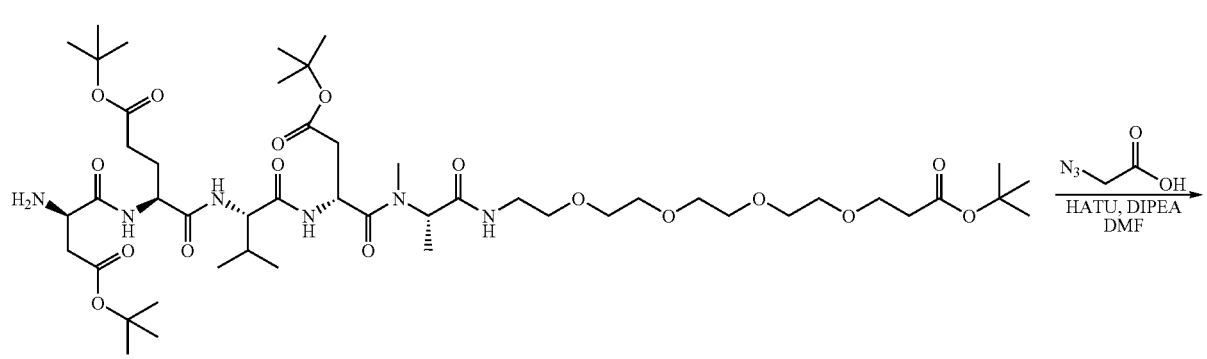
66
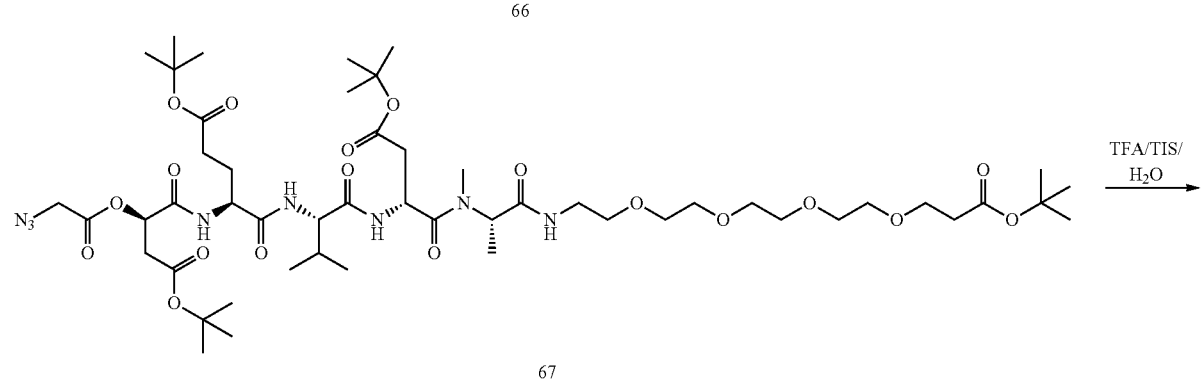
67
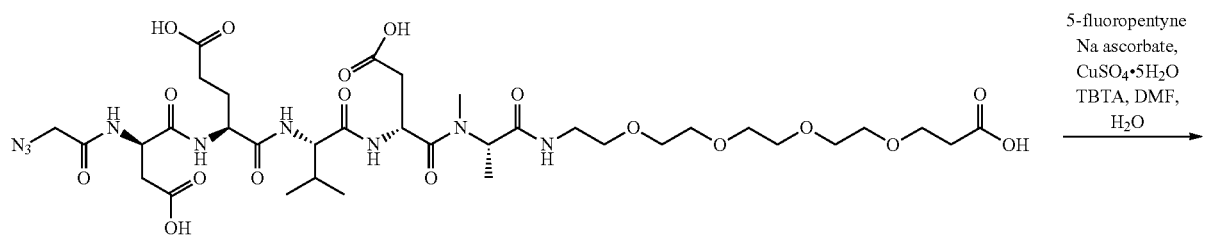
68
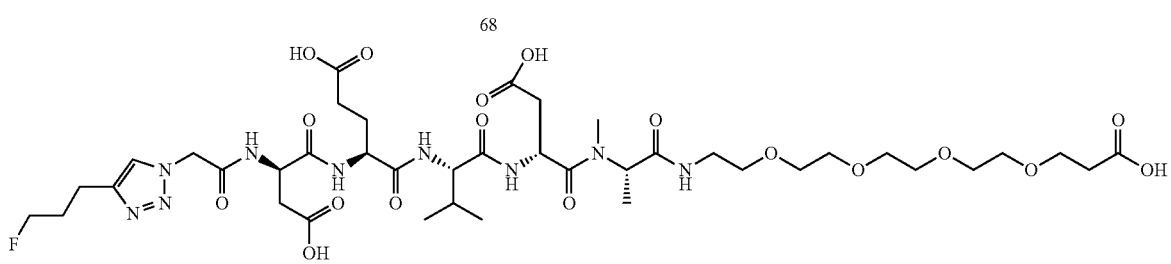
69

Synthesis of 64

HATU (0.044 g, 0.115 mmol) was added to a solution containing compound 9 (0.1 g, 0.115 mmol) and DIPEA (0.100 ml, 0.577 mmol) in DMF (1.153 ml). The reaction was stirred for 10 minutes. N-Me-ALA (0.024 g, 0.231 mmol) was added and the solution was stirred for 1 hr. The amino acid was broken up with a spatula in solution and sonicated for 2 mins. The reaction mixture was then diluted with saturated NH$_4$Cl(aq) and extracted with ethyl acetate. The organic layers were combined, dried with MgSO$_4$, filtered and concentrated to afford compound 64 (0.1 g, 0.105 mmol, 91% yield) as a white solid. Mass Spec (lo-res): Calc'd for C$_{49}$H$_{69}$N$_5$O$_{14}$: 951.5. found: 952.4 (M+H)$^+$.

Synthesis of 65

HATU (0.040 g, 0.105 mmol) was added to a solution containing compound 64 (0.1 g, 0.105 mmol), Amino-PEG$_4$-tButyl ester (0.068 g, 0.210 mmol) and DIPEA (0.055 ml, 0.315 mmol) in DMF (1.050 ml). The reaction was stirred for 15 mins. The reaction was then diluted with water and washed with ethyl acetate. The organic layers were combined, dried, filtered, concentrated, and purified using flash chromatography with ethyl acetate in DCM to afford compound 65 (0.07 g, 0.056 mmol, 53.1% yield). Mass Spec (lo-res): Calc'd for C$_{64}$H$_{98}$N$_6$O$_{19}$: 1254.7. found: 1277.6 (M+Na)$^+$.

Synthesis of 66

Piperidine (0.028 ml, 0.279 mmol) was added to a solution containing compound 65 (0.07 g, 0.056 mmol) in DCM (0.558 mL). The reaction mixture was stirred for 2 hours. The reaction mixture was then diluted with water and extracted with ethyl acetate. The organic layers were combined, dried with MgSO$_4$, filtered, and concentrated to afford compound 66 (0.056 g, 0.054 mmol, 97% yield) as crude. Mass Spec (lo-res): Calc'd for C$_{49}$H$_{88}$N$_6$O$_{17}$: 1032.6. found: 1033.6 (M+H)$^+$.

Synthesis of 67

HATU (0.032 g, 0.084 mmol) was added to a solution containing compound 66 (0.058 g, 0.056 mmol), azido acetic acid in 10% THF (0.113 g, 0.112 mmol) and DIPEA (0.015 ml, 0.084 mmol) in DMF (0.561 ml). The reaction was stirred for 10 mins. The reaction was diluted with water and extracted with ethyl acetate. The organic layers were combined, dried with MgSO$_4$, filtered, concentrated and purified using semi-prep HPLC to afford compound 67 (0.049 g, 0.044 mmol, 78% yield). Mass Spec (lo-res): Calc'd for C$_{51}$H$_{89}$N$_9$O$_{18}$: 1115.6. found: 1138.5 (M+Na)$^+$.

Synthesis of 68

Trifluoroacetic acid (0.338 mL, 4.39 mmol) was added to a solution containing compound 67 (0.049 g, 0.044 mmol) and Triisopropylsilane (8.99 μL, 0.044 mmol). The reaction mixture was stirred for 20 minutes, concentrated, and purified using semi-prep HPLC to afford compound 68. $^1$H NMR (400 MHz, D$_2$O) δ 4.97-4.93 (m, 1H), 4.72-4.67 (m, 1H), 4.57-4.54 (m, 1H), 4.22-4.19 (m, 1H), 3.89-3.87 (m, 3H), 3.59 (t, J=5.9 Hz, 2H), 3.48-3.46 (m, 12H), 3.41 (t, J=5.8 Hz, 2H), 3.20 (t, J=5.7 Hz, 2H), 2.88 (s, 3H), 2.78-2.61 (m, 4H), 2.55-2.45 (m, 3H), 2.27-2.23 (m, 2H), 1.89-1.78 (m, 4H), 1.17-1.14 (m, 3H), 0.74-0.69 (m, 6H). Mass Spec (lo-res): Calc'd for C$_{35}$H$_{57}$N$_9$O$_{18}$: 891.4. found: 892.3 (M+H)$^+$.

Synthesis of 69

5-Fluoropentyne 0.001M in THF (1.9 mg, 0.022 mmol) was added to a solution containing compound 68 (5 mg, 0.011 mmol), sodium ascorbate (20 mg, 0.101 mmol), and copper (II) sulfate (4.48 μL, 1.121 μmol) in DMF (112 μL)/Water (56.0 μL). The reaction was stirred for 1 hour. The reaction was diluted with water, filtered, and purified the filtrate using semi-prep HPLC to afford 69 (1 mg, 1.02 μmol, 18.24% yield). Mass Spec (lo-res): Calc'd for C$_{40}$H$_{64}$FN$_9$O$_{18}$: 977.4. found: 978.3 (M+H)$^+$.

A further list of exemplary standards are shown in Table 1, many of which may be made analogously to the methods of Examples 1-13: (Compound 70 disclosed as SEQ ID NO: 43 and Compound 71 disclosed as SEQ ID NO: 44)

| Compound | Chemical Structure | Mol. Wt. |
|---|---|---|
| 70 | 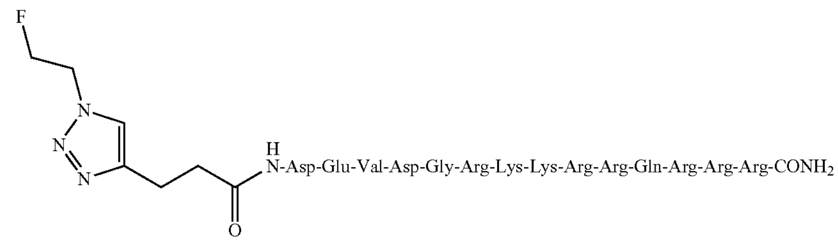 | 2022.13 |
| 71 | 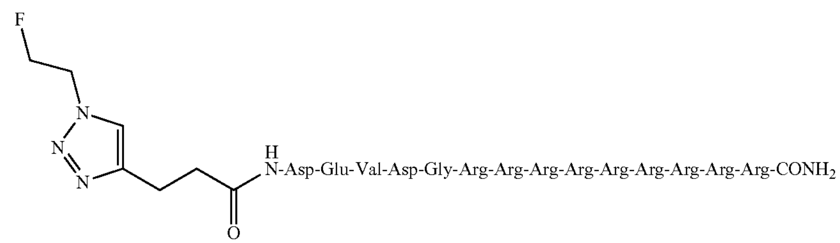 | 2106.19 |
| 72 | 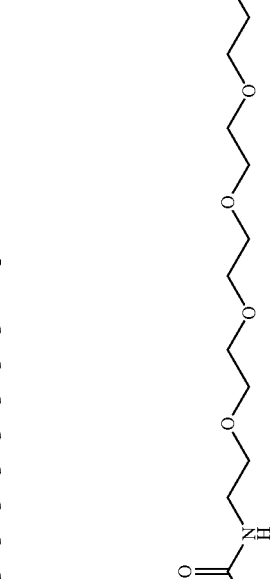 | 977.44 |

-continued

| Compound | Chemical Structure | Mol. Wt. |
|---|---|---|
| 73 | 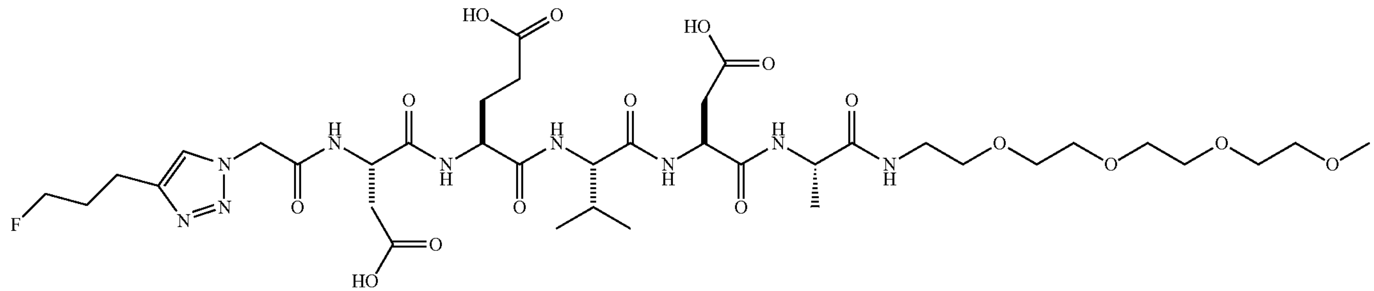 [SMILES: COCCOCCOCCOCCNC(=O)[C@H](C)NC(=O)[C@H](CC(=O)O)NC(=O)[C@@H](NC(=O)[C@H](CCC(=O)O)NC(=O)[C@H](CC(=O)O)NC(=O)Cn1cc(CCCF)nn1)C(C)C] | 905.41 |
| 74 | 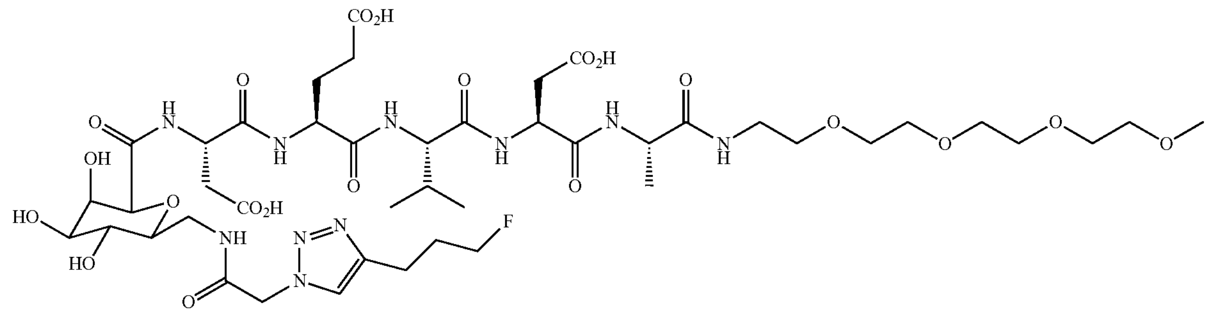 [SMILES: COCCOCCOCCOCCNC(=O)[C@H](C)NC(=O)[C@H](CC(=O)O)NC(=O)[C@@H](NC(=O)[C@H](CCC(=O)O)NC(=O)[C@H](CC(=O)O)NC(=O)C1OC(CNC(=O)Cn2cc(CCCF)nn2)C(O)C(O)C1O)C(C)C] | 1094.48 |
| 75 | 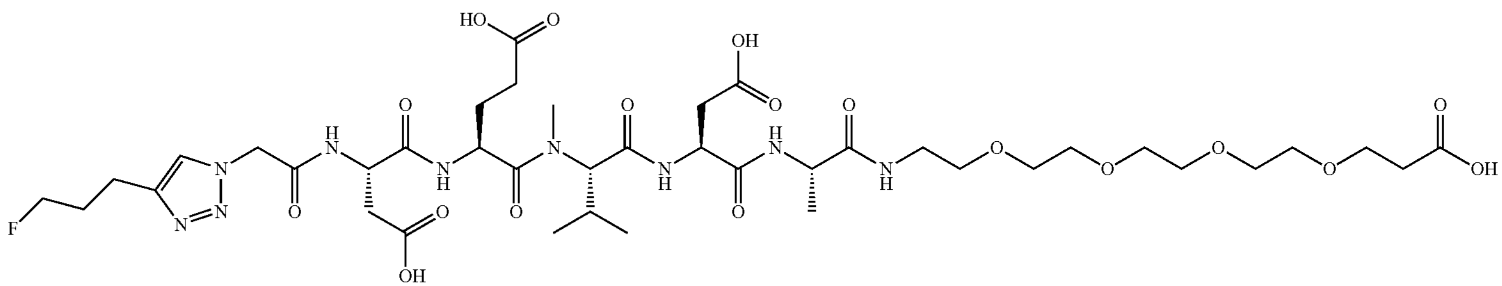 [SMILES: CC(C)[C@@H](C(=O)N[C@@H](CC(=O)O)C(=O)N[C@@H](C)C(=O)NCCOCCOCCOCCOCCC(=O)O)N(C)C(=O)[C@H](CCC(=O)O)NC(=O)[C@H](CC(=O)O)NC(=O)Cn1cc(CCCF)nn1] | 977.44 |

| Compound | Chemical Structure | Mol. Wt. |
|---|---|---|
| 76 | 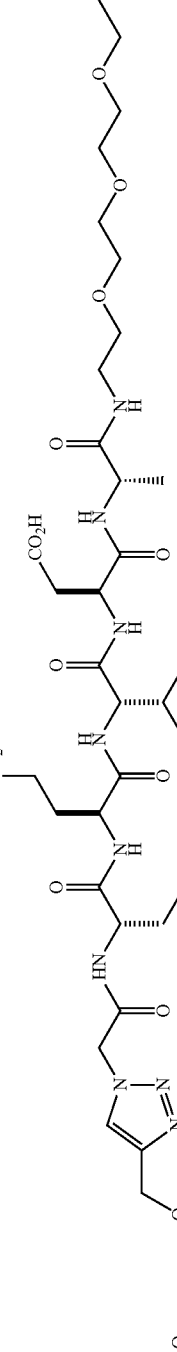 | 992.45 |
| 77 | 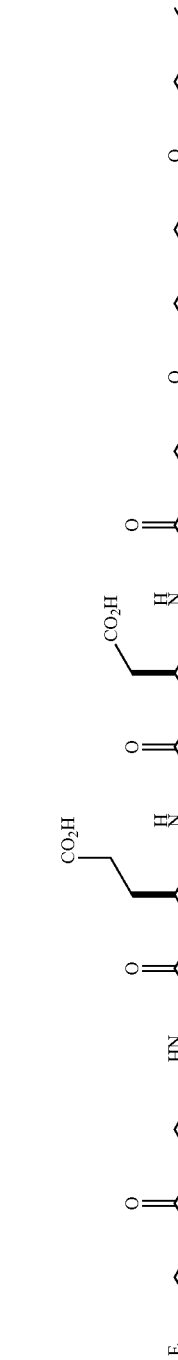 | 881.40 |
| 78 | 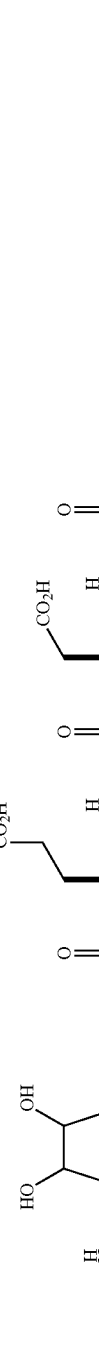 | 955.40 |

Example 14

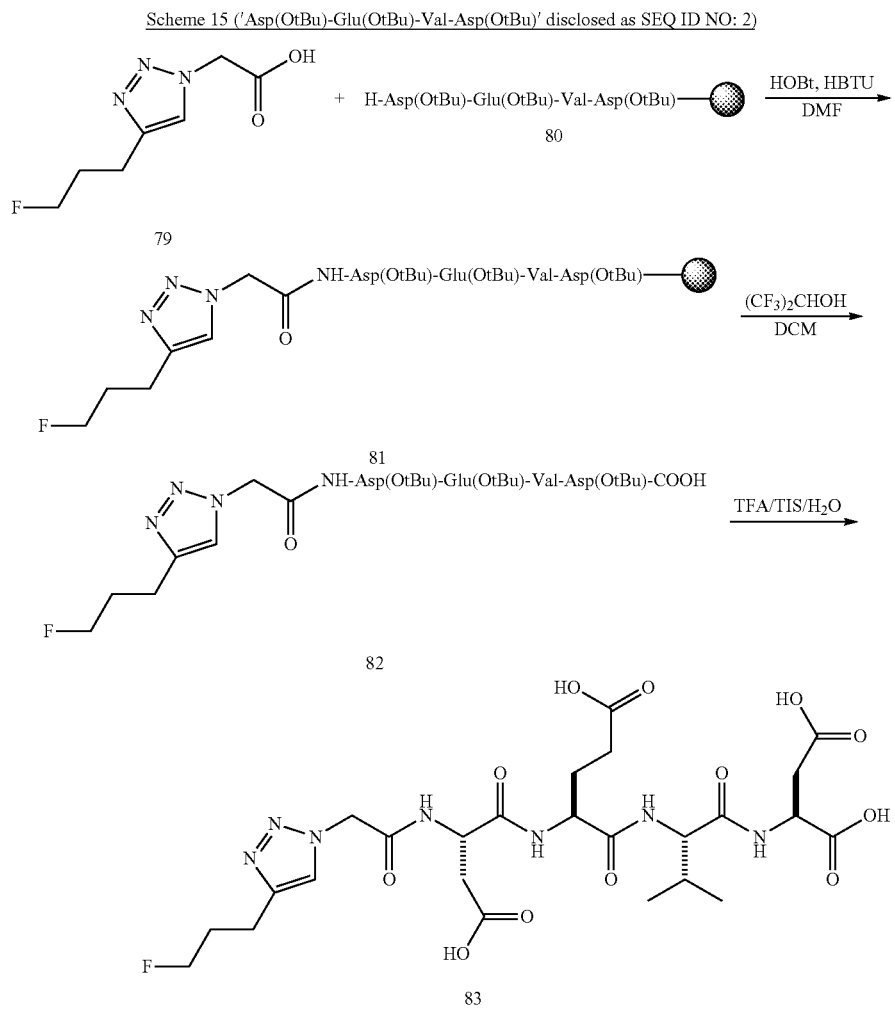

Scheme 15 ('Asp(OtBu)-Glu(OtBu)-Val-Asp(OtBu)' disclosed as SEQ ID NO: 2)

Synthesis of 81

To a solid phase reaction vessel DEVD-Cl-Trt-Resin ('DEVD' disclosed as SEQ ID NO: 2) (200 mg, loading 0.43 mmol/g) was suspended in a solution of 2-(4-(3-fluoropropyl)-1H-1,2,3-triazol-1-yl)acetic acid (32 mg, 0.172 mmol, 2 equiv), HBTU (65 mg, 0.172 mmol, 2 equiv), HOBt (23 mg, 0.172 mmol, 2 equiv) and N,N-diisopropylethylamine 2,4,6-collidine (0.27 ml, 2.04 mmol) in DMF (5 ml) for 15 h. The solution was drained and the resin was washed with DMF (3×10 ml), MeOH (2×10 ml) and DCM (3×10 ml). The success of the coupling was assessed by performing a TNBS test.

Synthesis of 83

To a solid phase reaction vessel 81 (200 mg, loading 0.43 mmol/g) was suspended in a solution of 1,1,1,3,3,3-hexafluoropropan-2-ol (20%) in DCM (5 ml) for 2 h. The solution was drained and the resin was washed with DCM (3×10 ml). The filtrate was collected and evaporated in vacuo. To the residue was added TFA:TIS:Water (ratio 95:2.5:2.5, 10 ml). After 30 min, the reaction was concentrated, and dissolved in water, filtered (0.45 urn) and purified by HPLC to afford product (41 mg, 74% yield). Mass Spec (lo-res): Calc'd for $C_{25}H_{36}FN_7O_{12}$: 645.24. found: 646.2 (M+H).

Example 15

Description of 18F—Labeling Process and Process Controls for [F-18] Tracers

Cu(I) catalyzed 'click chemistry' can be used to prepare [18F]-radiolabeled substrate analogs for Examples 1-14 For example, the [18F]-fluoroalkyne may be prepared using corresponding tosylated alkyne as precursor. Conjugation of [18F]fluoroalkyne to the substrate that is derivatized with azido group (the precursors to the exemplary standards shown in examples 1-14, for example) via Cu(I) mediated 1,3-dipolar cycloaddition yields the desired [18F]-labeled products with good yields and excellent radiochemical purity.

Figure 2:
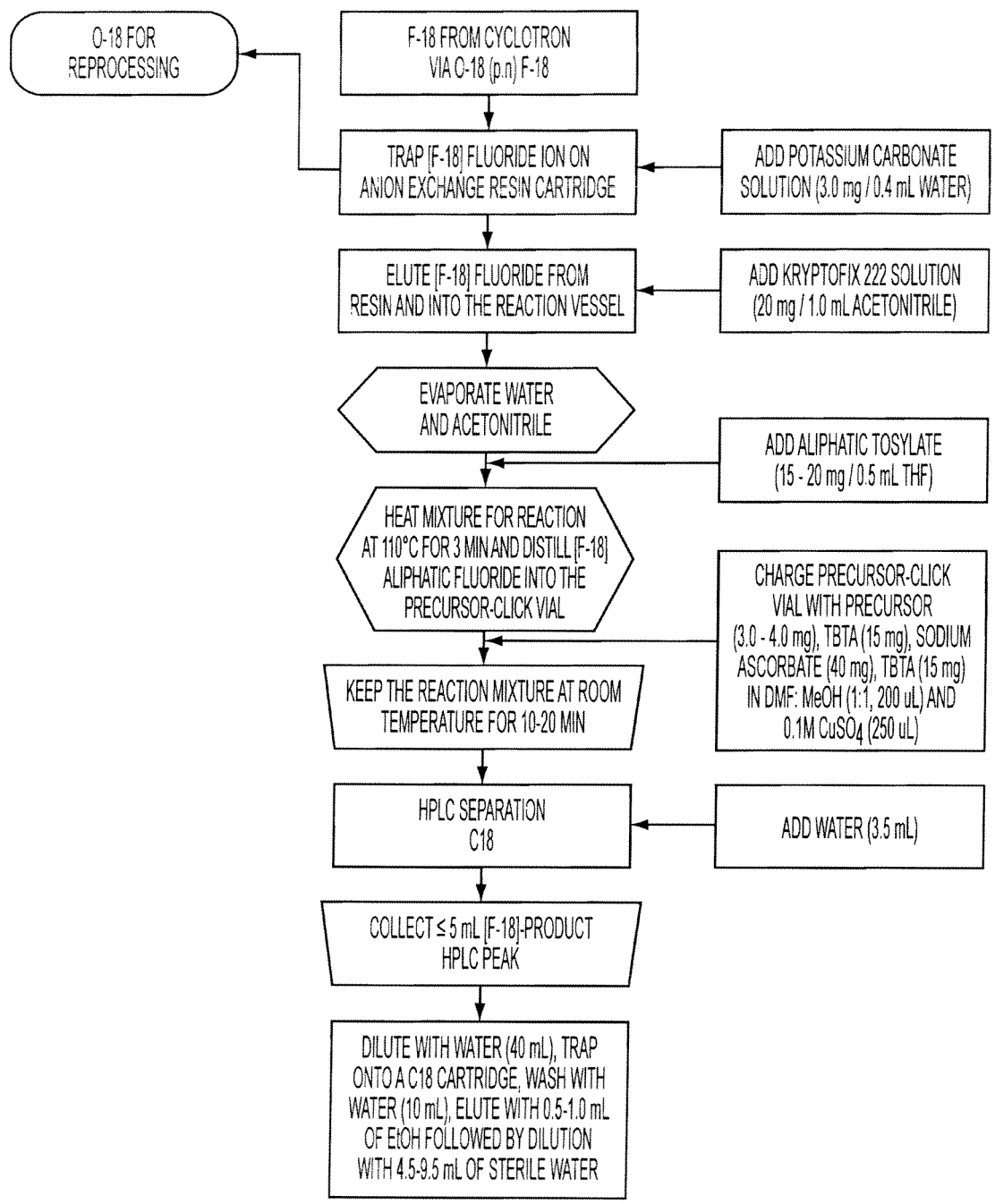
FIG. 2 is a flow chart summarizing the general radiolabeling process and process controls for production of the radiotracers.

A general discussion of each step follows the flow chart as shown in FIG. 2. While the automated synthesis procedure is the method preferred, the entire process can be run manually inside of a shielded isolator using remote handling tools.

A typical labelling sequence is shown in Scheme 16. Briefly, an [F-18] intermediate is prepared and conjugated to an elaborated precursor scaffold to afford the final [F-18]-labeled product. In this particular example, the conjugation is effected via click chemistry.

Kryptofix® 222. The use of TBA-HCO$_3$ to generate [F-18] ThAF to perform $^{18}$F-labeling reactions is well known in the art.

Scheme 16

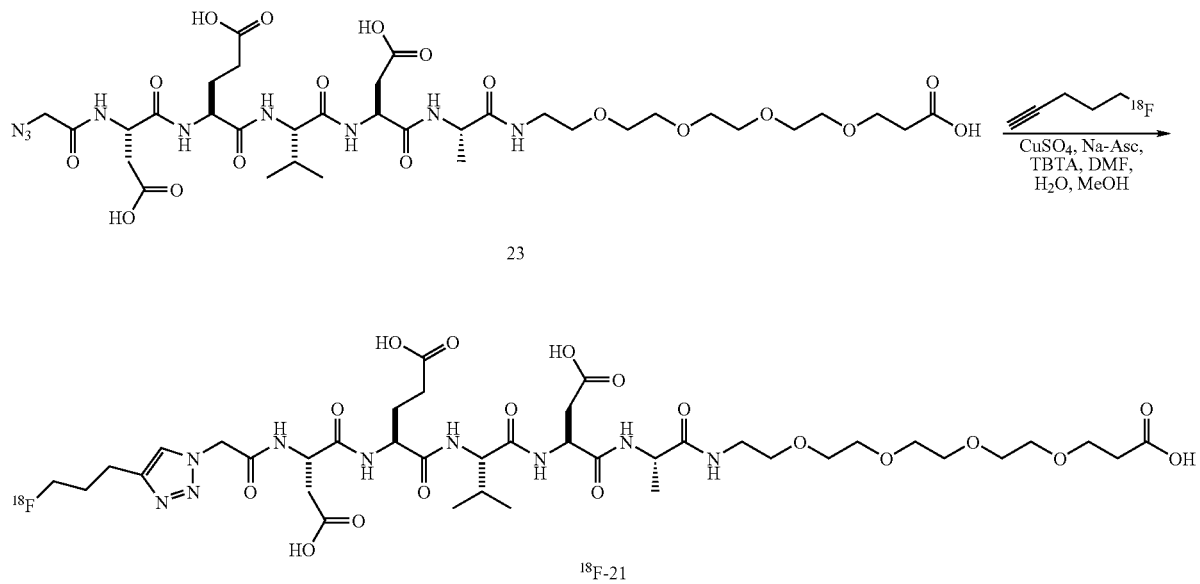

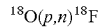

Process for the production of [F-18] fluoride ion Fluorine-18 [F-18] is produced by proton bombardment of the stable isotope, oxygen-18 (O-18) as illustrated by the reaction scheme below:

$^{18}$O(p,n)$^{18}$F

For bombardment, the chemical form of the enriched O-18 is [O-18]H$_2$O. The [F-18]Fluorine produced is aqueous [F-18]fluoride ion. The target water is loaded into an approximately 1-2 mL target and pressurized to approximately 350 psi. The tantalum target body is outfitted with a high strength, durable metal foil. The foil is an alloy referred to as, "Havar®". The major components of Havar® are cobalt, nickel, chromium, and iron. This thin Havar® foil window permits entry of the protons, yet is sufficiently durable to withstand the pressurized water and proton irradiation. Both targets are made of tantalum metal and are used exclusively for the production of F-18.

After proton bombardment, the [O-18]H$_2$O containing the [F-18]fluoride ion is transferred to a shielded enclosure ("hot cell"). The aqueous [F-18]Fluoride is then separated from the [O-18]H$_2$O.

Extraction of [F-18]Fluoride and Conversion to Anhydrous Form Aqueous [F-18]Fluoride ion produced in the cyclotron target, as described in the preceding Section, is passed through an anion exchange resin cartridge. The [O-18]H$_2$O readily passes through the anion exchange resin while [F-18] fluoride is retained. The [F-18]fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18]fluoride mixture in the reaction vessel. The Kryptofix sequesters the potassium ions preventing the formation of strong K$^+$/F on-pairs. This increases the chemical reactivity of the [F-18]fluoride ions. Alternatively, TBA-HCO$_3$ may be used in place of potassium carbonate and The mixture is dried by heating between 70-95° C. under a stream of inert gas and/or reduced pressure (250 mbar) and additional aliquots of acetonitrile may added to insure the fluoride mixture is sufficiently dry for fluorinations. This evaporation step removes the water and converts the [F-18] to an anhydrous form, which is much more reactive than aqueous [F-18]fluoride.

Reaction of Anhydrous [F-18]Fluoride with pentyne tosylate A solution of the tosylate precursor, (20 mg±5 mg, 75 µmol) dissolved in a polar aprotic solvent compatible with 18F-fluorination such as DMSO, tetrhydrofuran, DMF or MeCN (0.5 mL) is added to the reaction vessel containing the anhydrous [F-18]Fluoride. The vessel is heated to approximately 110±5° C. for 3 minutes to induce displacement of the tosylate leaving group by [F-18]fluoride as illustrated in Scheme 17. The $^{18}$F-fluoropentyne is distilled from the reaction vessel into the mixture containing a precursor. This distillation may begin as soon as the tosylate is added to the reaction mixture.

Scheme 17. Anhydrous [F-18] Fluoride Displacement Reaction with Pentynyl Tosylate

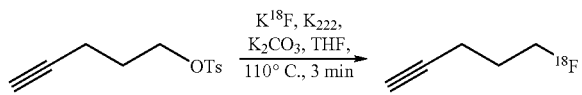

General coupling of 18F-fluoropentyne with precursors to prepare a labelled [F-18]-product The 18F-pentyne is distilled into a solution containing a precursor (3.0-4.0 mg) dissolved in 200 uL of DMF:MeOH 1:1, TBTA (15 mg), sodium ascorbate (40 mg), and 250 µL of 0.1 M $CuSO_4$. The reaction is allowed to react at room temperature for 10-20 min. Prior to purification by HPLC, the reaction is diluted with water (3.5 mL) for loading onto a 4 mL HPLC load loop.

HPLC Purification of [F-18]-Products

The reaction mixture containing the crude [F-18]-product is transferred to the HPLC sample loop and purified via chromatographic separation using a semi-preparative HPLC column (Either ACE C18 Pyramid, 7μ, 250×10 mm, Phenomenex Luna, C18, 5μ, 10×250 mm, Phenomenex Gemini C18, 250×10 mm or Phenomenex Synergi Hydro-RP C18, 250×10 mm, using a gradient system, up to 5.5 mL/min, however lower flow rates may be used if there is a high backpressure, or the system may start at a lower flow rate and then increase to the maximum flowrate). The column effluent is monitored using UV (254 or 280 nm) and radiometric detectors connected in series. The purified [F-18]-product tracer is collected from the column at the retention time window determined for the corresponding CP reference standard which coincides with the time that the radiometric detectors begin showing the main peak. The retention time of the [F-18]-products in this system varies between approximately 20-40 minutes.

Two different gradients are used depending on which [F-18]-product is prepared. The two different gradients are listed below.

Gradient 1:

| Time | % MeCN w/ 0.05% TFA | % $H_2O$ w/ 0.05% TFA |
|---|---|---|
| 7 min | 0% | 100% |
| 5 min | 5% | 95% |
| 5 min | 10% | 90% |
| 5 min | 15% | 85% |
| 5 min | 20% | 80% |
| 5-10 min (depending on when the product elutes) | 25% | 75% |
| 10 min (flushes 18F-pentyne from the column) | 95% | 5% |

Gradient 2:

| Time | % MeCN w/ 0.05% TFA | % $H_2O$ w/ 0.05% TFA |
|---|---|---|
| 0 | 5% | 95% |
| 3 | 5% | 95% |
| 15 | 50% | 50% |
| 30 | 95% | 5% |
| 35 | 5% | 95% |
| 40 | Stop | Stop |

General Formulation, Sterile Filtration and Aseptic Filling of Purified [F-18]-Products The purified [F-18]-product fraction eluted from the HPLC purification column is diluted with water (40-100 mL) and captured onto a C18 SepPak cartridge. The C18 SepPak cartridge is washed with water (10 mL) followed by elution of the product with 0.5-1.0 mL of EtOH. The sample is then diluted with sterile water (4.5-9.0 mL of water) to afford a final formulation of [F-18]-product in a maximum of 10% EtOH:water. For preparation of sterile doses, the final solution is filtered through a sterile 0.22 um filter.

High Pressure Liquid Chromatography (HPLC) Analysis of the Final Product

Mobile phase: A—0.05% TFA in Acetonitrile; B—0.05% TFA in Deionized Water

Flow rate: 1 mL/min

Gradient Program:

| Time (minutes) | % A (0.05% TFA in ACN) | % B (0.05% TFA in Water) |
|---|---|---|
| 0 | 5 | 95 |
| 3 | 5 | 95 |
| 15 | 50 | 50 |
| 30 | 95 | 5 |
| 35 | 5 | 95 |

| HPLC System Component | Manufacturer |
|---|---|
| Quaternary Pump | Agilent |
| Injector, Autosampler | Agilent |
| UV Detector | Agilent |
| Radiation Detector | Raytest |
| Column | Phenomenex |
| Data Acquisition System | Raytest |

Labeling Results:

| Tracer cmpd | Synthesis time (min) | % Yield$_{decay\ corrected}$ | SA (Ci/umol) | % RCP | Vol (mL) | $RT_{semiprep}$ | $RT_{analytical}$ | #runs | Gradient |
|---|---|---|---|---|---|---|---|---|---|
| $^{18}$F-83 | 90 min | 2% | >1.0 | >99% | 5 | 28 min | 10.5 min | 1 | 1 |
| $^{18}$F-21 | 90 min | 44% | 2.0-5.0 | >99% | 5 | 25-30 min | 11.7 min | 5 | 1 |
| $^{18}$F-27 | 120 min | 1% | >1.0 | >95% | 5 | 19 then 14 min | 10 min | 1 | 1 then 2 |
| $^{18}$F-30 | 180 | 0.4% | >0.5 | 99% | 1 | 17 min | 7.0 min | 2 | 1 |
| $^{18}$F-49 | 90 min | 20% | >2.0 | >99% | 5 | 22 min | 8.8 min | 1 | 1 |
| $^{18}$F-56 | 90 min | 19% | >2.0 | >99% | 5 | 32 min | 11 min | 3 | 1 |

Example 16
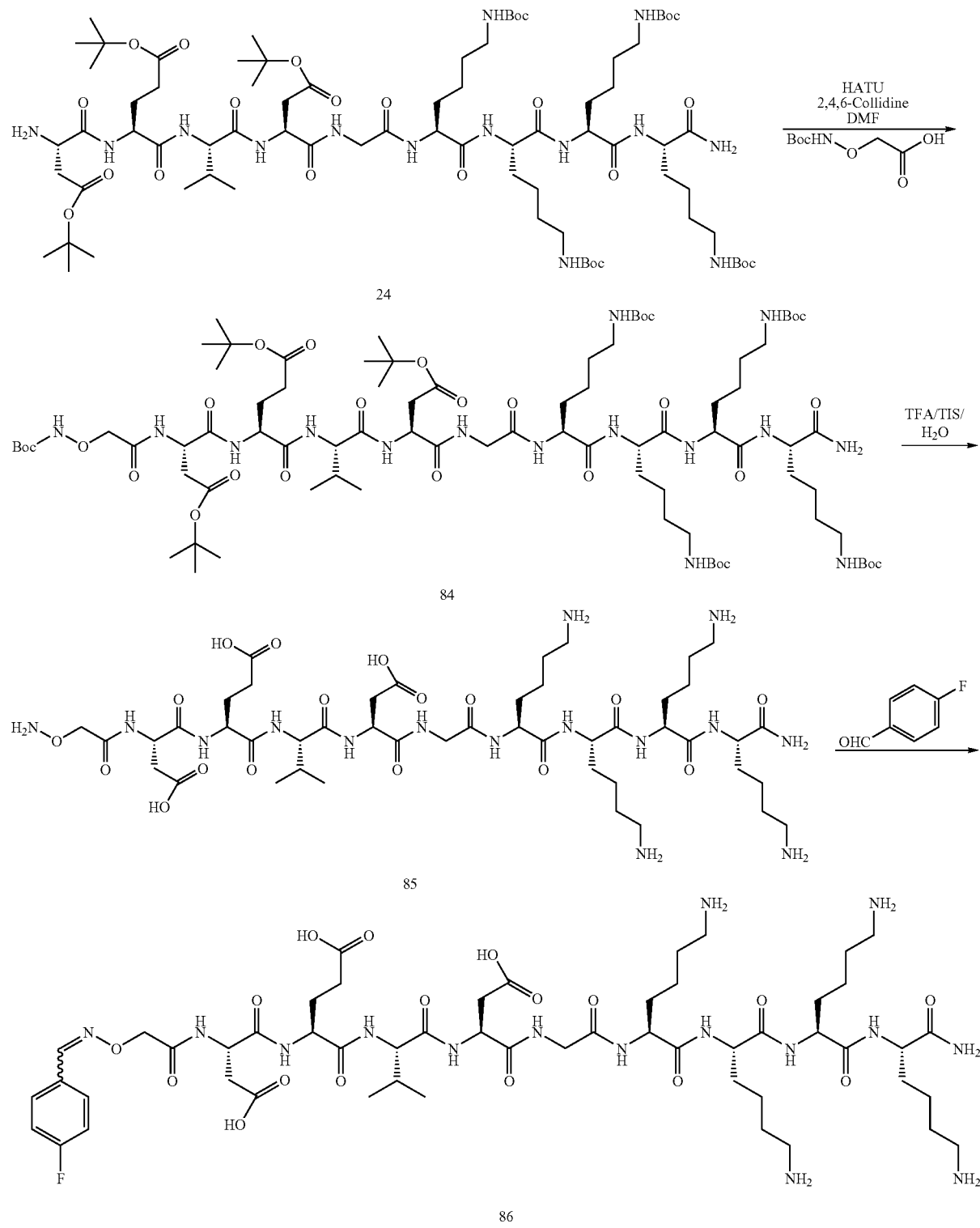
Synthesis of 84
HATU (0.071 g, 0.186 mmol) was added to a solution containing 2-(tert-butoxycarbonylaminooxy)acetic acid (0.036 g, 0.186 mmol) and 2,4,6-collidine (0.041 ml, 0.310 mmol) in DMF (5 mL). The reaction was stirred for 5 minutes. Compound 24 (0.2 g, 0.124 mmol) was added to the reaction mixture and stirred for 30 mins. The mixture was then diluted with water and filtered. Compound 84 was isolated (0.2 g, 0.112 mmol, 90% yield) as a crude white solid. Mass Spec (lo-res): Calc'd for $C_{83}H_{147}N_{15}O_{27}$: 1786.1. found: 793.9 [(M-2Boc)/2+1]$^+$.

Synthesis of 85

TFA (1 mL) was added to the compound 84 (0.2 g, 0.112 mmol). The mixture was stirred for 10 mins and concentrated. The residue was redissolved in water and purified by semi-prep HPLC to afford compound 85 (0.05 g, 0.041 mmol, 36.3% yield) as a white solid. Mass Spec (lo-res): Calc'd for $C_{46}H_{83}N_{15}O_{17}$: 1117.6. found: 1118.4 (M+H)$^+$.

Synthesis of 86

4-Fluorobenzaldehyde (0.017 mL, 3.48 mop was added to a solution containing compound 85 (3.9 mg, 3.16 mop in water (0.013 mL) and MeOH (0.051 mL). The reaction was heated to 60° C. for 30 mins. The mixture was then purified using semi-prep HPLC to afford 86 (1.5 mg, 1.225 μmol, 38.7% yield) as a white solid: $^1$H NMR (400 MHz, D$_2$O) δ: 4.63-4.56 (m, 2H), 4.53-4.50 (m, 1H), 4.46 (s, 2H), 4.27-4.24 (m, 1H), 4.15-4.04 (m, 4H), 3.93-3.90 (m, 1H), 3.79-3.69 (m, 2H), 2.84-2.78 (m, 8H), 2.75-2.64 (m, 3H), 2.34-2.20 (m, 2H), 1.93-1.75 (m, 3H), 1.70-1.45 (m, 15H), 1.35-1.18 (m, 8H), 0.74 (in, 3H). Mass Spec (lo-res): Calc'd for $C_{53}H_{86}FN_{15}O_{17}$: 1223.6. found: 1224.4 (M+H)$^+$.

Alternatively, the precursor compound 85 may be converted to the radiolabeled analog via treatment with $^{18}$F-4-fluorobenzaldehyde.

Example 17

Scheme 19

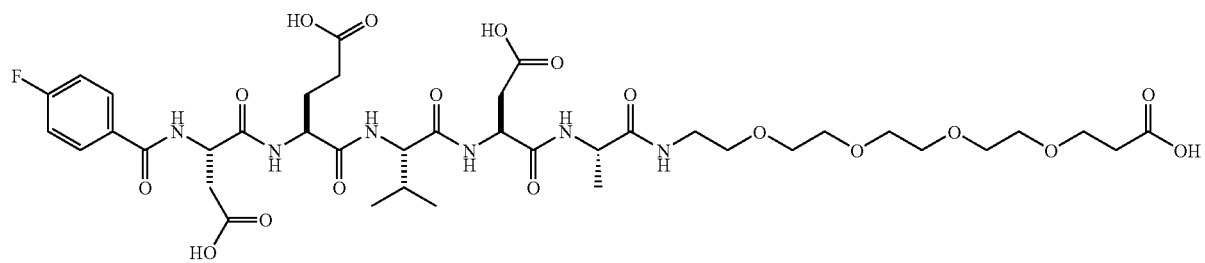

86

A further list of exemplary imaging agent standards is shown in Table 2, many of which may be made analogously to the methods described in Examples 1-16:

| Compound | Chemical Structure | Mol. Weight |
|---|---|---|
| 87 | 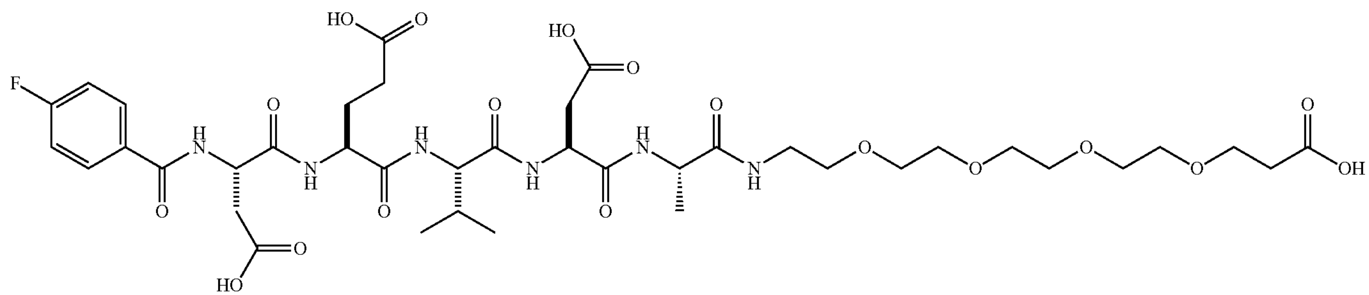 [SMILES: CC(C)[C@H](NC(=O)[C@H](CCC(=O)O)NC(=O)[C@H](CC(=O)O)NC(=O)c1ccc(F)cc1)C(=O)N[C@@H](CC(=O)O)C(=O)N[C@@H](C)C(=O)NCCOCCOCCOCCOCCC(=O)O] | 916.37 |
| 88 | 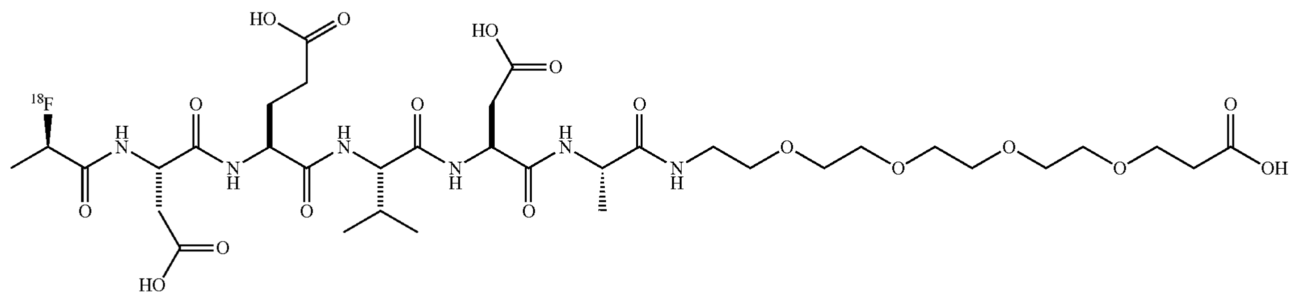 [SMILES: CC(C)[C@H](NC(=O)[C@H](CCC(=O)O)NC(=O)[C@H](CC(=O)O)NC(=O)[C@@H](C)[18F])C(=O)N[C@@H](CC(=O)O)C(=O)N[C@@H](C)C(=O)NCCOCCOCCOCCOCCC(=O)O] | 868.37 |

Example 18

Caspase-3 Activity Assay

The enzymatic activity of the caspase-3 was determined by measuring the accumulation of the cleaved fluorogenic product AFC (7-amino-4-trifluoromethylcoumarin). Caspase-3 cleaves the tetrapeptide between D and AFC, thus releasing the fluorogenic AFC which can be quantified by U.V. spectrofluorometry. The enzyme and substrate, cell lysate or tissue homogenate were diluted in assay buffer containing 150 mM NaCl, 50 mM HEPES, 5 mM EDTA, 1 mM DTT, 10% glycerol, pH 7.0. After mixing the reaction reagents, the caspase 3 activity is measured by UV spectrofluorometry at 37° C.

Caspase activities in tumors from mice with dual tumor implants is shown in Table 3. The caspase-3 activity is expressed in mU and normalized by protein concentration (for cell lysate or tissue).

TABLE 3

The caspase-3 activity is expressed in mU and normalized by protein concentration (for cell lysate or tissue).

| | Animal ID | | | |
|---|---|---|---|---|
| | H12120815 | H12120816 | H12120817 | H12120818 |
| HT29 | 650.5 | 2849.2 | 3244.4 | 1648.7 |
| U87 | 2101.4 | 807.5 | 1593.1 | 950.1 |
| muscle | 49.2 | 48.9 | 22.7 | 17.34 |

Example 19

Caspase Substrate Cleavage Measured Using Mass Spectrometry Quantification

The caspase substrate cleavage was determined by measuring the accumulation of the cleaved product or the reduction of substrate, which were measured by mass spectrometry. The substrate and caspase-3 enzyme are mixed in assay buffer (150 mM NaCl, 50 mM HEPES, 5 mM EDTA, 1 mM DTT, 10% glycerol, pH 7.0.). At different time points, the amounts of substrate or cleaved product were measured by MS. The cleavage rate of substrate is expressed by a percentage of cleaved substrate vs. total substrate per hour per unit caspase-3 enzyme.

Caspase substrate cleavage of tracer compounds $^{18}$F-21, $^{18}$F-63 and $^{18}$F-69 is shown in FIG. 3.

Example 20

Protocol of [18F]-Tracer Compound Uptake in Cancer Cell Lines

Cells grown overnight and having reached about 80% confluence in 6-well plates were exposed to 1 mM of apoptotic inducer 5FU for 2 days in a cell culture incubator. The [18F]-labeled tracer was added into each well (triplicates for control and 5FU treated) at 10 µCi/well. (in case of experiments involving the use of caspase-3 inhibitors as blockers, the inhibitor was added to the cells 1 hour before the addition of the [18F]-tracer). The cells were then incubated for two hours. Cells were collected by scrape and centrifugation. Cell pellets were washed twice with 1λ PBS. The amount of tracer inside the cells and in the medium was measured by γ-counter. The % Uptake=total CPM inside cells/total tracer CPM×100%. The % Uptake was normalized by the amount of cellular protein extract (mg): % uptake/mg protein extracts.

Results for cell lines U87, A498 and HT29 for four tracers are shown in Table 4.

TABLE 4

Examples of percent uptake for tracers in cell lines U87, A498, and HT29.

| Tracer | U87 | A498 | HT29 |
|---|---|---|---|
| $^{18}$F-21 | 2.1 | 1.8 | 2.1 |
| $^{18}$F-30 | 1.4 | 1.6 | 1.1 |
| $^{18}$F-49 | | 1.5 | |
| $^{18}$F-56 | 2.1 | 2.1 | 1.9 |

Example 21

Protocol of Cold [19F] Standard Compound Uptake in Cells Treated with Apoptotic Inducer When cells grown in 6-well plates reached 80% confluence, the growth medium was replaced with 2 ml of fresh medium containing 1 mM of 5FU. After two days of apoptotic induction, the standard compound was added into the cultures (control and 5FU treated) at a final concentration of 10 µM. The cells were cultured in the incubator for 2 hours for compound uptake. Then, (in the case of experiments involving the use of caspase-3 inhibitors as blockers, the inhibitor was added to the cells 1 hour early before the addition of standard compound). 100 µl of cell culture medium for each sample was collected, and the cells were harvested by centrifugation. Cell pellets were washed twice with 1×PBS, and lysed in 100 µl of lysis buffer. Both cell lysate and medium were boiled for 5 minutes to denature proteins, cooled down on ice, then 100 µl of chloroform/methanol (50/50 ratio) were added. After vortexing and extraction, the samples were centrifuged in Eppendorf tubes in a micro centrifuge at 13000 rpm for 15 minutes at 4 C. 50 µl of the supernatant was transferred to an HPLC vial. The amounts of compound (or product of caspase-3 cleavage) inside the cells and in the medium were measured by LC/MS. The % uptake=total amount of cell uptake/total amount of compound X 100%. The % uptake was normalized by the amount of cellular protein extract (mg): % Uptake/mg protein extracts.

Results for cell lines U87 and A498 for four compounds are shown in Table 5.

TABLE 5

Examples of percent uptake for compounds in cell lines U87, A498, and HT29.

| Compound | U87 | A498 | HT29 | H2122 |
|---|---|---|---|---|
| 21 | 2.0 | 2.1 | 1.1 | 1.3 |
| 27 | 2.5 | 4.5 | 1.7 | 2.0 |
| 49 | 2.9 | 3.5 | | |
| 56 | 2.1 | 2.0 | | |

Example 22

PET Study Protocol: In Vivo microPET Imaging of a Mouse is Performed on an Anesthetized Fox1$^{nu}$ (Homozygous Nu/Nu) Mouse after Administration of the Compounds of the Invention All animals are implanted subcutaneously with tumor cells. Mice are selected for study based on their tumor volume and type. Mice with tumors between approximately 1 and 1.5 cm³ placed into groups such that the median tumor volume is approximately the same for all animals. Animals considered suitable for study (tumor volumes within the assigned volume range) have their tumors measured prior to treatment.

The general study design is outlined in Table 5.

TABLE 5

General study design for PET imaging.

| Mice | Test Compound | ¹⁸F activity | Dose volumes | Dose Route | Endpoints PET Scanning |
|---|---|---|---|---|---|
| 1 | Test Compound Single Bolus | ~250 µCi | 200 µL (maximum) | Intravenous | 1-2 hour dynamic scan |

Various human cancer cell lines were used as received from ATCC (American Type Culture Collection). The tumor line cells were grown in cell culture medium according SBR cell culture SOPs and ATCC recommendations.

Cell Implantation

Tumor cells were counted by the trypan blue exclusion method, according to SBR procedures. Approximately 5-10 million cells per mouse were implanted subcutaneously in a volume of approximately 0.2 mL sterile Phosphate Buffered Saline (PBS).

Antemortem Study Evaluations

Positron Emission Tomography/Computed Tomography (PET/CT) Scanning

Following the administration of the test imaging compound, the animals are then subjected to a PET scan. The resulting data is analyzed to assess the uptake of the test compound by the xenograft tumors. Animals are induced with 5% isoflurane/oxygen until anesthetized then maintained on 2-2.5% isoflurane/oxygen inhalation for the duration of each PET/CT scanning procedure (up to 2 hours). Anesthetized animals are placed on a heated pad for the duration of each PET/CT scan.

Description of Positron Emission Tomography

Dose Level

~250 µCi per animal per scan

Dose Volume

A maximum dose volume of 200 µL

Continuous, dynamic PET scanning commenced immediately following administration of the F18-Test Imaging Compound. The expected duration of scanning is up to 2 hours. The data was analyzed to assess the uptake % ID/g (percent injected dose per gram) and T:M (tumor to muscle ratio) of the Test Imaging Compound by the xenograft tumors. Exemplary results are shown in Table 6.

Method of Euthanasia

Euthanasia was carried out via carbon dioxide inhalation followed by exsanguination, unless specified otherwise.

TABLE 6

Examples of tumor to muscle rations after imaging with caspase tracers [18F]-49 and [18F]-21.

| Tracer | tumor | tumor/muscle ratio | tumor size (cm3) |
|---|---|---|---|
| [18F]-49 | A498 | 4.35 | 0.52 |
| | A498 | 3.16 | 0.47 |
| | A427 | 4.11 | 0.25 |
| | A427 | 3.04 | 0.25 |

TABLE 6-continued

Examples of tumor to muscle rations after imaging with caspase tracers [18F]-49 and [18F]-21.

| Tracer | tumor | tumor/muscle ratio | tumor size (cm3) |
|---|---|---|---|
| | A427 | 6.71 | 0.23 |
| [18F]-21 | A431 | 4.54 | 0.52 |
| | A498 | 2.48 | 0.52 |
| | A498 | 2.73 | 0.62 |
| | A498 | 2.97 | 1.75 |
| | A498 | 6.84 | 1.76 |
| | A498 | 2.63 | 1.76 |
| | A498 | 4.29 | 1.76 |

In vivo microPET imaging shows that the compounds of the invention are very good tracers with good tumor uptake and retention and a fast wash-out rate from muscle and other healthy tissues.

The imaging agents prepared as provided herein are similarly administered to a mouse, and microPET imaging experiments using the mouse show that the compounds prepared are effective tracers and also provide good tumor uptake and retention, and also a fast wash-out rate from muscle and other healthy tissues.

The embodiments of the invention and the various features and advantageous details thereof are explained more fully with reference to the non-limiting embodiments and examples that are described and/or illustrated in the accompanying drawings and detailed herein. It should be noted that the features of one embodiment may be employed with other embodiments as the skilled artisan would recognize, even if not explicitly stated herein. The examples used herein are intended merely to facilitate an understanding of ways in which the invention may be practiced, and to further enable those of skill in the art to practice the embodiments of the present application. Accordingly, the examples and embodiments herein should not be construed as limiting the scope of the application.

All references cited herein are incorporated by reference as if each had been individually incorporated by reference in its entirety. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The herein described embodiments may be modified or varied, without departing from the scope or spirit of the invention, as appreciated by those skilled in the art in light of the above teachings and references incorporated herein. It is therefore to be understood that, within the scope of the claims and their equivalents, the invention may be practiced otherwise than as specifically described.

The invention is further described by the following numbered paragraphs:

1. An imaging agent comprising a compound of formula I:

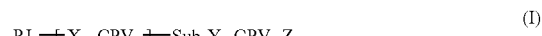

(I)

wherein:

X is a bond or a linker connected to an N-terminus of a peptide substrate;

Y is a bond or a linker;

RL is a radio label;
Sub is a peptide substrate;
CPV is a cell permeating vector;
Z is a capping group;
m, n, p, and s are independently 0-4;
t is 0 or 1; and
u is 1 or 2;
or a pharmaceutically acceptable salt thereof.

2. The imaging agent of paragraph 1 wherein,
X is a bond or a linker connected to an N-terminus of a peptide substrate;
Y is a bond or a linker;
RL is a radiolabel;
Sub is a peptide substrate;
CPV is a cell permeating vector;
Z is a capping group;
m, p, and s are independently 0-4;
n is 0;
t is 1; and
u is 1.

3. The imaging agent of paragraphs 1 or 2 wherein, $X_m$ is a bond or $X^2X^3X^4$, wherein $X^2$ is a $(C_{1-10})$alkylenyl group, aryl group or heteroaryl group, $X^3$ is a heteroaryl group or —C=N—O—, $X^4$ is a $(C_{1-10})$alkylenyl group, wherein one of the $(C_{1-10})$alkylenyl carbon atoms is optionally replaced with —CO—, —CONR"—, —NR"CO—, —NR"—, —O— or —S—;
Y is a bond or a linker;
RL is a radiolabel selected from the group consisting of $^{11}$C or $^{18}$F;
Sub is a peptide substrate selected from the group consisting of -DEVD- (SEQ ID NO: 2), -DE(N-alkyl V)D- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19), -VDVAD- (SEQ ID NO: 20), -VDVADGW- (SEQ ID NO: 21), -RGVDQQDGKNHW- (SEQ ID NO: 22), -GVDQQDGKNW (SEQ ID NO: 23), -VDQQDGKNW- (SEQ ID NO: 24), -DQQDGKNW- (SEQ ID NO: 25), -QQDGKNW- (SEQ ID NO: 26), -VDQQDGKW- (SEQ ID NO: 27), -VDQQDGW- (SEQ ID NO: 28), -VDQQDW- (SEQ ID NO: 29), -WEHD- (SEQ ID NO: 30), -YVAD- (SEQ ID NO: 5), -AEVD- (SEQ ID NO: 31), -IETD- (SEQ ID NO: 8), -AEVD- (SEQ ID NO: 31), -VEHD- (SEQ ID NO: 32), -XEXDAMC- (SEQ ID NO: 33), -DEVDAMC- (SEQ ID NO: 34), -VEHDAMC- (SEQ ID NO: 35), -VAD-FMK- (SEQ ID NO: 36), -YEVDGW- (SEQ ID NO: 37), -LEVDGW- (SEQ ID NO: 38), -VDQMDGW- (SEQ ID NO: 39), -VDVADGW- (SEQ ID NO: 21), -VQVDGW- (SEQ ID NO: 40), VDQVDGW- (SEQ ID NO: 41), -DEVDAMC- (SEQ ID NO: 34), -VD-fmk-, -VAD-fmk-, -YVAD-fmk- ('YVAD disclosed as SEQ ID NO: 5), -ID-fmk-, -LD-fmk, -FD-fmk-, -AD-fmk-, -GD-fmk-, -KD-fmk-, -ED-fmk- and -DEVDAFC- (SEQ ID NO: 42);
CPV is selected from the group consisting of polyethyleneimine, PEG, PEI-PEG, PEG-PEI, Lys4 (SEQ ID NO: 1), polyamines, histidylated poly-L-lysine, polyarginine, polyornithine, cationic liposomes and lipids, saccharide derivatives and polylysine;
Z is a capping group;
p is 0-4;
n is 0;
s is 1;
t is 1; and
u is 1.

4. The imaging agent of any of paragraphs 1-3 wherein,
$X_m$ is $X^2X^3X^4$, wherein $X^2$ is a $(C_{2-6})$alkylenyl group or aryl, $X^3$ is a heteroaryl group or —C=N—O—, $X^4$ is a $(C_{1-10})$alkylenyl group, wherein one of the $(C_{1-10})$alkylenyl carbon atoms is optionally replaced with —CO—;
Y is a bond or a linker;
RL is $^{18}$F;
Sub is a peptide substrate selected from the group consisting of -DEVD- (SEQ ID NO: 2), -DE(N-alkyl V)D- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19) and -VDVAD- (SEQ ID NO: 20);
CPV is selected from the group consisting of a polyethyleneimine, PEG, PEI-PEG, PEG-PEI, Lys4 (SEQ ID NO: 1), polyamines, histidylated poly-L-lysine, polyarginine, polyornithine, cationic liposomes and lipids, saccharide derivatives and polylysine;
Z is a capping group;
p is 0-4;
n is 0;
s is 1;
t is 1; and
u is 1.

5. The imaging agent of any of paragraphs 1-4 wherein,
$X_m$ is $X^2X^3X^4$, wherein $X^2$ is —(CH$_2$)$_2$—, $X^3$ is a triazole, $X^4$ is —CH$_2$C(O)—;
Y is a —AlaNH—;
RL is $^{18}$F;
Sub is -DEVD- (SEQ ID NO: 2);
CPV is (—CH$_2$CH$_2$O—)$_4$;
Z is —CH$_2$CH$_2$CO$_2$H;
n is 0;
s is 1;
t is 1; and
u is 1.

6. The imaging agent of paragraph 1 wherein,
X is a bond or a linker connected to an N-terminus of a peptide substrate;
Y is a bond or a linker;
RL is a radiolabel;
Sub is a peptide substrate;
CPV is a cell permeating vector;
Z is a capping group;
m, p, and n are independently 0-4;
s is 0;
t is 1; and
u is 1.

7. The imaging agent of paragraphs 1 or 6 wherein,

X. is $X^2X^3X^4$, wherein $X^2$ is $C_1$-$C_6$alkylene, $X^3$ is a heteroaryl group, $X^4$ is a $(C_{1-10})$alkylenyl group, wherein one of the $(C_{1-10})$alkylenyl carbon atoms is optionally replaced with —CO—;

Y is a bond or a linker;

RL is $^{18}$F;

Sub is a peptide substrate selected from the group consisting of -DEVD- (SEQ ID NO: 2), -DE(N-alkyl V)D- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19) and -VDVAD- (SEQ ID NO: 20); CPV is selected from the group consisting of a polyethyleneimine, PEG, PEI-PEG, PEG-PEI, Lys4 (SEQ ID NO: 1), polyamines, histidylated poly-L-lysine, polyarginine, polyornithine, cationic liposomes and lipids, saccharide derivatives and polylysine;

Z is a capping group;

p is 0-4;

n is 1;

s is 0;

t is 1; and u is 1.

8. The imaging agent of any of paragraphs 1, 6, or 7 wherein the compound of formula (I) is Y is a bond or a linker;

RL is $^{18}$F;

Sub is a peptide substrate selected from the group consisting of -DEVD- (SEQ ID NO: 2), -DE(N-alkyl V)D- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19) and -VDVAD- (SEQ ID NO: 20);

CPV is independently selected from the group consisting of a polyethyleneimine, PEG, PEI-PEG, PEG-PEI, Lys4 (SEQ ID NO: 1), polyamines, histidylated poly-L-lysine, polyarginine, polyornithine, cationic liposomes and lipids, saccharide derivatives and polylysine;

Z is a capping group;

p is 0-4;

n is 1;

s is 1;

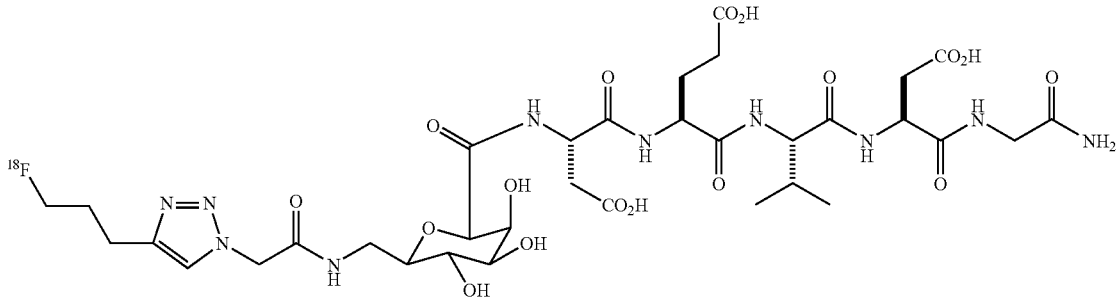 [SMILES: CC(C)[C@H](NC(=O)[C@H](CCC(=O)O)NC(=O)[C@H](CC(=O)O)NC(=O)C1OC(CNC(=O)Cn2cc(CCC[18F])nn2)C(O)C(O)C1O)C(=O)N[C@@H](CC(=O)O)C(=O)NCC(N)=O]

9. The imaging agent of paragraph 1 wherein, $X_m$ is $X^2X^3X^4$, wherein $X^2$ is $C_1$-$C_6$alkylene, $X^3$ is a heteroaryl group, $X^4$ is a $(C_{1-10})$alkylenyl group, wherein one of the $(C_{1-10})$alkylenyl carbon atoms is optionally replaced with —CO—;

t is 1; and u is 1.

10. The imaging agent of paragraphs 1 or 9 wherein the compound of formula (I) is

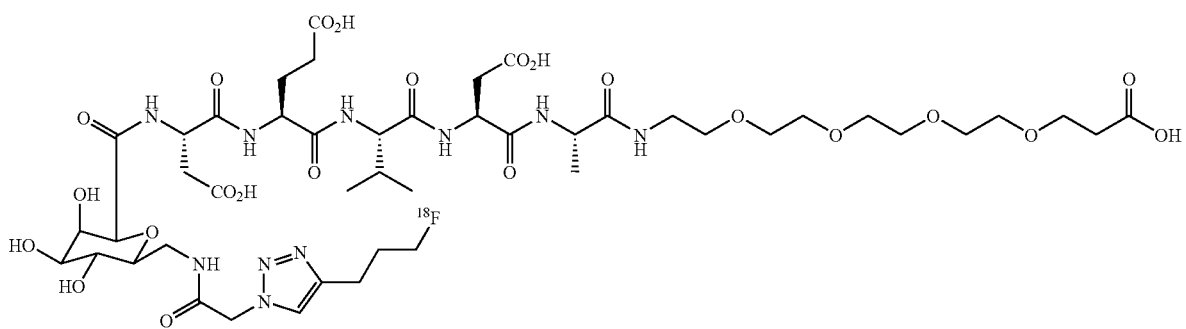 [SMILES: CC(C)[C@H](NC(=O)[C@H](CCC(=O)O)NC(=O)[C@H](CC(=O)O)NC(=O)C1OC(CNC(=O)Cn2cc(CCC[18F])nn2)C(O)C(O)C1O)C(=O)N[C@@H](CC(=O)O)C(=O)N[C@@H](C)C(=O)NCCOCCOCCOCCOCCC(=O)O]

11. The imaging agent of any of paragraphs 1-10, wherein the radiolabel is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P.

12. The imaging agent any of paragraphs 1-11, wherein the radiolabel is selected from the group consisting of $^{11}$C and $^{18}$F.

13. The imaging agent of any of paragraphs 1-12, wherein the radiolabel is a PET or SPECT based isotope.

14. The imaging agent of paragraph 13, wherein the PET or SPECT based isotope is selected from the group consisting of $^{18}$F, $^{64}$Cu and $^{99m}$Tc.

15. The imaging agent of any of paragraphs 1-14, wherein the radiolabel is linked to the substrate using click chemistry, chelation chemistry, oxime formation, or amide-based conjugation chemistry.

16. The imaging agent of any of paragraphs 1-15, wherein the substrate comprises a peptide fragment.

17. The imaging agent of paragraph 16, wherein the peptide fragment is selected from the group consisting of a dipeptide, tripeptide, tetrapeptide, pentapeptide, hexapeptide, heptapeptide, octapeptide and nonapeptide.

18. The imaging agent of paragraphs 16 or 17, wherein the peptide fragment is selected from the group consisting of -DEVD- (SEQ ID NO: 2), -DE(N-alkyl V)D- (SEQ ID NO: 2), -DEVDD- (SEQ ID NO: 9), -DNLD- (SEQ ID NO: 10), -DQTD (SEQ ID NO: 11), -DMQD- (SEQ ID NO: 12), -YVDA- (SEQ ID NO: 13), -YEVD- (SEQ ID NO: 14), -LEVD- (SEQ ID NO: 6), -LEHD (SEQ ID NO: 4), -DQMD- (SEQ ID NO: 15), VDQQD- (SEQ ID NO: 16), -VDVDA- (SEQ ID NO: 17), -VEID- (SEQ ID NO: 7), -VQVD- (SEQ ID NO: 18), -YVADGW- (SEQ ID NO: 19), -VDVAD- (SEQ ID NO: 20), -VDVADGW- (SEQ ID NO: 21), -RGVDQQDGKNHW- (SEQ ID NO: 22), -GVDQQDGKNW (SEQ ID NO: 23), -VDQQDGKNW- (SEQ ID NO: 24), -DQQDGKNW- (SEQ ID NO: 25), -QQDGKNW- (SEQ ID NO: 26), -VDQQDGKW- (SEQ ID NO: 27), -VDQQDGW- (SEQ ID NO: 28), -VDQQDW- (SEQ ID NO: 29), -WEHD- (SEQ ID NO: 30), -YVAD- (SEQ ID NO: 5), -AEVD- (SEQ ID NO: 31), -IETD- (SEQ ID NO: 8), -AEVD- (SEQ ID NO: 31), -WEHD- (SEQ ID NO: 30), -VEHD- (SEQ ID NO: 32), -XEXDAMC- (SEQ ID NO: 33), -DEVDAMC- (SEQ ID NO: 34), -VEHDAMC- (SEQ ID NO: 35), -VADFMK- (SEQ ID NO: 36), -YEVDGW- (SEQ ID NO: 37), -LEVDGW- (SEQ ID NO: 38), -VDQMDGW- (SEQ ID NO: 39), -VDVADGW- (SEQ ID NO: 21), -VQVDGW- (SEQ ID NO: 40), VDQVDGW- (SEQ ID NO: 41), -DEVDAMC- (SEQ ID NO: 34), -VD-fmk-, -VAD-fmk-, -YVAD-fmk- ('YVAD' SEQ ID NO: 5), -ID-fmk-, -L-D-fmk, -FD-fmk-, -AD-fmk-, -GD-fmk-, -KD-fmk-, -ED-fmk- and -DEVDAFC- (SEQ ID NO: 42).

19. The imaging agent of any of paragraphs 1-15, wherein the substrate comprises a nucleic acid or polynucleotide.

20. The imaging agent of any of paragraphs 1-19, wherein the cell-permeating vector is selected from the group consisting of a polyethyleneimine, PEG, PEI-PEG, PEG-PEI, (Lys)$_4$, (SEQ ID NO: 1) TAT peptide fragment, or saccharide derivative.

21. The imaging agent of any of paragraphs 1-19, wherein the cell-permeating vector is an amphiphilic moiety.

22. The imaging agent of paragraph 21, wherein the amphiphilic moiety is selected from the group consisting of polyethyleneimine, polyamines, histidylated poly-L-lysine, polyarginine, polyornithine, cationic liposomes and lipids, and polylysine.

23. A method for a imaging reporter in vivo, the method comprising contacting the imaging agent of any of paragraphs 1 to 22 to a cell and imaging the reporter in-vivo.

24. The method of paragraph 23, wherein the reporter is a protease or nuclease.

25. The method of paragraph 24, wherein the protease is Caspase 3.

26. A method for detecting or diagnosing a disease involving abnormal apoptosis in a mammal, the method comprising administering an imaging agent of any one of paragraphs 1 to 22 to the mammal, and detecting the presence of retained radioactivity in the mammal.

27. The method of paragraph 26, wherein the detecting step employs a nuclear imaging technique selected from the group consisting of positron emission tomography (PET) and single photon emission computed tomography (SPECT) for monitoring a distribution of the imaging agent within the body or within a portion thereof.

28. A method of visualizing caspase activity in a body of a patient, the method comprising: (a) administering to the patient the imaging agent of any of paragraphs 1 to 19; and (b) employing a nuclear imaging technique selected from the group consisting of positron emission tomography (PET) and single photon emission computed tomography (SPECT) for visualizing a distribution of the imaging agent within the body or within a portion thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An imaging agent represented by the structure

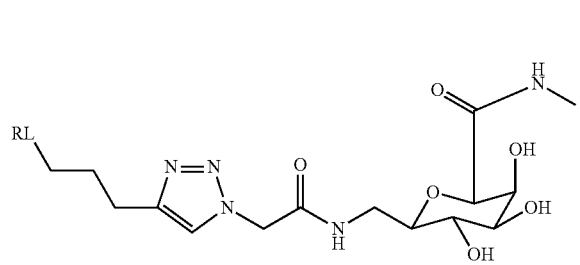

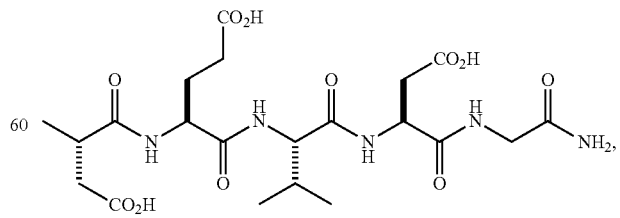

or a pharmaceutically acceptable salt thereof wherein RL is a radiolabel.

2. An imaging agent represented by the structure
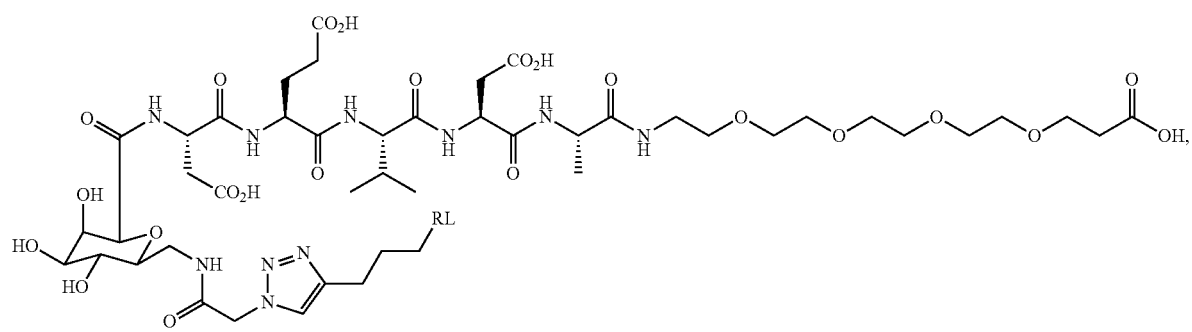
or a pharmaceutically acceptable salt thereof wherein RL is a radiolabel.
3. The imaging agent of claim 2, wherein the radiolabel is $^{18}$F.
4. The imaging agent of claim 1, wherein the radiolabel is $^{18}$F.
* * * * *

SEQUENCE LISTING

<160> NUMBER OF SEQ ID NOS: 44

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Lys Lys Lys Lys
1

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Glu Val Asp
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: May or may not be present

<400> SEQUENCE: 3

Arg Arg Arg Arg Arg Arg Arg Arg Arg
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Glu His Asp
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Val Ala Asp
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Glu Val Asp
1

<210> SEQ ID NO 7
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 7

Val Glu Ile Asp
1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Glu Thr Asp
1

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Glu Val Asp Asp
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Asn Leu Asp
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Gln Thr Asp
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Met Gln Asp
1
```

```
<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Val Asp Ala
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Glu Val Asp
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Gln Met Asp
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Asp Gln Gln Asp
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Asp Val Asp Ala
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

```
Val Gln Val Asp
1

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Val Ala Asp Gly Trp
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Asp Val Ala Asp
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Asp Val Ala Asp Gly Trp
1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Gly Val Asp Gln Gln Asp Gly Lys Asn His Trp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Asp Gln Gln Asp Gly Lys Asn Trp
1               5                   10

<210> SEQ ID NO 24
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 24

Val Asp Gln Gln Asp Gly Lys Asn Trp
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Gln Gln Asp Gly Lys Asn Trp
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Asp Gly Lys Asn Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Asp Gln Gln Asp Gly Lys Trp
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Asp Gln Gln Asp Gly Trp
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Asp Gln Gln Asp Trp
1               5
```

```
<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Glu His Asp
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Glu Val Asp
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Glu His Asp
1

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid

<400> SEQUENCE: 33

Xaa Glu Xaa Asp Ala Met Cys
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Glu Val Asp Ala Met Cys
1               5
```

```
<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Glu His Asp Ala Met Cys
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Ala Asp Phe Met Lys
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Tyr Glu Val Asp Gly Trp
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Glu Val Asp Gly Trp
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Asp Gln Met Asp Gly Trp
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

```
Val Gln Val Asp Gly Trp
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Asp Gln Val Asp Gly Trp
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Glu Val Asp Ala Phe Cys
1               5

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Glu Val Asp Gly Arg Lys Lys Arg Arg Gln Arg Arg Arg
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Glu Val Asp Gly Arg Arg Arg Arg Arg Arg Arg Arg Arg
1               5                   10
```